(12) United States Patent
Bradley et al.

(10) Patent No.: US 11,751,817 B2
(45) Date of Patent: Sep. 12, 2023

(54) BREATHING DISORDER IDENTIFICATION, CHARACTERIZATION AND DIAGNOSIS METHODS, DEVICES AND SYSTEMS

(71) Applicant: UNIVERSITY HEALTH NETWORK, Toronto (CA)

(72) Inventors: T. Douglas Bradley, Toronto (CA); Geoffrey Roy Fernie, Etobicoke (CA); Hisham Alshaer, Mississauga (CA); Ahmad Ziad Akl, Toronto (CA)

(73) Assignee: UNIVERSITY HEALTH NETWORK, Toronto (CA)

( * ) Notice: Subject to any disclaimer, the term of this patent is extended or adjusted under 35 U.S.C. 154(b) by 343 days.

(21) Appl. No.: 15/701,091

(22) Filed: Sep. 11, 2017

(65) Prior Publication Data

US 2018/0070890 A1 Mar. 15, 2018

Related U.S. Application Data

(63) Continuation of application No. 14/117,963, filed as application No. PCT/CA2012/000494 on May 17, (Continued)

(51) Int. Cl.
*A61B 5/00* (2006.01)
*A61B 7/00* (2006.01)

(52) U.S. Cl.
CPC .......... *A61B 5/7282* (2013.01); *A61B 5/7475* (2013.01); *A61B 7/003* (2013.01); *A61B 5/4818* (2013.01); *A61B 5/6803* (2013.01)

(58) Field of Classification Search
CPC ... A61B 5/7282; A61B 5/7475; A61B 5/7278; A61B 5/7275; A61B 5/7271;
(Continued)

(56) References Cited

U.S. PATENT DOCUMENTS 3,540,442 A * 11/1970 Holloway .............. A62B 18/08
128/201.19
4,648,407 A 3/1987 Sackner
(Continued)

FOREIGN PATENT DOCUMENTS

CA 2585824 9/2008
EP 2654108 10/2013
(Continued)

OTHER PUBLICATIONS

Alshaer, et al, "Phase tracking of the breathing cycle in sleeping subjects by frequency analysis of acoustic data" International Journal of Healthcare technology and Management 11.3 (2010): 163-175.
(Continued)

*Primary Examiner* — Patrick Fernandes
(74) *Attorney, Agent, or Firm* — BERESKIN & PARR LLP/S.E.N.C.R.L., s.r.l.

(57) ABSTRACT

Disclosed herein are breathing disorder identification, characterization and diagnosis methods, devices and systems. In general the disclosed methods, devices and systems may rely on the characterization of breath sound amplitudes, periodic breath sounds and/or aperiodic breath sounds to characterize a breathing disorder as obstructive (e.g. obstructive sleep apnea—OSA) or non-obstructive (e.g. central sleep apnea—CSA).

19 Claims, 32 Drawing Sheets

Related U.S. Application Data 2012, now Pat. No. 9,801,590, which is a continuation-in-part of application No. PCT/CA2011/000555, filed on May 17, 2011.

(60) Provisional application No. 61/488,362, filed on May 20, 2011, provisional application No. 61/486,855, filed on May 17, 2011.

(58) Field of Classification Search
CPC ... A61B 5/7285; A61B 5/4818; A61B 5/4806; A61B 5/6803; A61B 7/003; A61B 7/006; A61B 5/087; A61B 5/7264; A61B 5/08; G16H 50/20; A61M 16/06; A61M 16/00
See application file for complete search history.

(56) References Cited

U.S. PATENT DOCUMENTS

| | | | |
|---|---|---|---|
| 5,138,666 A * | 8/1992 | Bauer | A62B 18/08 381/385 |
| 5,671,733 A | 9/1997 | Raviv et al. | |
| 5,782,733 A | 7/1998 | Raviv et al. | |
| 5,797,852 A | 8/1998 | Karakasoglu et al. | |
| 5,845,636 A | 12/1998 | Gruenke et al. | |
| 5,961,447 A | 10/1999 | Raviv et al. | |
| 6,045,514 A | 4/2000 | Raviv et al. | |
| 6,142,950 A | 11/2000 | Allen et al. | |
| 6,171,258 B1 | 1/2001 | Karakasoglu et al. | |
| 6,213,955 B1 | 4/2001 | Karakasoglu et al. | |
| 6,290,654 B1 | 9/2001 | Karakasoglu | |
| 6,368,287 B1 | 4/2002 | Hadas | |
| 6,375,623 B1 | 4/2002 | Gavriely | |
| 6,412,485 B1 * | 7/2002 | Saieva | A62B 7/12 128/205.24 |
| 7,118,536 B2 | 10/2006 | Haberland et al. | |
| 7,225,021 B1 | 5/2007 | Park et al. | |
| 7,387,124 B2 | 6/2008 | Noda et al. | |
| 7,785,265 B2 | 8/2010 | Schatzl | |
| 7,850,619 B2 | 12/2010 | Gavish et al. | |
| 2002/0123699 A1 | 9/2002 | Lambert et al. | |
| 2005/0222502 A1 | 10/2005 | Cooper | |
| 2006/0196510 A1 | 9/2006 | McDonald et al. | |
| 2006/0266356 A1 | 11/2006 | Sotos | |
| 2007/0239055 A1 * | 10/2007 | Sowelam | G16H 40/63 600/529 |
| 2008/0001735 A1 | 1/2008 | Tran | |
| 2008/0030105 A1 | 2/2008 | Alder et al. | |
| 2008/0243017 A1 | 10/2008 | Moussavi et al. | |
| 2008/0281220 A1 * | 11/2008 | Sharifpour | A61B 7/003 600/538 |
| 2008/0300500 A1 | 12/2008 | Reisfeld | |
| 2008/0319333 A1 | 12/2008 | Gavish et al. | |
| 2009/0118631 A1 | 5/2009 | Gavish et al. | |
| 2009/0293880 A1 | 12/2009 | Rutan | |
| 2010/0240982 A1 | 9/2010 | Westbrook | |
| 2010/0256512 A1 * | 10/2010 | Sullivan | A61B 5/113 600/529 |
| 2011/0105915 A1 | 5/2011 | Bauer | |
| 2011/0295083 A1 * | 12/2011 | Doelling | A61B 5/11 600/301 |
| 2012/0004749 A1 * | 1/2012 | Abeyratne | G06N 7/005 700/94 |
| 2012/0071741 A1 * | 3/2012 | Moussavi | A61B 5/4818 600/340 |
| 2013/0253357 A1 * | 9/2013 | Moussavi | A61B 5/4818 600/529 |

FOREIGN PATENT DOCUMENTS

| | | |
|---|---|---|
| GB | 2214302 | 8/1989 |
| WO | WO2000019895 | 4/2000 |
| WO | WO015602 | 3/2001 |
| WO | WO0193743 | 12/2001 |
| WO | WO2006008745 | 1/2006 |
| WO | WO2010054481 | 5/2010 |
| WO | WO2011010384 | 1/2011 |
| WO | WO2012058727 | 5/2012 |

OTHER PUBLICATIONS

Nakano, et al. "Validation of a new system of tracheal sound analysis for the diagnosis of sleep apnea-hypopnea syndrome" Sleep—New York Then Westchester—27.5 (2004): 951-958.

Sovijarvi, et al. "Averaged and time-gated spectral analysis of respiratory sounds: repeatability of spectral parameters in healthy men and in patients with fibrosing alveolitis" Chest Journal (1996): 1283-1290.

EP Extended Search Report for EP Application No. EP 12784876.0 (University Health Network), dated Apr. 17, 2015.

EP Extended Search Report for EP Application No. EP 1276596.2 (University Health Network), dated Mar. 20, 2015.

Abeyratne et al., "Pitch jump probability measures for the analysis of snoring sounds in apnea," Physiological Measurement, vol. 26, pp. 779-798, 2005.

Alshaer et al., "Adaptive segmentation and normalization of breathing acoustic data of subjects with obstructive sleep apnea," Paper presented at: Science and Technology for Humanity (TIC-STH), 2009, IEEE Toronto International Conference; Sep. 26-27, 2009.

Alshaer et al., "Development and validationof an algorithm for detection of apneas and hyponeas using overnight breath sound recordings," American J. of Resp. Crit. Care Med., vol. 183, Meeting Abstracts A6317, D108 Diagnosis and Management of Sleep Disorders,Poster Discussion Session URL: http://aireem.atsjoumals.org/cgi/reprint/183/1_meetingabstracts/A6317, (2011).

Shahar et al., "Sleep-disordered breathing and cardiovascular disease: cross-sectional results of the Sleep Heart Health Study," Am J Respir Crit Care Med, vol. 163, pp. 19-25 (2001).

Argod, et al., "Differentiating Obstructive and Central Sleep Respiratory Events through Pulse Transit Time," Am. J. Respir. Crit. Care Med., vol. 158:6, pp. 1778-1783 (1998).

Arzt et al., "Association of sleep-disordered breathing and the occurrence of stroke," Am J Respir Crit Care Med, vol. 172, pp. 1447-1451 (2005).

Bieger-Farhan et al., "Portable method for the determination of snoring site by sound analysis," Journal of Laryngology & Otology, vol. 118, pp. 135-138 (2004).

Bradley et al., "Sleep apnea and heart failure: Part I: obstructive sleep apnea," Circulation, vol. 107, pp. 1671-1678, Apr. 1, 2003.

Campbell et al., "The perception of wakefulness within sleep," Sleep, vol. 4, pp. 177-183 (1981).

Cavusoglu et al., "Investigation of sequential properties of snoring episodes for obstructive sleep apnoea identification," Physiol Meas., vol. 29:8, pp. 879-898 (2008).

Dalmay et al., "Acoustic Properties of the Normal Chest," Eur. Resp. Jrnl., vol. 8, pp. 1761-1769 (1995).

Duckitt et al., "Automatic detection, segmentation and assessment of snoring from ambient acoustic data," Physiological Measurement, vol. 27, pp. 1047-1056 (2006).

Fiz et al., "Analysis of forced wheezes in asthma patients," Respiration, vol. 73, pp. 55-60, (2006).

Fiz et al., "Detection of wheezing during maximal forced exhalation in patients with obstructed airways," Chest, vol. 122, pp. 186-191 (2002).

Fiz et al., "Acoustic analysis of snoring sound in patients with simple snoring and obstructive sleep apnea," European Respiratory Journal, vol. 9, pp. 2365-2370 (1996).

Fiz et al., Wheezing identification in asthma subjects during forced exhalation, American Journal Of Respiratory And Critical Care Medicine, vol. 159, p. A652 (1999).

Folke et al., "Critical review of non-invasive respiratory monitoring in medical care," Med Biol Eng Comput, vol. 41, pp. 377-383 (2003).

Fritsch et al., "Monotone piecewise cubic interpolation," SIAM Journal on Numerical Analysis, vol. 17, pp. 238-246 (1980).

(56) References Cited

OTHER PUBLICATIONS

Gavriely et al., "Parametric representation of normal breath sounds," J App/ Physiol, vol. 73:5, pp. 1776-1784 (1992).
Guler et al., "Two-stage classification of respiratory sound patterns," Comput Biol Med, vol. 35, pp. 67-83 (2005).
Harrington et al., Techniques in Speech Acoustics: Kluwer Academic Publisher (1999).
Hill et al., "Palatal snoring identified by acoustic crest factor analysis," Physiological Measurement, vol. 20, pp. 167-174 (1999).
Hoffstein et al., "Snoring: is it in the ear of the beholder?" Sleep, vol. 17, pp. 522-526 (1994).
Hult et al., "A bioacoustic method for timing of the different phases of the breathing cycle and monitoring of breathing frequency," Med Eng Phys, vol. 22, pp. 425-433 (2000).
Hult et al., "An improved bioacoustic method for monitoring of respiration," Technol Health Care, vol. 12, pp. 323-332 (2004).
Jane et al., "Analysis of wheezes in asthmatic patients during spontaneous respiration," Conf Proc IEEE Eng Med Biol Soc, vol. 5, p. 3836 (2004).
Jane et al., "Automatic detection of snoring signals: Validation with simple snorers and OSAS patients," Proceed of the 22nd Annual EMBS Intl Conf., pp. 3129-3130 (2000).
Jane et al., "Automatic snoring signal analysis in sleep studies," Proceed of the 25th Annual Intl Conf of the IEEE EMBS, Cancun, Mexico, pp. 366-369 (2003).
Leung et al., "Sleep apnea and cardiovascular disease," Am J Respir Crit Care Med, vol. 164, pp. 2147-2165 (2001).
MacKay, "Information Theory, Inference & Learning Algorithms," Cambridge, UK: Cambridge University Press, ch. 20, pp. 284-286 (2003).
Mattei et al., "Diagnosis of sleep apnea," Minerva Med, vol. 95, pp. 213-231 (2004).
Michael et al., "Analysed snoring sounds correlate to obstructive sleep disordered breathing," European Archives of Oto-Rhino-Laryngology, vol. 265:1, pp. 105-113 (2008).
Nakano et al., "Automatic detection of sleep-disordered breathing for a single-channel airflow record," European Respiratory Journal, 29(4): 728-736 (2007).
Ng et al., "Could formant frequencies of snore signals be an alternative means for the diagnosis of obstructive sleep apnea?" Sleep Medicine, vol. 9:8, pp. 894-898 (2008).
Ng et al., "Role of upper airway dimensions in snore production: Acoustical and perceptual findings," Annals of Biomedical Engineering., vol. 37:9, pp. 1807-1817 (2009).
Nieto et al., "Association of sleep-disordered breathing, sleep apnea, and hypertension in a large community-based study. Sleep Heart Health Study," Jama, vol. 283, pp. 1829-1836 (2000).
Perez-Padilla et al., "Characteristics of the snoring noise in patients with and without occlusive sleep apnea," American Review of Respiratory Disease, vol. 147:3, pp. 635-644 (1993).
Quinn et al., "The differentiation of snoring mechanisms using sound analysis," Clinical Otolaryngology & Allied Sciences, vol. 21, pp. 119-123 (1996).
Rabiner et al., "Fundamentals of Speech Recognition," Prentice Hall, p. 100-103 (1993).
Radfar et al., "A maximum likelihood estimation of vocal-tract-related filter characteristics for single channel speech separation," EURASIP Journal on Audio, Speech, and Music Processing, vol. 2007, Art. ID 84186, pp. 1-15 (2007).
Rechtschaffen et al., "A Manual of Standardized Terminology, Techniques and Scoring System for Sleep Stages of Human Subjects," Los Angeles: UCLA Brain Information Service/Brain Research Institute (1968).
Sankur et al., "Comparison of AR-based algorithms for respiratory sounds classification," Comput Biol Med, vol. 24, pp. 67-76 (1994).
Sankur et al., "Multiresolution biological transient extraction applied to respiratory crackles," Comput Biol Med, vol. 26, pp. 25-39 (1996).
Sen et al., "A multi-channel device for respiratory sound data acquisition and transient detection," Conf Proc IEEE Eng Med Biol Soc, vol. 6, pp. 6658-6661 (2005).
Shiota et al., "Alterations in upper airway cross-sectional area in response to lower body positive pressure in healthy subjects," Thorax, vol. 62, No. 10, pp. 868-872, Oct. 2007.
"Sleep-related breathing disorders in adults: recommendations for syndrome definition and measurement techniques in clinical research," The Report of an American Academy of Sleep Medicine Task Force, Sleep. 1999, 22(5):667-689.
Sola-Soler et al., "Pitch analysis in snoring signals from simple snorers and patients with obstructive sleep apnea in Engineering in Medicine and Biology," 24th Annual Conf and the Annual Fall Mtg of the Biomedi Engineer Soc, EMBS/BMES Conf. Proceedings of the Second Joint (2002).
Sola-Soler et al., "Variability of snore parameters in time and frequency domains in snoring subjects with and without Obstructive Sleep Apnea," Conf Proc IEEE Eng Med Biol Soc, vol. 3, pp. 2583-2586 (2005).
Steltner et al., "Diagnosis of Sleep Apnea by Automatic Analysis of Nasal Pressure and Forced Oscillation Impedance," Am. J. Respir. Crit. Care Med., vol. 165:7, pp. 940-944 (2002).
Stock et al., "Development and application of a real-time monitoring and feedback system for deep inspiration breath hold based on external marker tracking," Medical physics., vol. 33:8, p. 2868 (2006).
Thomas et al., "Differentiating Obstructive from Central and Complex Sleep Apnea Using an Automated Electrocardiogram-Based Method," Sleep, vol. 30:12, pp. 1756-1769 (2007).
Varady et al., "A novel method for the detection of apnea and hypopnea events in respiration signals," IEEE Transactions on Biomedical Engineering, 49(9): 936-942 (2002).
Vegfors et al., "Presentation and evaluation of a new optical sensor for respiratory rate monitoring," Int J Clin Monit Comput, vol. 11, pp. 151-156 (1994).
Wakwella et al., "Automatic Segmentation and Pitch/Jitter Tracking of Sleep Disturbed Breathing Sounds," 8th International Conf on Control, Automation, Robotics and Vision, Kunming, China., IEEE, p. 936-940 (2004).
Wang et al., "A simple respiration gating technique and its application in high-resolution PET camera," IEEE Transactions on Nuclear Science, vol. 52:1, p. 125 (2005).
Werthammer et al., "Apnea monitoring by acoustic detection of airflow," Pediatrics, 71(1): 53-55 (1983).
Xiong et al., "Problems in Timing of Respiration with the Nasal Thermistor Technique," J Am Soc of Echocardio, vol. 6:2, pp. 210-216 (1993).
Yeginer et al., "Modeling of pulmonary crackles using wavelet networks," Conf Proc IEEE Eng Med Biol Soc, vol. 7, pp. 7560-7563 (2005).
Young et al., "The occurrence of sleep-disordered breathing among middle-aged adults," N Engl J Med, vol. 328, pp. 1230-1235 (1993).
Young et al., "Estimation of the clinically diagnosed proportion of sleep apnea syndrome in middle-aged men and women," Sleep, vol. 20, pp. 705-706 (1997).
Int'l Search Report & Written Opinion issued in application No. PCT/CA09/01644 (dated 2010).
International Preliminary Report on Patentability issued in Int'l Patent Application No. PCT/CA2009/001644 (dated 2010).
International Search Report issued in Intl Patent Application No. PCT/CA2011/000555 (dated 2011).
International Search Report issued in Int'l Application No. PCT/CA2012/000494 (dated 2012).
International Search Report issued in Int'l Application No. PCT/CA2012/000478 (dated 2012).

* cited by examiner

BREATHING DISORDER IDENTIFICATION, CHARACTERIZATION AND DIAGNOSIS METHODS, DEVICES AND SYSTEMS

FIELD OF THE DISCLOSURE

The present disclosure relates to the detection of breathing disorders, and in particular, to breathing disorder identification, characterization and diagnosis methods, devices and systems.

BACKGROUND

Sleep apnea (SA) is a breathing disorder characterized by repetitive complete or partial cessations of breathing (apneas and hypopneas, respectively) during sleep. The frequency of these events ranges from 5 to 100 times/hour depending on the severity of the case. As a result, patients suffer from poor sleep quality, daytime sleepiness, and poor cognitive performance. Sleep apnea can generally be characterized as one of two types—obstructive and central sleep apnea (OSA and CSA, respectively). It has been observed that OSA, which is the most common type, increases the risk of developing hypertension, heart failure (HF), and stroke by 3 to 4 fold. Also, patients with untreated sleep apnea generally consume twice as many healthcare resources for treatment of cardio-respiratory diseases than subjects without the disease. On the other hand, it has been demonstrated that treating OSA in patients with hypertension or HF lowers blood pressure, and dramatically improves cardiovascular function. Therefore, diagnosing and treating such patients could have a very substantial beneficial medical and public health impact. Unfortunately, the majority of people with sleep apnea remain undiagnosed due to the lack of accessibility to expensive overnight monitoring in a sleep laboratory presently required for diagnosis.

Obstructive sleep apnea (OSA) is generally understood to result from partial or complete collapse of the pharynx or the upper airway (UA) resulting in obstruction of the airflow pathway. In OSA, the respiratory drive is still present but the patient is breathing against a high resistance tube—a situation that mimics chocking. Thus, the hallmark of OSA is narrowing, obstruction, or total closure of the upper airway (pharynx). This results in characteristic breath sounds such as the occurrence of snoring and turbulent sounds. Each event generally lasts 10 to 60 seconds, thus generally causing episodes of oxygen deprivation and often provoking arousals from sleep and consequent sleep fragmentation. As a result, patients suffer from poor sleep quality, daytime sleepiness, and impaired cognitive performance. It is a common disease affecting approximately 7% of adults. Nevertheless, the majority of patients with OSA remain undiagnosed; in one study, it was shown that 93% of women and 82% of men with moderate to severe OSA had not been diagnosed.

Central sleep apnea (CSA), on the other hand, is generally understood to occur when there is a temporary cessation of respiratory output from the respiratory neurons in the brainstem to the muscles of respiration. This lack of respiratory muscle activation causes a temporary cessation of airflow (i.e. central apnea), during which there is no respiratory ventilation. In contrast to OSA, the upper airway is usually open during CSA, and thus chocking sounds and snoring are less likely to occur. Further, when airflow resumes, snoring does not necessarily occur because the pharynx is usually not obstructed.

The distinction between CSA and OSA can be of particular importance in choosing the management of the sleep apnea and associated diseases. This is especially important in patients with heart failure (HF) or stroke in whom CSA is common and is associated with increased mortality risk. Patients with HF have a very high prevalence of both OSA and CSA. The distinction is important for choosing the appropriate therapy. For example, in OSA, therapy usually consists of Continuous Positive Airway Pressure (CPAP), whereas in CSA the treatment strategy is generally to first treat the underlying HF, and if CSA persists, to use adaptive servo ventilation, oxygen or CPAP. It has also been shown that suppression of CSA by CPAP in HF patients improves the cardiovascular function, and tends to improve survival.

Presently, the standard means of identifying and diagnosing sleep apnea is via overnight polysomnography (PSG), in which the patients have to sleep in a laboratory attached to many monitoring electrodes under the supervision of a technician. PSG is expensive and access to it is limited, resulting in long waiting lists in the limited areas where PSG is available.

For this reason, interest has been raised in devising new methods to diagnose sleeping disorders, such as SA. For example, acoustic analysis of respiratory sounds has gained an increasing role in the study of respiratory disorders such as in identifying pathological respiratory sounds including wheezes and crackles, and to study and locate the site of snoring. In some sleep studies, snoring sounds were captured above the mouth level, as were tracheal sounds, to study snoring, particularly as snoring is a component of the disease itself and is produced at the very location where narrowing and obstruction takes place.

Despite recent findings, snore-driven techniques have fundamental limitations from the clinical perspective. For instance, snoring does not necessarily occur in all types of SA, such as in CSA. Furthermore, snore-driven techniques generally fail to assess the severity of an identified condition. For example, while snoring is a hallmark of OSA, it might not necessarily take place with each apnea and hypopnea. Accordingly, assessing the disease severity in terms of frequency of apneas per hour might be underestimated if some apneas are missed due to absence of snoring, for example. As knowledge about the disease severity can be beneficial in selecting an appropriate treatment strategy, snore-driven techniques can be less than ideal.

Accordingly, while some work has been done to detect the occurrence of OSA from snoring sounds, there remains much room for improvement, be it in the development of a reliable technique for differentiating between OSA and CSA occurrences, or identifying CSA altogether, and/or for evaluating the severity of such occurrences. Demand is also increasing for reliable apnea identification, characterization and/or diagnostic techniques that can be accessed by a wider base of the population, for example as compared to the technician-assisted PSG techniques currently implemented in dedicated sleep laboratories.

Therefore, there remains a need for new breathing disorder identification, characterization and diagnosis methods, devices and systems that overcome at least some of the drawbacks of known techniques, or at least, provides the public with a useful alternative.

This background information is provided to reveal information believed by the applicant to be of possible relevance to the invention. No admission is necessarily intended, nor should be construed, that any of the preceding information constitutes prior art against the invention.

SUMMARY

An object of the invention is to provide one or more breathing disorder identification, characterization and/or diagnosis methods, devices and/or systems, or at least provide the public with a useful alternative.

In accordance with one embodiment of the invention, there is provided a method for automatically characterizing recorded breath sounds as indicative of one of obstructive and central sleep apnea, the method comprising: identifying a segment of the recorded breath sounds encompassing at least one of an apnea and a hypopnea; automatically evaluating a breath sound amplitude profile of said identified segment against one or more preset sound amplitude profile criteria set to distinguish between segments indicative of obstructive sleep apnea and central sleep apnea; and classifying said identified segment as being indicative of one of obstructive and central sleep apnea based on a result of said evaluating step.

In accordance with another embodiment, there is provided a method for automatically characterizing recorded breath sounds acquired from a candidate while sleeping, as potentially indicative of an obstructive breathing disorder, the method comprising: automatically identifying periodic breath sound segments and aperiodic breath sound segments from said recorded breath sounds; extracting from said identified periodic breath sound segments one or more periodic breath sound characteristics; evaluating said extracted periodic breath sound characteristics against one or more corresponding periodic breath sound classification criteria predetermined to distinguish obstructive breathing events from non-obstructive breathing events; extracting from said identified aperiodic breath sound segments one or more aperiodic breath sound characteristics; evaluating said extracted aperiodic breath sound characteristics against one or more corresponding aperiodic breath sound classification criteria predetermined to distinguish obstructive breathing events from non-obstructive breathing events; and combining results of both of said evaluating steps to provide indication as to whether the candidate likely suffers from an obstructive breathing disorder.

In accordance with another embodiment of the invention, there is provided a method for automatically characterizing recorded breath sounds acquired from a candidate while sleeping as potentially indicative of an obstructive breathing disorder, the method comprising: automatically identifying a periodic breath sound segment; extracting a pitch contour of said identified segment; evaluating said extracted pitch contour against one or more preset pitch contour characteristics predetermined to distinguish obstructive breathing events from non-obstructive breathing events; and characterizing said segment as indicative of an obstructive breathing event or a non-obstructive breathing event based on a result of said evaluating step.

In accordance with another embodiment, there is provided a method for automatically characterizing recorded breath sounds acquired from a candidate while sleeping as potentially indicative of an obstructive breathing disorder, the method comprising: automatically identifying an aperiodic breath sound segment; extracting a spectral characteristic of said identified segment; evaluating said extracted spectral characteristic against one or more preset spectral characteristics predetermined to distinguish obstructive breathing events from non-obstructive breathing events; and characterizing said segment as indicative of an obstructive breathing event or a non-obstructive breathing event based on a result of said evaluating step.

In accordance with another embodiment, there is provided a method for automatically characterizing recorded breath sounds as indicative of OSA or CSA, the method comprising: isolating one or more segments of the recorded breath sounds encompassing at least one of an apnea and a hypopnea; automatically evaluating a sound amplitude variation manifested in at least one of said one or more segments against corresponding characteristic amplitude variations previously associated with breath sounds generated during known OSA and CSA events; automatically evaluating a frequency characteristic manifested in at least one of said one or more segments against corresponding frequency characteristics previously associated with breath sounds generated during known OSA and CSA events; and combining results from each of said evaluating steps to characterize the recorded breath sounds as indicative of OSA or CSA.

In accordance with another embodiment, there is provided a method for automatically distinguishing recorded breath sounds as indicative of OSA versus CSA, the method comprising: isolating one or more segments of the recorded breath sounds each encompassing at least one apnea or hypopnea; automatically extracting one or more characteristics of said recorded breath sounds manifested during each of said one or more segments; automatically evaluating said one or more characteristics against respective preset characteristics previously associated with breath sounds generated during known OSA and CSA events; and outputting, as a result of said evaluating step, an indication as to a likely characterization of said segment as representative of OSA or CSA.

In accordance with another embodiment, the methods further comprise the step of acquiring breath sounds via a face mask comprising a microphone disposed, upon a candidate wearing the mask during sleep, at a distance above a nose and mouth area of the candidate's face.

In accordance with another embodiment, the above methods are automatically implemented by one or more processors of a computing system, and further comprise outputting, via a user interface, an indication of a candidate's condition.

In accordance with another embodiment, there is provided computer-readable media comprising statements and instructions stored thereon for implementation by one or more processors of a computing system to automatically characterize recorded breath sounds in accordance with the steps of the above methods.

In accordance with another embodiment, there is provided a system for automatically characterizing recorded breath sounds comprising: one or more processors; and a computer-readable medium accessible by said one or more processors and having stored thereon statements and instructions executable thereby to operate on said recorded breath sounds in accordance with the above methods.

Other aims, objects, advantages and features of the invention will become more apparent upon reading of the following non-restrictive description of specific embodiments thereof, given by way of example only with reference to the accompanying drawings.

BRIEF DESCRIPTION OF THE FIGURES

Several embodiments of the present disclosure will be provided, by way of examples only, with reference to the appended drawings, wherein:

FIG. 7A is an illustrative waveform plot of breathing sounds acquired from a single breath showing both an inspiration phase and an expiration phase, whereas

FIGS. 10A to 10C are plots of successively preprocessed digitized breathing sounds, wherein FIG. 10B is a plot of the digitized breathing sounds of FIG. 10A with outliers removed and a segment thereof defined for segment-based normalization, and wherein FIG. 10C is a plot of the digitized breathing sounds of FIG. 10B after segment-based normalization, in accordance with one embodiment of the invention;

FIGS. 19A and 19B are exemplary plots of a breathing envelope and extracted breathing effort envelope thereof for respective events of interest, and particularly illustrating respective fall/rise patterns thereof, wherein FIG. 20A illustrates a decrescendo/crescendo pattern generally associated with CSA, whereas

FIGS. 20A and 20B are plots of exemplary raw acoustic breath sound waveforms for candidates having CSA and OSA, respectively;

FIGS. 24A and 24B are exemplary fundamental frequency plots for periodic breathing sounds identified during successive breathing cycles, wherein FIG. 24A illustrates a relatively stable pitch contour generally representative of a stable airway and indicative of CSA or an absence of sleep apnea, whereas FIG. 24B illustrates a relatively variable pitch contour generally representative of a collapsible airway and indicative of OSA;

DETAILED DESCRIPTION

With reference to the disclosure herein and the appended figures, various breathing disorder identification, characterization and/or diagnosis methods and devices will be described. Namely, the following describes various methods and devices that can be used, in combination or alone, to achieve various levels of breathing disorder identifications, characterizations and/or diagnoses. In some embodiments, such methods and devices rely, at least in part, on the analysis of breath-related sounds. For example, in some embodiments, the methods and devices described herein can be used to detect sleep apnea via acoustic breath sound analysis, such as from overnight breath sound recordings and the like, and in some embodiments, to further quantify a severity of this disorder in a given subject, to distinguish between OSA and CSA, and/or achieve other related characterizations of the subject's condition. Such results present significant improvements in the provision of a less invasive approach to sleep apnea identification, characterization and/ or diagnosis, particularly as compared to PSG and other such techniques. Namely, and in accordance with some embodiments, useable results can be achieved using as few as a single non-invasive acoustic breathing sound channel to achieve sleep apnea identification, characterization and/or diagnosis, which may further include characterization of a severity of the identified apnea and/or differentiation between OSA and CSA.

Figure 1:
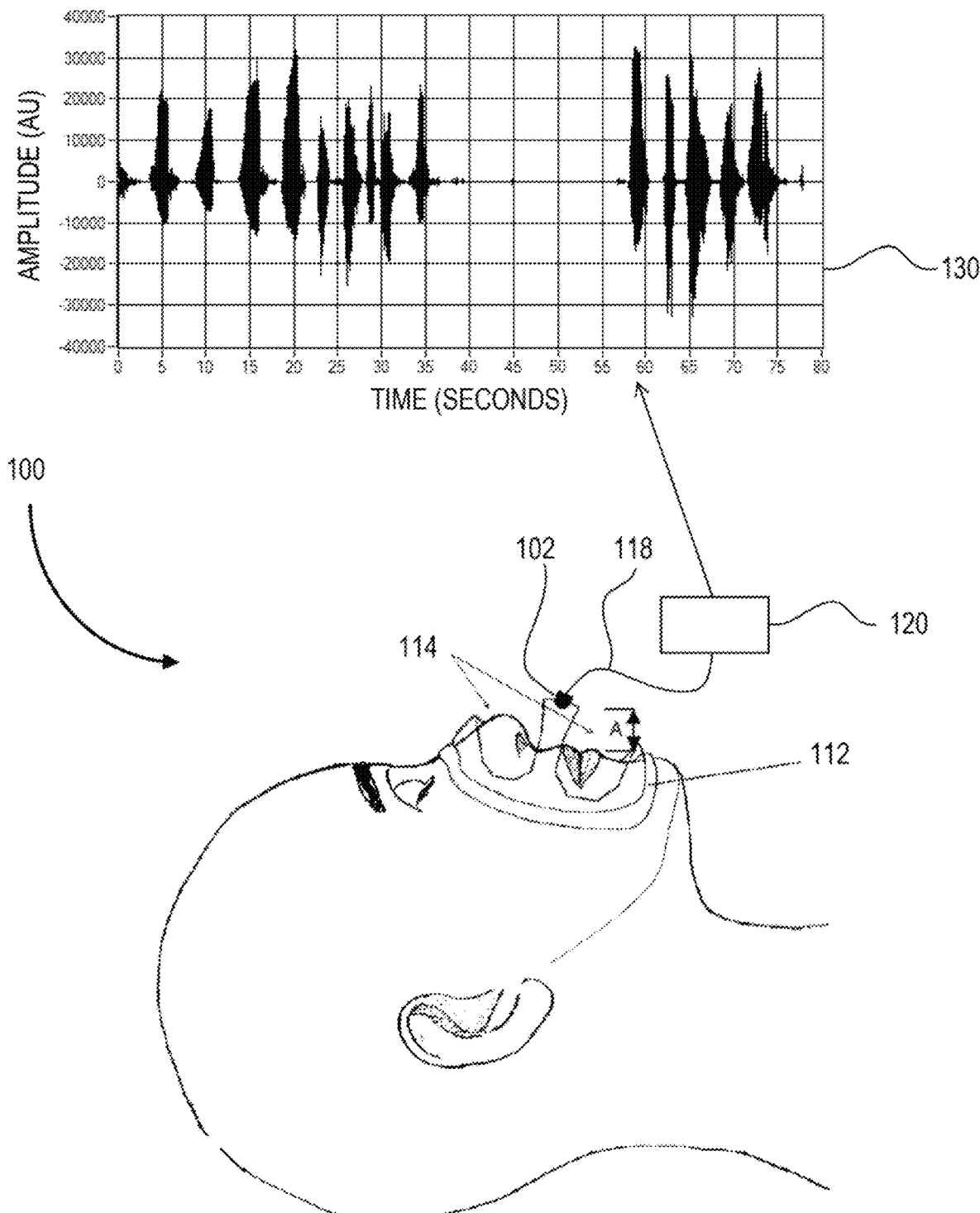
FIG. 1 is a diagram of a system for breathing disorder identification, characterization and/or diagnosis, in accordance with one embodiment of the invention.

With reference now to FIG. 1, and in accordance with one embodiment, a system 100 for use in identifying, characterizing and/or diagnosing a breathing disorder via breath sound analysis will now be described. In this embodiment, the system 100 generally provides for the recordal of breath sound data, in this example, via one or more transducers, such as microphone 102, disposed at a distance A from a nose and mouth area of a candidate's face in a face mask 112 to be worn by the candidate during testing. For example, the mask may be worn during sleep if seeking to identify sleep-related disorders such as sleep apnea. As schematically depicted, the one or more transducers 102 are operatively coupled to a data recording/processing module 120 for recording breath sound data, illustratively depicted by raw signal plot 130, for processing.

In this example, the microphone 102 is coupled in or to a loose fitting full face mask 112 which includes at least one opening 114 to allow for ease of breathing, and provides for a communication path 118, be it wired and/or wireless, from the microphone 102 to the recording/processing module 120.

Figure 2:
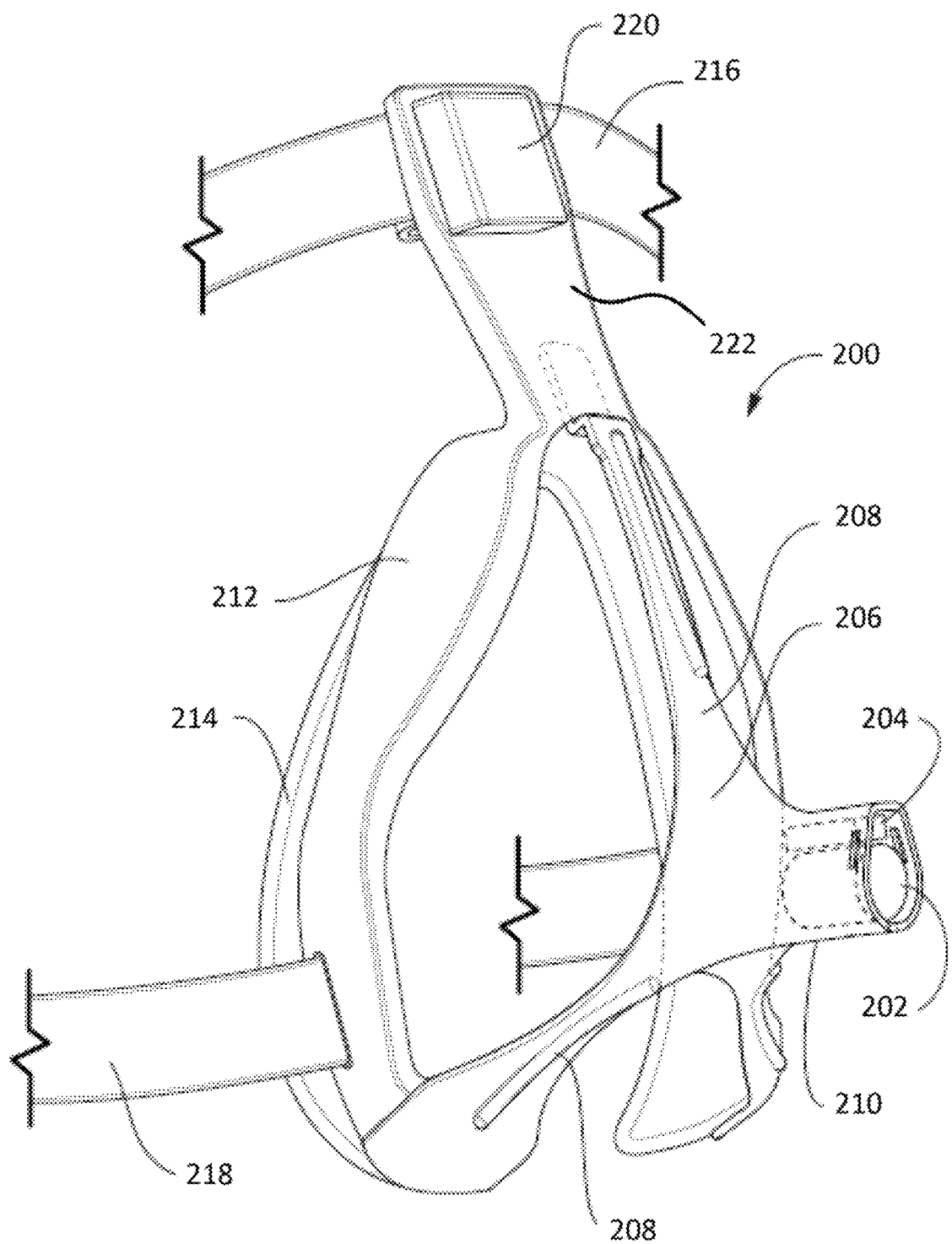
FIG. 2 is a perspective view of a mask for use in acquiring breathing sounds from a candidate, for example within the context of the system of FIG. 1, in accordance with one embodiment of the invention.

FIG. 2 provides another example of a mask 200 usable in acquiring breathing sounds suitable in the present context. In this example, the mask 200 generally comprises at least one transducer, such as microphones 202 and 204, and a support structure 206 for supporting same above a nose and mouth area of the subject's face. The support structure 206 is generally shaped and configured to rest on the subject's face and thereby delineate the nose and mouth area thereof, and comprises two or more outwardly projecting limbs 208 (e.g. three limbs in this example) that, upon positioning the mask 200, converge into a transducer supporting portion 210 for supporting microphones 202 and 204 at a distance from this area.

The support structure further comprises an optional frame 212 and face resting portion 214 shaped and configured to contour the face of the subject and at least partially circumscribe the nose and mouth area of the subject's face, thereby facilitating proper positioning of the mask on the subject's face and providing for greater comfort. A restraining mechanism, such as head straps 216 and 218, can be used to secure the mask to the subject's face and thereby increase the likelihood that the mask will remain in the proper position and alignment during use, e.g. even when the subject is sleeping in monitoring certain breathing disorders such as sleep apnea.

In this embodiment, the mask 200 further comprises an integrated recording device 220, such as a digital recording device or the like, configured for operative coupling to the at least one transducer, such as microphones 202 and 204, such that sound and/or airflow signals generated by the at least one transducer can be captured and stored for further processing, for example via one or more data processing modules (not shown). In this particular embodiment, the recording device 220 is disposed on a frontal member 222 of the support structure 206, thereby reducing an obtrusiveness thereof while remaining in close proximity to the at least one transducer so to facilitate signal transfer therefrom for recordal. In providing an integrated recording device, the mask 200 can effectively be used as a self-contained respiratory monitoring device, wherein data representative of the subject's breathing can be stored locally on the mask and transferred, when convenient, to a remotely located respiratory diagnostic center, for example. Further details as to the design, features and use of mask 200 are provided in U.S. Patent Application Publication No. 2011/0092839 and International Application Publication No. WO 2012/037641, the entire contents of each one of which is hereby incorporated herein by reference.

Figure 3:
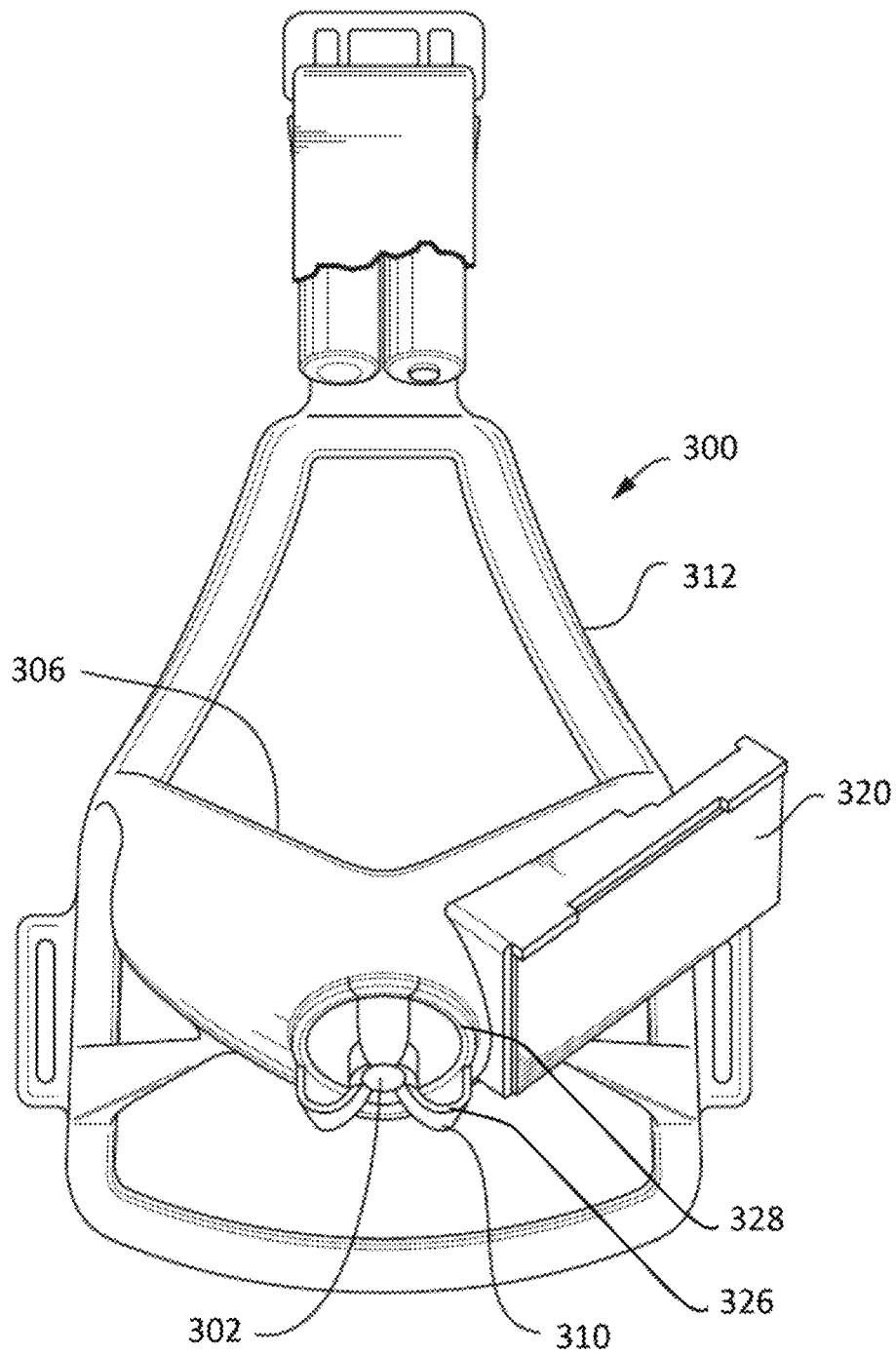
FIGS. 3 and 4 are front and side views, respectively, of a mask for use in acquiring breathing sounds from a candidate, for example within the context of the system of FIG. 1, in accordance with another embodiment of the invention.
Figure 4:
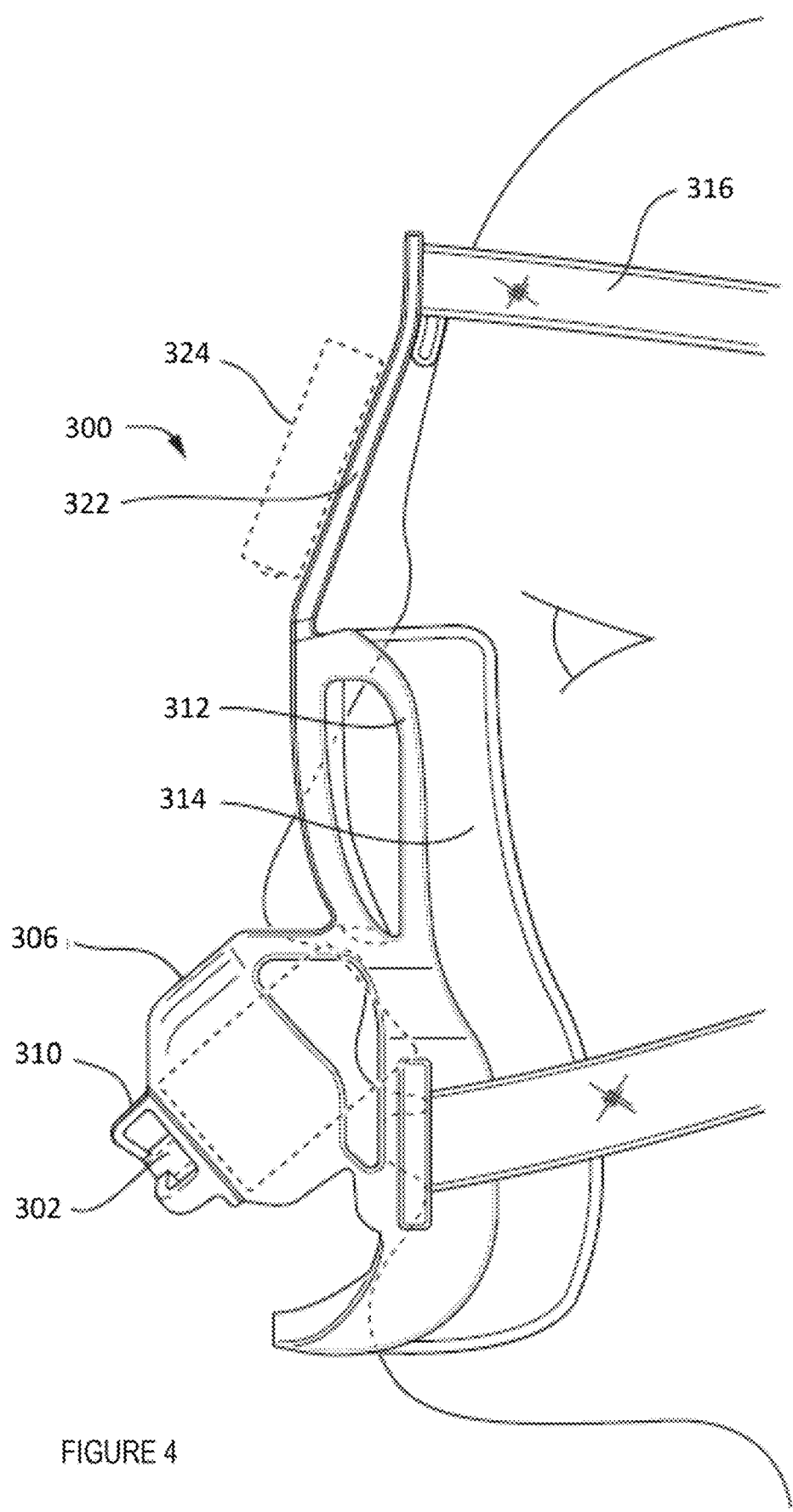

FIGS. 3 and 4 provide yet another example of a mask 300 usable in acquiring breathing sounds suitable in the present context. In this example, the mask 300 comprises at least one transducer, such as microphone 302, and a support structure 306 for supporting same above a nose and mouth area of the subject's face. The support structure 306 is generally shaped and configured to rest on the subject's face and extend outwardly therefrom over a nose and mouth area thereof to provide a transducer supporting portion 310 for supporting the microphone 302, upon positioning the mask, at a distance from this area.

In this example, the support structure 306 is shaped and configured to support the transducer 302 above the nose and mouth area at a preset orientation in relation thereto, wherein the preset orientation may comprise one or more of a preset position and a preset angle to intercept airflow produced by both the subject's nose and mouth. For example, in one embodiment, the preset orientation may be preset as a function of an estimated intersection between nasal and oral airflow, for example based on an observed or calculated average intersection between such airflows. For instance, in one embodiment, the preset orientation may comprise a preset position that, upon positioning the mask on the subject's face, is substantially laterally centered relative to the subject's face and longitudinally substantially in line with or below the subject's mouth, thus generally intercepting oral and nasal airflow.

In a same or alternative embodiment, the preset orientation may comprise a preset angle that aligns the microphone, or a principle responsiveness axis thereof, along a line more or less representative of an averaging between general oral and nasal airflows. For instance, in one embodiment, the orientation angle is preset to more or less bisect an angle formed by the transducer's preset position relative to the subject's nose (i.e. nostrils) and mouth. This bisecting angle, which should be construed within the present context to represent an angle more or less directing the transducer's principal responsiveness axis toward a point somewhere between the wearer's nose and mouth, may be determined as a function of measured, observed and/or otherwise estimated nasal and oral breathing patterns, so to improve or enhance the transducer's general responsiveness to airflow originating from the nose and/or mouth of the candidate. Generally, the preset orientation may thus, in accordance with one embodiment of the invention, comprise a preset angle that, upon positioning the mask on the subject's face, substantially aligns the transducer with a point between the subject's nose and mouth.

In this embodiment, the support structure 306 generally comprises two outwardly projecting limbs that flow continuously one within the other toward the transducer supporting portion 310 in defining a funneling shape that substantially converges toward this transducer supporting portion, thus effectively redirecting nasal and/or oral airflow toward the transducer 302 and allowing for effective monitoring of airflow produced by both the subject's nose and mouth while breathing. Accordingly, breathing airflow, which will generally more or less diverge laterally from the candidate's nostrils as it is projected more or less obliquely downward therefrom can be effectively collected, at least partially, by the generally concave support structure 306 to be substantially funneled thereby toward the transducer 302. Accordingly, in this embodiment, not only is the transducer's preset orientation generally selected as a function of an estimated nasal and oral airflow intersection, the general funneling shape of the support structure 306 will further redirect at least a portion of laterally diverging nasal (and oral) airflow toward the transducer 302. Similarly, though not explicitly depicted herein, the same generally concave shape of the funneling support structure 306 will, partly due to its upwardly titled orientation in this embodiment, also at least partially redirect longitudinally divergent airflow toward the transducer 302.

The transducer supporting portion 310 of the support structure 306 further comprises one or more (three in this embodiment) transducer supporting bridges or limbs 326 extending from a transducer-surrounding aperture 328 defined within the support structure 306. In this embodiment, the provision of bridging limbs 326 may allow for a general reduction in airflow resistance, which may result in substantially reduced dead space. For example, while the general funneling shape of the support structure 306 allows for a redirection of airflow toward the transducer 302, the bridged aperture 328 allows for this flow of air to continue beyond the transducer 302, and thereby reduce the likelihood of this flowing air pooling within the mask and/or flowing back onto itself, which could otherwise lead to a generally uncomfortable warm/humid flow of breath back in the candidate's face (and which could thus be breathed in again), and/or lead to unusual flow patterns and/or sounds that could further complicate data processing techniques in accounting for these patterns.

The support structure 306 further comprises an optional frame 312 and face resting portion 314 shaped and configured to contour the face of the subject and at least partially circumscribe the nose and mouth area of the subject's face, thereby facilitating proper positioning of the mask on the subject's face and providing for greater comfort. A restraining mechanism, such as head straps 316, can be used to secure the mask to the subject's face and thereby increase the likelihood that the mask will remain in the proper position and alignment during use, even when the subject is sleeping, for example, in monitoring and diagnosing certain common breathing disorders. It will be appreciated that the data analysis techniques described below may also be applicable, in some conditions, in monitoring and diagnosing a subject's breathing when awake.

In this embodiment, the mask 300 further comprises a recording device 320, such as a digital recording device or the like, configured for operative coupling to the at least one transducer 302, such that breath sound signals generated by the at least one transducer can be captured and stored for further processing. In this particular embodiment, the recording device 320 is disposed on one of the limbs of the support structure 306, thereby reducing an obtrusiveness thereof while remaining in close proximity to the at least one transducer so to facilitate signal transfer therefrom for recordal. A battery pack 324, operatively coupled to the recording device 320, is provided on a frontal member 322 of the mask 300 to power the recording device and transducer in acquiring data free of any external wiring or the like. In providing an integrated and self-supported recording device, the mask 300 can effectively be used as a self-contained respiratory monitoring device, wherein data representative of the subject's breathing can be stored locally on the mask and transferred, when convenient, to a remotely located respiratory diagnostic center, for example.

Further details as to the design, features and use of mask 300 are provided in International Application Publication No. WO 2012/037641, the entire content of which is incorporated herein by reference.

As will be appreciated by the person of ordinary skill in the art, the general shape and design of the above-described masks (200, 300) can provide, in different embodiments, for an improved responsiveness to airflow produced by the subject while breathing, and that irrespective of whether the subject is breathing through the nose or mouth, predominantly through one or the other, or through both substantially equally. Namely, the ready positioning of an appropriate transducer responsive to airflow relative to the nose and mouth area of the subject's face is provided for by the general spatial configuration of these masks. Accordingly, great improvements in data quality, reliability and reproducibility can be achieved, and that, generally without the assistance or presence of a health care provider, which is generally required with previously known systems.

Furthermore, it will be appreciated that different manufacturing techniques and materials may be considered in manufacturing the above and similar masks, for example as described below, without departing from the general scope and nature of the present disclosure. For example, the entire mask may be molded in a single material, or fashioned together from differently molded or otherwise fabricated parts. For example, the outwardly projecting nosepiece of the mask may comprise one part, to be assembled with the frame and face-resting portion of the mask. Alternatively, the frame and nosepiece may be manufactured of a single part, and fitted to the face-resting portion thereafter. As will be further appreciated, more or less parts may be included in different embodiments of these masks, while still providing similar results. For example, the nose piece, or an equivalent variant thereto, could be manufactured to rest directly on the subject's face, without the need for a substantial frame or face resting portions. Alternatively or in addition, different numbers of outwardly projecting limbs (e.g. two, three, four, etc.) or structures may be considered to provide similar results.

In general, the at least one transducer in the above examples, and their equivalents, is responsive to sound and/or airflow for generating a data signal representative of breathing sounds to be used in implementing different embodiments of the below-described methods. For example, in the illustrated embodiment of FIG. 2, two microphones 202 and 204 are provided in the transducer support portion 210, wherein one of these microphones may be predominantly responsive to sound, whereas the other may be predominantly responsive to airflow. For example, the microphone configured to be predominantly responsive to airflow may be more sensitive to air pressure variations then the other. In addition or alternatively, the microphone configured to be predominantly responsive to sound may be covered with a material that is not porous to air. In addition or alternatively, the microphone configured to be predominantly responsive to sound may be oriented away from the subject's nose and mouth so to reduce an air impact on the diaphragm of this microphone produced by the subject's breathing airflow. In other embodiments, a microphone predominantly responsive to airflow may be positioned in the transducer support portion in line with the subject's nose and mouth, while another microphone may be positioned to the side or on the periphery of the mask to thereby reduce an influence of airflow thereon. In some of these embodiments, the recorded sound from the peripheral microphone, or again from the microphone predominantly responsive to sound, may in fact be used to isolate the airflow signal recorded in the nosepiece, by filtering out the sound signal recorded thereby, for example.

In the embodiments of FIGS. 1, 3 and 4, however, a single microphone may alternatively be used to capture both sound and airflow, wherein each signal may be optionally distinguished and at least partially isolated via one or more signal processing techniques, for example, wherein a turbulent signal component (e.g. airflow on microphone diaphragm) could be removed from other acoustic signal components (e.g. snoring). Such techniques could include, but are not limited to adaptive filtering, harmonics to noise ratio, removing harmonics from a sound recording, wavelet filtering, etc.

In each of the above examples, the device may be implemented using a single type of transducer, for example one or more microphones which may in fact be identical. It will be appreciated however that other types of transducers, particularly responsive to airflow, may be considered herein without departing from the general scope and nature of the present disclosure. For example, a pressure sensor or airflow monitor may be used instead of a microphone to yield similar results in capturing an airflow produced by the subject while breathing.

It will be appreciated by the skilled artisan that different types of masks, or other means for recording breath sounds, may be considered herein without departing from the general scope and nature of the present disclosure. Namely, while the above examples provide for one means for acquiring breath sound data in implementing the below-described analysis methods, other means will be readily apparent to the person of ordinary skill in the art and should thus be considered to fall within the context of the present disclosure. For example, different microphone setups may be considered to provide similar effects, such as, but not limited to, positioning a microphone on the lip, the trachea, or on the forehead of the candidate, or again by providing a floating microphone disposed above the candidate's face or head during sleep. These and other variations will be readily apparent to the skilled artisan and therefore intended to fall within the general scope and nature of the present disclosure.

In the above examples, acquired breath sound data is generally communicated to data recording/processing module 120, 220, 320, which may comprise a single self-contained module, or a number of distinct and communicatively coupled or coupleable modules configured to provide complimentary resources in implementing the below-described methods. Namely, the recording/processing module may comprise a distinctly implemented device operatively coupled to one or more breath sound transducers for communication of data acquired thereby via, for example, one or more data communication media such as wires, cables, optical fibres, and the like, and/or one or more wireless data transfer protocols, as would be readily appreciated by one of ordinary skill in the art. A distinct recording module may, however, in accordance with another embodiment, be implemented integrally with the mask, and used to later communicate recorded data, be it raw and/or preprocessed data, to a remote or distinct processing device. As will be appreciated by the skilled artisan, the processing module may further be coupled to, or operated in conjunction with, an external processing and/or interfacing device, such as a local or remote computing device or platform provided for the further processing and/or display of raw and/or processed data, or again for the interactive display of system implementation data, protocols and/or diagnostics tools.

Figure 5:
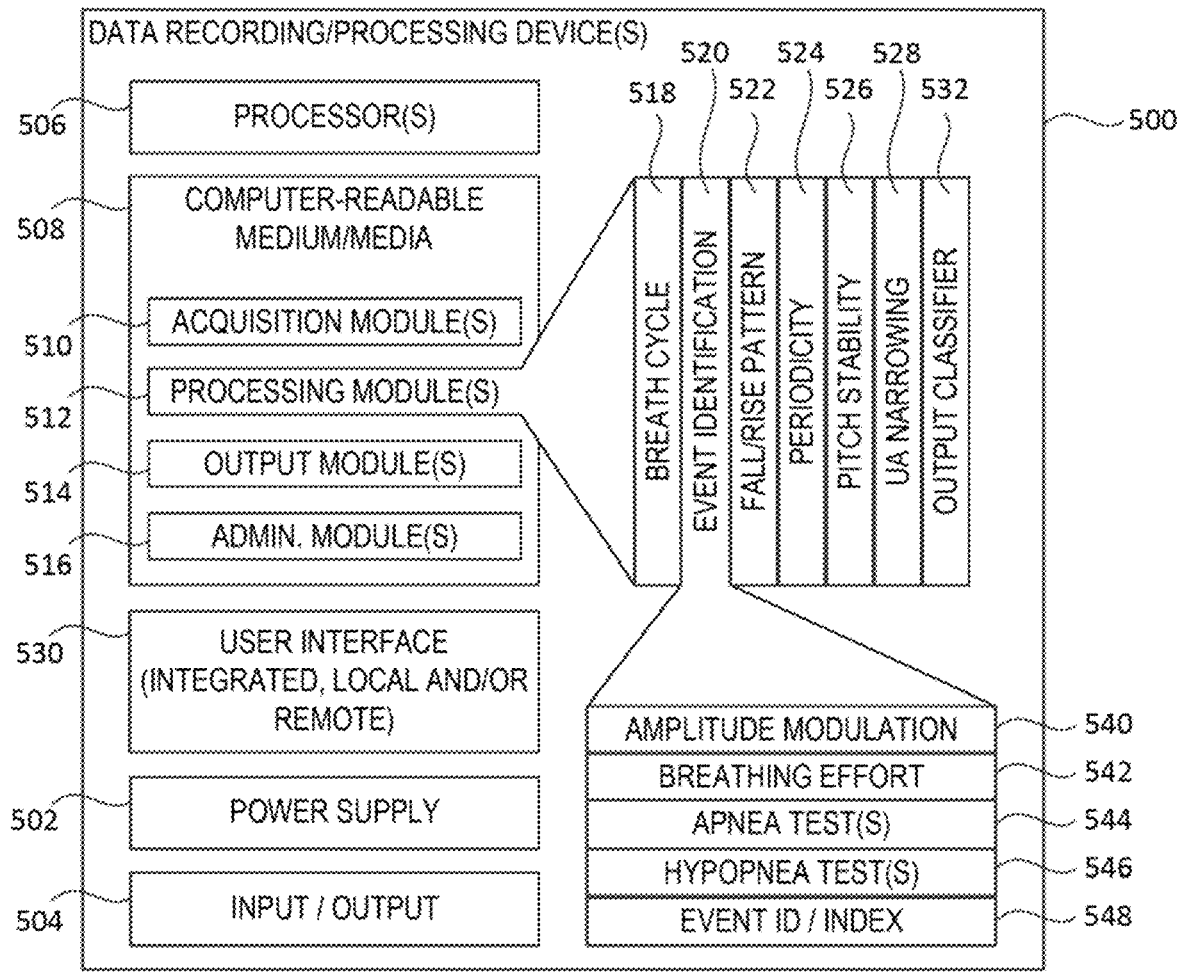
FIG. 5 is a schematic diagram of a breathing sound recording/processing device, for use for example within the context of the system of FIG. 1, in accordance with one embodiment of the invention.

With reference to FIG. 5, the processing module, depicted herein generically as a self-contained recording/processing device 500, generally comprises a power supply 502, such as a battery or other known power source, and various input/output port(s) 504 for the transfer of data, commands, instructions and the like with interactive and/or peripheral devices and/or components (not shown), such as for example, a breath monitoring mask or the like (as shown in FIGS. 1 to 4), external data processing module, display or the like.

The device 500 further comprises one or more computer-readable media 508 having stored thereon statements and instructions, for implementation by one or more processors 506, in automatically implementing various computational tasks with respect to, for example, breath sound data acquisition and processing. Such tasks may include, but are not limited to, the implementation of one or more breathing disorder identification, characterization and/or diagnostic tools implemented on or in conjunction with the device 500. In the illustrative example of FIG. 5, these statements and instructions are represented by various processing submodules and/or subroutines to be called upon by the processors 506 to operate the device in recording and processing breathing sounds in accordance with the various breath disorder identification, characterization and diagnostic methods discussed below. Illustratively, the processing platform will include one or more acquisition module(s) 510 for enabling the acquisition and digitization of breath sounds generated by the candidate while breathing; one or more processing module(s) 512 for processing the acquired data in identifying, characterizing and/or diagnosing a potential breathing disorder; one or more admin. module(s) 516 for receiving as input various processing parameters, thresholds and the like, which may be varied from time to time upon refinement and/or recalibration of the system or based on different user or candidate characteristics; and one or more output module(s) 514 configured to output process results in a useable form, either for further processing, or for immediate consumption (e.g. breath disorder identification, characterization and/or diagnosis results, indicia, and the like). For the purpose of illustration, the processing module(s) 512 in this particular example, and with reference to the processes of FIGS. 6A and 6B, discussed in greater detail below, may include, but are not limited to, a breath cycle identification module 518, e.g. to identify and/or distinguish inspiratory and expiratory breathing phases; an event identification module 520, e.g. to identify, characterize and/or count apneic and/or hypopneic events, and/or to output a value or index (e.g. apnea-hypopnea index—AHI) representative of an overall severity of the disorder; a fall/rise pattern analysis module 522, e.g. to analyze breathing patterns associated with an identified event for further characterization as potentially representative of OSA vs. CSA; a periodicity identification module 524, e.g. to identify periodic sounds such as snoring; a pitch stability module 526, e.g. to further characterize identified periodic sounds as potentially representative of an obstructed airway—OSA; an upper airway (UA) narrowing detection module 528, e.g. to identify UA narrowing, which may be potentially representative of OSA, from recorded aperiodic breath sounds; and an overall classifier 532 for classifying outputs from the multiple processing modules into a singular output, as appropriate.

It will be appreciated that different embodiments may implement different subsets and combinations of the above modules to achieve different results depending on the intended purpose of the device and/or known or suspected candidate conditions. It will be further appreciated by the skilled artisan upon reference to the following description of illustrative embodiments that each of the above-noted processing modules may itself be composed of one or more submodules for the purpose of achieving a desired output or contribution to the overall process. For example, and with reference to the process of FIGS. 8, 12 and 13, the event identification module 520 may further comprise a breath sound amplitude modulation module 540, e.g. to extract an absolute breath sound amplitude profile; a breathing effort extraction module 542, e.g. to identify prospective events based on observed breathing effort variations; apnea/hypopnea test modules 524/526, e.g. to identify prospective events representative of true apneas/hypopneas; and an event identification module 528, e.g. to generate an event identification, overall count and/or severity index. Similarly, while not explicitly illustrated, other processing modules may be equally subdivided into submodules consistent with preset processes to be implemented thereby, for example as described hereinbelow in accordance with different illustrative embodiments of the invention. Clearly, while the above contemplates the provision of a modular processing architecture, other process architectures may be readily applied to the present context, as will be appreciated by the person of ordinary skill in the art, without departing from the general scope and nature of the present disclosure.

The device 500 may further comprise a user interface 530, either integral thereto, or distinctly and/or remotely operated therefrom for the input of data and/or commands (e.g. keyboard, mouse, scroll pad, touch screen, push-buttons, switches, etc.) by an operator thereof, and/or for the presentation of raw, processed and/or diagnostic data with respect to breathing disorder identification, characterization and/or diagnosis (e.g. graphical user interface such as CRT, LCD, LED screen or the like, visual and/or audible signals/alerts/warnings/cues, numerical displays, etc.).

As will be appreciated by those of ordinary skill in the art, additional and/or alternative components operable in conjunction and/or in parallel with the above-described illustrative embodiment of device/module 500 may be considered herein without departing from the general scope and nature of the present disclosure. It will further be appreciated that device/module 500 may equally be implemented as a distinct and dedicated device, such as a dedicated home, clinical or bedside breathing disorder identification, characterization and/or diagnosis device, or again implemented by a multi-purpose device, such as a multi-purpose clinical or bedside device, or again as an application operating on a conventional computing device, such as a laptop or PC, or other personal computing devices such as a PDA, smartphone, or the like.

Furthermore, it will be appreciated that while a single all-encompassing device 500 is schematically depicted herein, various functionalities and features of the device may rather be distributed over multiple devices operatively and/or communicatively coupled to achieve a similar result. For example, in one embodiment, at least part of the functionalities of device 500 will be implemented on a local processing device integral to a self-contained breath monitoring mask, such as depicted by the embodiments of FIGS. 2 to 4. In such embodiments, the power supply, such as batteries, may be integral to the mask as well, thus providing a self-contained unit to be worn by the candidate during sleep without interference from cumbersome wires or wire harnesses. In such embodiments, the integrated processing device may be operatively coupled to the mask's one or more transducers, e.g. via one or more internal wires or a wireless link, so to provide self-contained recordal of breathing sounds during use.

The integrated device may be configured to record the raw data for subsequent transfer and processing, or may be preconfigured to implement various preprocessing and/or processing steps locally. For example, the local processing device may preprocess the recorded data in real-time to facilitate subsequent transfer, such as by digitizing the data, applying certain filters and/or amplifiers, and the like. In such embodiments, breathing sound data may be transferred in real-time, for example where the integrated device is operatively coupled to a wireless transceiver or the like, or again transferred in batches, for example, at the end of each sleep session. In the latter case, the integrated device may provide a wired or pluggable communication port for coupling to a computing device, either for immediate processing thereby, or again for communication of the recorded data to a remote processing platform (e.g. operated by a diagnostic or medical center). Alternatively, the recorded data may be stored by the integrated device on a removable medium, to be transferred to an appropriate reader for download and processing.

In other embodiments, further processing may be implemented locally on the self-contained device, with appropriate output available so to provide the user immediate access to at least some of the processed results. For example, and as will be discussed in greater detail below, preliminary results may be rendered available to the user for immediate consumption, such as an indication as to the likelihood that the candidate suffers from sleep apnea, a preliminary indication as to the severity thereof, and/or a full diagnostic of the user's condition, to name a few.

Breathing disorders are traditionally monitored and diagnosed using data acquired at sleep centers, where subjects are fitted with a number of electrodes and other potentially invasive monitoring devices, and monitored while they sleep. Clearly, as the subject is both required to sleep in a foreign setting with a number of relatively invasive and obtrusive monitoring devices attached to them, the data collected can often be misleading, if the subject even ever manages to get any sleep to produce relevant data.

Furthermore, known respiratory diagnostic systems generally require the acquisition of multiple sensory data streams to produce workable results that may include breath sounds, airflow, chest movements, esophageal pressure, heart rate, etc. Similarly, known portable monitoring devices proposed for the diagnosis of sleep apnea generally require subjects to adequately position and attach several wired electrodes responsive to a number of different biological parameters, such as listed above, which generally reduces the comfort and compliance of subjects and increases chances of detachment and/or displacement of the electrodes. Given that portable sleep apnea monitors are used in the absence of an attending health care professional, inaccurate placement or displacement of electrodes cannot be easily detected until the data is transferred to the health center.

In comparison, the provision of a portable mask for use in recording breathing sounds useable in the above-described system and below-described methods may provide a number of advantages over known techniques, including, but not limited to, patient comfort, ease of use, processing from single source data, etc.

In one exemplary embodiment, the recorded data is stored, and optionally encrypted on a removable data storage device, such as an SD card or the like. For example, analog data acquired by the one or more transducers can be locally pre-amplified, converted into digital data and stored in the removable memory device. The stored data can then either be uploaded from the memory card to a local computing device (e.g. laptop, desktop, palmtop, smartphone, etc.) for transmittal to a remotely located diagnostic center via one or more wired and/or wireless communication networks, or physically shipped or delivered to the remotely located diagnostic center for processing.

It will be appreciated that different types of data transfer and communication techniques may be implemented within the present context without departing from the general scope and nature of the present disclosure. For example, while the above example contemplates the use of a digital recording device having a removable data storage medium, such as a memory card of the like, alternative techniques may also be considered. For example, the recording device may rather include a wireless communication interface wherein data integrally recorded thereon can be wirelessly uploaded to a computing device in close proximity thereto. For example, Wi-Fi or Bluetooth applications may be leveraged in transferring the data for downstream use. Alternatively, the device may include a communication port wherein recorded data may be selectively uploaded via a removable communication cable, such as a USB cable or the like. In yet another example, the recording device itself may be removably coupled to the mask and provided with a direct communication interface, such as a USB port or the like for direct coupling to an external computing device. These and other such examples are well within the realm of the present disclosure and therefore, should not, nor should their equivalents, be considered to extend beyond the scope of the present disclosure.

Figure 6A:
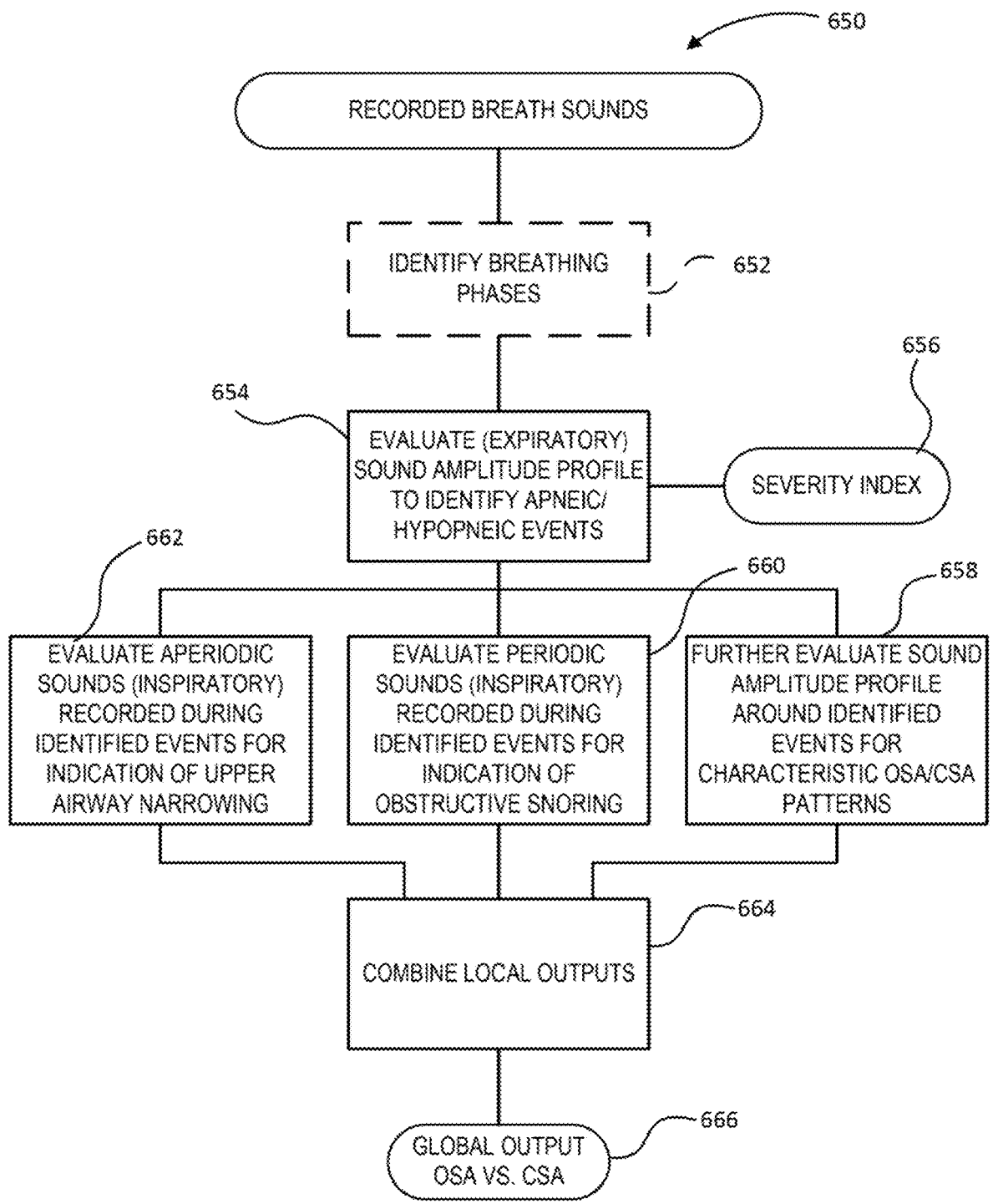
FIG. 6A is a high level flow diagram of a sleep apnea identification, characterization and diagnosis method, in accordance with one embodiment of the invention.

With reference to FIG. 6A, and in accordance with one embodiment, a high level process 650 for identifying, characterizing and diagnosing sleep apnea will now be described. It should be noted that, while process 650 may, in accordance with one embodiment, ultimately allow for the qualification and/or quantification of a subject's breathing disorder, be it in classifying observed breathing irregularities as indicative of OSA or CSA, or again in outputting a value or index representative of the severity of the subject's condition, the various sub-processes used in this classification may, in and of themselves, present usable results in identifying, characterizing and/or diagnosing a subject's breathing disorders, and that, without necessarily seeking to achieve the ultimate results considered by the overall process 650. Accordingly, while the following describes an overall breath disorder identification, quantification and classification process, it will be appreciated that the scope of this disclosure should not be so limited, but rather, should be interpreted to include the various sub-process combinations that may lead, in and of themselves, to respective usable results in identifying and characterizing a subject's condition.

In this example, breath sound data is first acquired at step 652 via a mask having one or more transducers, such as described above with reference to FIGS. 1 to 4, operatively coupled to an integral, local and/or remote recording/processing device or module for processing the recorded breath sounds, for example as described above with reference to FIG. 5. In a first (optional) step 652, breathing cycles are identified whereby timing data associated with successive inspiratory and expiratory phases can be extracted for use in segmenting the recorded data downstream to improve processing efficiency. In the exemplary embodiments described in greater detail below with reference to FIGS. 8 to 19 for calculating, as introduced by steps 654 and 656, an apnea/hypopnea severity index (AHI), expiration phases, in particular, may be isolated and used to improve results. On the other hand, inspiration phase timing can be used, for example at step 662, to facilitate implementation of the exemplary upper airway narrowing detection processes described in greater detail below with reference to FIGS. 28 to 32. Note that, while depicted in this example and described in greater detail below, this step is not necessarily required as other approaches may be implemented to identify data segments of interest. For example, the isolation of periodic breath sounds, which are predominantly associated with inspiration, can be automatically achieved by the frequency analysis subroutine used in the below-described example for further processing of such breath sound segments without prior extraction and input of breathing phase timing.

At step 654, the amplitude profile of the digitized recording, in this embodiment focused on expiratory sound amplitudes, is automatically scanned to identify events of interest, namely events over time possibly representative of apneic or hypopneic events. Different exemplary event identification tests applicable in this context are discussed in greater detail below with reference to FIGS. 8, and 11 to 15. Upon identifying one or more such events, the data may already be classified as indicative of a subject suffering from sleep apnea. To further the characterization of the subject's condition, a severity index may be calculated, for example as a function of a number of events per preset time interval, such as an Apnea-Hypopnea Index (AHI), commonly utilized in the art to characterize a severity of a subject's condition. For example, in one embodiment, identification of at least five (5) or ten (10) apneic and/or hypopneic events per hour may be characterized as representative of a candidate having at least mild apnea, whereas higher counts may be subdivided into different classes such as high or severe cases of apnea. Based on this result, a tested candidate may receive treatment or recommendations, or again be directed to further testing, screening and/or diagnostics.

Furthermore, or alternatively, the timing data of each event of interest identified at step 654 may be used for further processing to further characterize the subject's condition. For example, various tests and analyses can be implemented to independently or jointly characterize the subject's identified condition as CSA or OSA. For example, at step 658, the amplitude variation pattern of or around an identified event can be further analyzed by the device to characterize the event as indicative of OSA or CSA. Namely, by previously identifying amplitude variation patterns typically associated with CSA and OSA, respectively, the system can be configured to automatically assess the amplitude pattern at or around a given event in comparison with such previously identified patterns to automatically classify the event as indicative of CSA or OSA. As will be described in the example below with reference to FIGS. 6B and 19 to 22, the fall rise pattern associated with an identified event can provide a reliable identifier of the subject's condition. In this particular example, for instance, gradual falling and rising edges (decrescendo/crescendo pattern) in the event amplitude profile are generally indicative of CSA, whereas a gradual fall and an abrupt rise in the event amplitude profile are generally indicative of OSA.

To increase the reliability of the system, or again to accommodate data sets or events for which amplitude profiles are not sufficiently consistent with preset patterns, complimentary tests can also be implemented by the system on the recorded breath sound data to contribute to the characterization of the subject's condition. Alternatively, these tests may be implemented in isolation to provide usable results, in accordance with some embodiments of the invention. For example, step 660 provides for the automated analysis of periodic (e.g. expiratory) sounds generated during breathing. As will be discussed in greater detail below with reference to FIGS. 6B, and 23 to 26, relatively stable periodic sounds, e.g. those exhibiting a relatively stable pitch and/or frequency signature, may be more readily associated with CSA, whereas relatively unstable periodic sounds may be more readily associated with OSA. In this example, sound periodicity and stability analyses are generally implemented in respect of sound data acquired during and/or around identified events of interest, and in particular, with respect to inspiratory sounds. It will be understood, however, that greater data segments, or the entire data set, may be so analyzed to provide greater breadth of analysis. Namely, in one example, the entire recording may be analyzed for periodicity, and those segments so identified further processed for pitch stability. Alternatively, only periodic segments identified during and/or around identified events of interest may be considered in this step. Results as to periodic sound stability can then be used downstream, alone or in combination, to further characterize the subject's condition.

As in step 660, step 662 provides for another approach to independently or jointly participate in the characterization of the subject's condition. For example, step 662 provides for the automated analysis of aperiodic (e.g. inspiratory) sounds generated during breathing, whereby a predefined signature of such sounds can be compared to previously classified signatures in classifying these sounds as more readily indicative of OSA vs. CSA. For example, and as will be described in greater detail below with reference to FIGS. 6B, and 28 to 32, a correlation between upper airway (UA) narrowing and aperiodic sound signatures can be defined, whereby aperiodic sounds indicative of UA narrowing may be more readily associated with OSA, as opposed to aperiodic sounds indicative of an open UA, which are more readily associated with CSA. Accordingly, upon analyzing aperiodic sound signatures in comparison with predefined signatures previously classified as a function of UA narrowing, UA narrowing during events or interest, or again during other periods within the recorded data set, may be identified and used downstream, alone or in combination, to further characterize the subject's condition.

In this example, local outputs from steps 658, 660 and 662, when applied, can be combined at step 664 to provide a global output indication 666 as to the overall result of the process 600. As will be discussed in greater detail below with reference to FIG. 33, in some embodiments, a global output may consist of an overall classification or indication as to the candidate's most likely condition (e.g. OSA or CSA) along with an indication as to a severity of the reported condition (e.g. AHI). In other embodiments, a probability or likelihood may be associated with each condition for further interpretation or in evaluating an overall accuracy or reliability of the process in a particular case. These and other such permutations should become apparent to the person of ordinary skill in the art upon reference to the following description of exemplary embodiments. As will be further described below, different data classifiers, ranging from basic voting or weighted voting algorithms, to more complex classification systems, may be implemented to yield consistent and reliable results, depending on the intended complexity and accuracy of the intended product, for example.

Figure 6B:
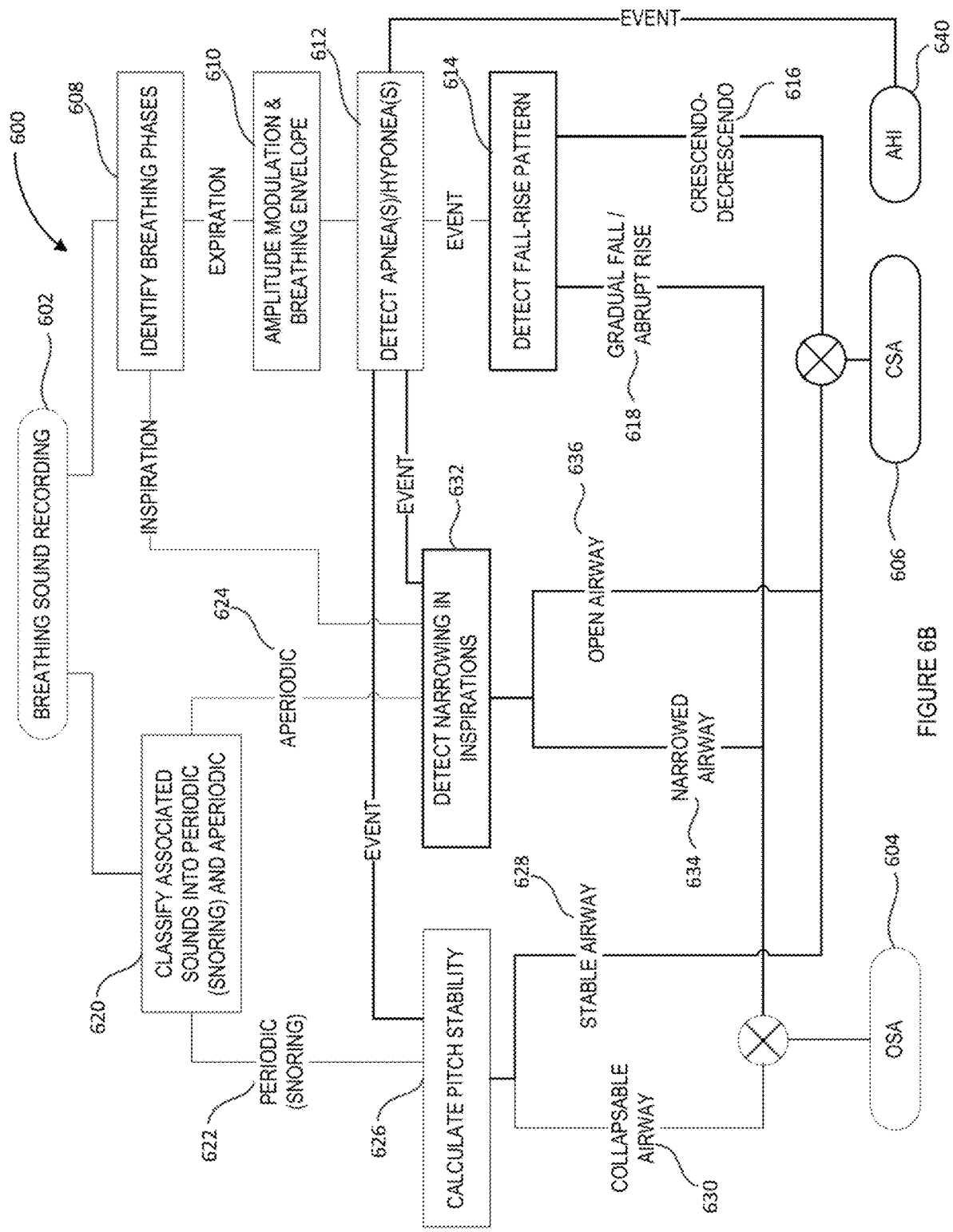
FIG. 6B is a detailed flow diagram of an exemplary sleep apnea identification, characterization and diagnosis method, in accordance with one embodiment of the invention.

With reference now to FIG. 6B, and in accordance with one embodiment, a more detailed process 600 for identifying, characterizing and diagnosing sleep apnea in a subject via breath sound analysis, will be described. In this example, breath sound data is first acquired at step 602 via a mask having one or more transducers, such as described above, operatively coupled to a recording/processing device or module for processing. From this recorded data, various processing steps are implemented, as depicted by process 600, to ultimately classify the recorded data as representative of a healthy subject (not shown), a subject exhibiting symptoms of OSA (604), or of a subject exhibiting CSA (606), and in some embodiments, to further provide an indication of a severity of these conditions, for example via output of a calculated Apnea-Hypopnea Index (AHI) 640. Again, as noted above, it will be appreciated that, while process 600 may, in accordance with one embodiment, ultimately allow the classification of a subject's breathing as indicative of OSA or CSA, the various sub-processes used in this classification may, in and of themselves, present usable results in identifying, characterizing and/or diagnosing a subject's breathing disorders, and that, without necessarily seeking to achieve the ultimate results considered by the overall process 600. Accordingly, while the following describes an overall breath disorder diagnostic process, it will be appreciated that the scope of this disclosure should not be so limited, but rather, should be interpreted to include the various sub-process combinations that may lead, in and of themselves, to respective usable results in identifying and characterizing a subject's condition.

For the sake of clarity, the overall process 600 will be described generally, with exemplary implementations of each sub-process described in greater detail below, as appropriate.

Breathing Phase Identification

In this particular example, the breathing sound recording is analyzed at step 608 to automatically identify breathing phases, for example to identify timing data representative of each inspiration and expiration cycle of the subject's breathing track, which timing data can then be used, as needed, in subsequent processing steps. In this particular example, breathing cycle identification is automatically implemented by the method described in International Application Publication No. WO 2010/054481, the entire contents of which are hereby incorporated herein by reference.

Figure 7A:
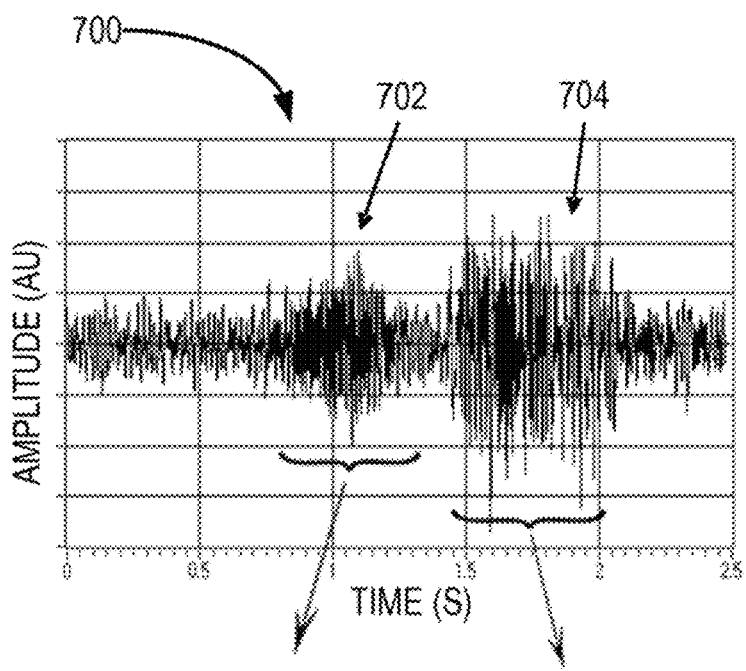
Figure 7B:
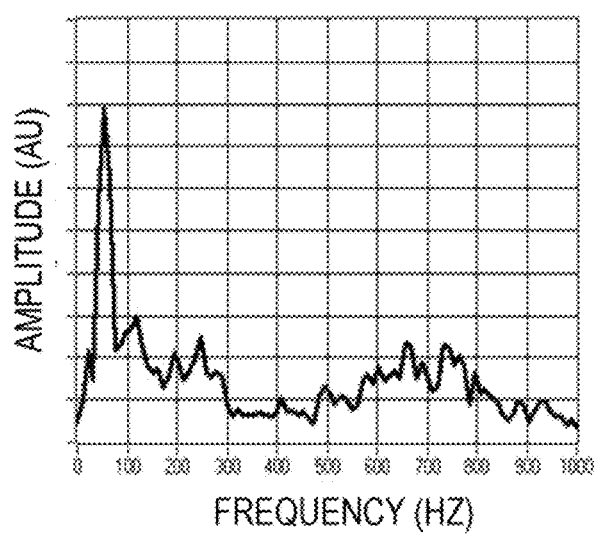
FIGS. 7B and 7C are exemplary FFT spectra for respective time segments of the inspiration phase and expiration phase of FIG. 7A, in accordance with one embodiment of the invention.
Figure 7C:
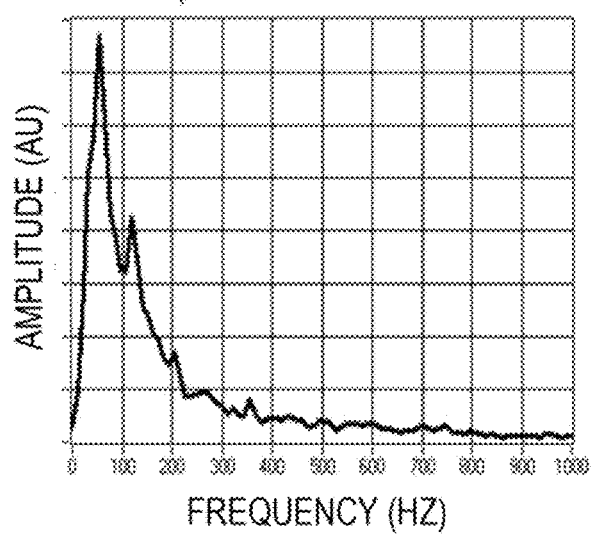

Briefly, an acoustic data waveform plot, for example as shown in the waveform versus time plot 700 of FIG. 7A for a single breath showing both an inspiration phase 702 and an expiration phase 704, can be processed using this method to automatically extract therefrom an indication as to each inspiratory and expiratory breathing cycle. In particular, a spectral analysis of the acoustic data, for example as shown by the exemplary FFT spectra of FIGS. 7B and 7C for respective time segments of the inspiration phase 702 and expiration phase 704 of FIG. 7A, can be used to achieve this result. As can be seen in FIG. 7B in respect of the inspiration phase, a sharp narrow band of harmonics is identified below 200 Hz and another peak is again identified above 400 Hz. Comparatively, the expiratory spectrum, as shown in FIG. 7C, forms a wider band that spans frequencies up to 500 Hz whose power drops off rapidly above this frequency.

Using this observed distinction between spectral compositions for inspiration and expiration data, appropriate frequency-domain metrics can be formulated to automatically distinguish the two types of phases. For example, in this particular embodiment, the bands ratio (BR) of summed frequency magnitudes between 400 to 1000 Hz, to frequency magnitudes between 10 to 400 Hz can be calculated for successive time segments of the recorded data to automatically identify inspiratory and expiratory phases, where higher BR values represent inspiration phases as compared to expiration phases. The following equation provides an exemplary approach to calculating the BR for a given time segment:

$$BR = \sum_{400 Hz}^{1000 Hz} FFT(f) \bigg/ \sum_{10 Hz}^{400 Hz} FFT(f)$$

where the numerator represents the sum of FFT higher frequency magnitude bins which lie between 400 and 1000 Hz, and the denominator represents the sum of FFT lower frequency magnitude bins which lie between 10 and 400 Hz, for example. Upon setting appropriate BR values for inspiration and expiration cycles, determined generally or with respect to a particular subject or class of subjects, automated breathing cycle identification can be implemented.

The person of ordinary skill in the art will appreciate that while the above describes one example of an automated approach to breathing cycle identification via breath sound analysis, other techniques, not necessarily limited to breathing sound analyses, may also be considered herein to achieve a similar effect, and that, without departing from the general scope and nature of the present disclosure. For example, other automated techniques achieved via the capture and processing of complimentary data, such as via Respiratory Inductance Plethysmography (RIP), (Respitrace Ambulatory Monitoring Inc., White Plains, N.Y., USA), which provides thoracoabdominal displacement data representative of changes of tidal volume during respiration, can also or alternatively be used to compliment further processing. Alternatively, visual identification of breathing phases may be implemented by a trained technician, albeit at the expense of some system automation.

Apnea/Hypopnea Detection

As shown in FIG. 6B, and in accordance with one embodiment, expiratory data may be used at steps 610 and 612 to detect, count and ultimately contribute to the characterization of a subject's manifested apneas/hypopneas. As will be described below, while expiratory data is predominantly used to achieve the intended results of this sub-process, inspiratory data need not necessarily be extracted. In the context of the overall process 600, where breathing cycle differentiation is readily accessible, such information may nonetheless be used to refine subsequent process steps.

In particular, steps 610 and 612 provide for the detection and identification of distinct apneic and hypopneic events for the purpose of characterizing the subject's breathing disorder(s) and providing adequate treatment therefor.

Figure 8:
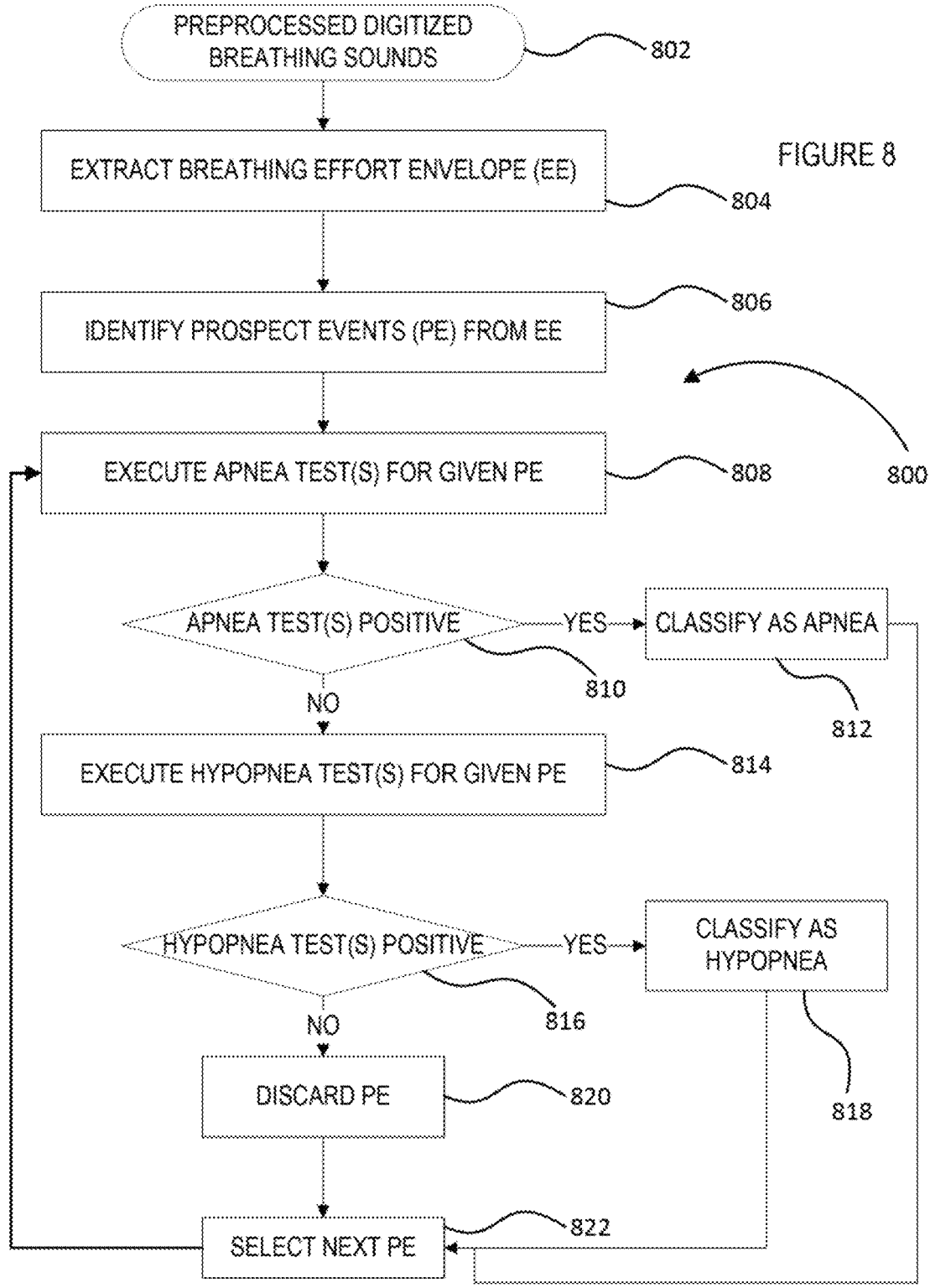
FIG. 8 is a high level flowchart of a method for identifying apneas and hypopneas from digitized breathing sounds, in accordance with one embodiment of the invention.
Figure 9:
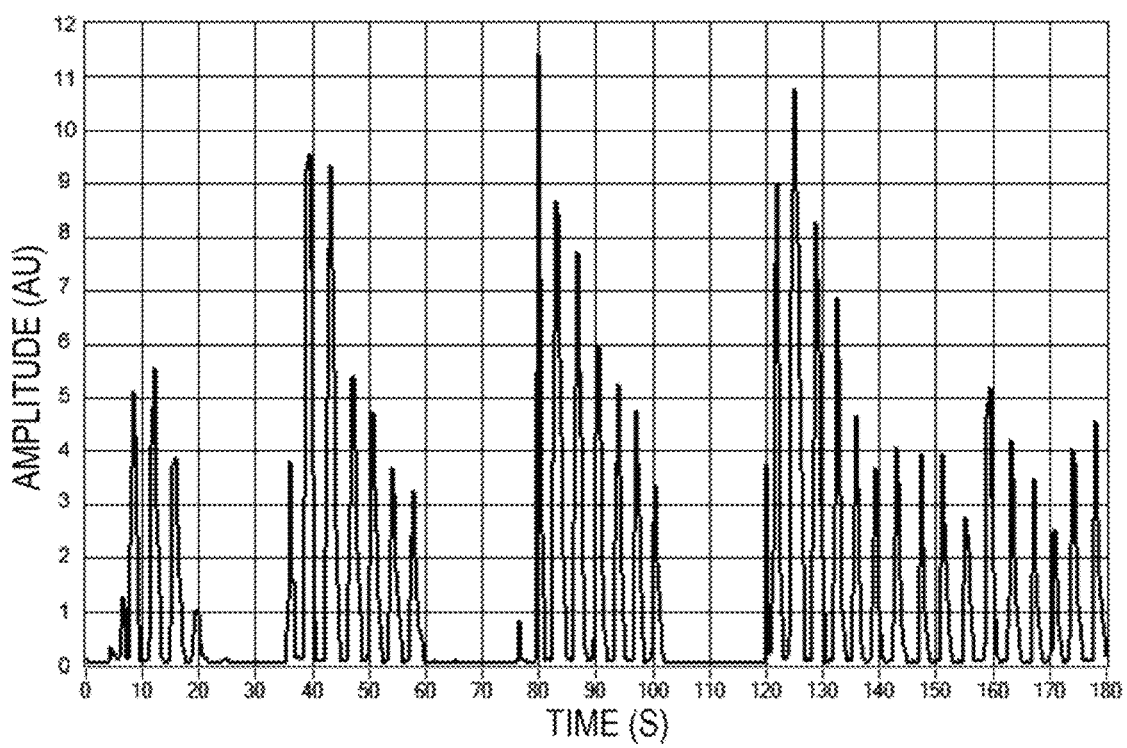
FIG. 9 is a plot of exemplary ventilation breathing sounds and apneic periods, represented by a train of digitized signal peaks, in accordance with one embodiment of the invention.

With reference now to FIG. 8, an example of a sub-process implemented in the context of steps 610 and 612 of FIG. 6B, will now be described. In particular, this example provides one embodiment of an apnea and hypopnea detection method based on a recording of breathing sounds. In general terms, the method 800 is configured to automatically evaluate or recognize patterns in breathing sound data, which in one example described below, has been preprocessed to allow for digitization, outlier removal and normalization. For example, and as will be described in greater detail below, the raw breathing sound recording (e.g. see plot 130 of FIG. 1), can be digitized and the breathing envelope (BE) of each breath identified, for example as seen in FIG. 9 showing a series of breaths and apnea cycles within a 3 minute recording.

As will also be further described below, the digitized train of peaks obtained through initial preprocessing, and as shown in FIG. 10A, may be further adjusted to remove outliner peaks whereby sharp spikes associated with unwanted sounds (such as coughs/snorting) can be removed (e.g. see sharp spikes of FIG. 10A removed in FIG. 10B). To facilitate evaluation of the resulting train of peaks, the data may be further normalized, for example via a segment-based normalization process such as an adaptive segmentation process, thus providing the preprocessed train of breath-related peaks shown in FIG. 10C. As will be appreciated by the skilled artisan, other preprocessing approaches may be applied to raw breathing sound data in order to ready this data for processing in accordance with the herein described apnea and/or hypopnea detection methods, and that, without departing from the general scope and nature of the present disclosure.

Figure 11:
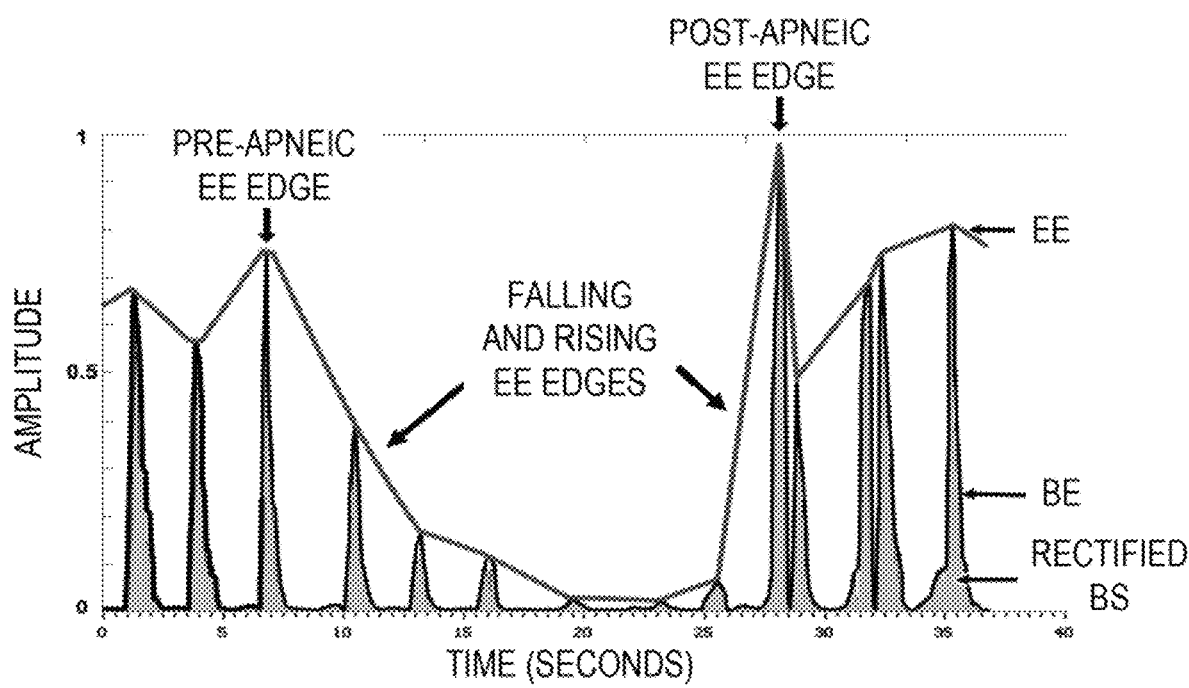
FIG. 11 is an exemplary plot of an identified prospect event (PE) showing relation between rectified digitized breathing sounds (BS) and a breathing envelope (BE) thereof, as well as an extracted breathing effort envelope (EE) taken therefrom and its various components, in accordance with one embodiment of the invention.

From the digitized breathing sound recording, shown as step 802 in FIG. 8 and which may be preprocessed in one embodiment in accordance with the above or other data preprocessing techniques, a breathing effort envelope (EE) is extracted (step 804), for example, as shown in FIG. 11, from which distinct apneic and/or hypopneic events may be identified, in accordance with different embodiments of the invention. The term "breathing effort" is used herein for the sake of illustration, and will be understood by the skilled artisan to represent, in accordance with different embodiments of the invention, a breath-to-breath breathing amplitude profile or variation over time, indicative of a breathing depth for example (e.g. deep breathing vs. shallow breathing), not to be confused with the depth criteria discussed below in identifying true apneas and/or hypopneas.

In one embodiment, prospect events (PE) are first identified in the EE at step 806, which PEs may then each be further evaluated for identification as a true apneic or hypopneic event. An example of a PE is shown in FIG. 11, wherein a significant drop in the EE may be automatically identified, in accordance with one embodiment, and retained as a PE for further evaluation.

For each PE, one or more apnea-specific tests are executed at step 808. Upon a given PE satisfying the requirements of this/these test(s) at step 810, this PE is automatically classified as a true apnea at step 812, which classification may later be used for further processing, or again in obtaining a count of total apneas within a given period or sleep cycle, for example.

Upon a given PE failing at least one of the requirements of the apnea-specific test(s) at step 810, one or more hypopnea-specific tests may then be executed at step 814 to evaluate whether this particular event is rather indicative of a hypopnea. Upon this PE satisfying the requirements of this/these hypopnea test(s) at step 816, this PE is automatically classified as a true hypopnea at step 818, which classification may later be used for further processing, or again in obtaining a count of total apneas within a given period or sleep cycle, for example. Otherwise, the PE is discarded at step 820 and the process repeated for the next PE at step 822. It will be appreciated that each PE may be processed sequentially or in parallel, and that, either for apnea and hypopnea consecutively for each PE, or distinctly for all PEs as a group.

Figure 14A:
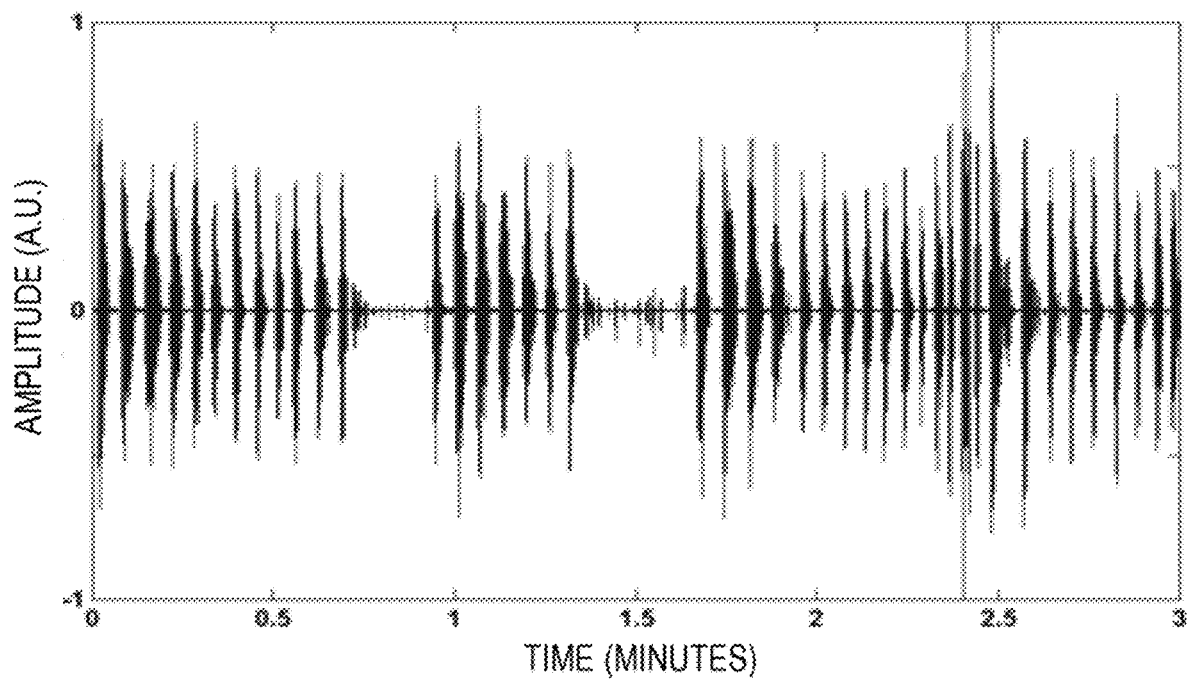
FIGS. 14A and 14B are plots of a three minute segment of sample breath sound data showing raw waveform and envelope profile data respectively.
Figure 14B:
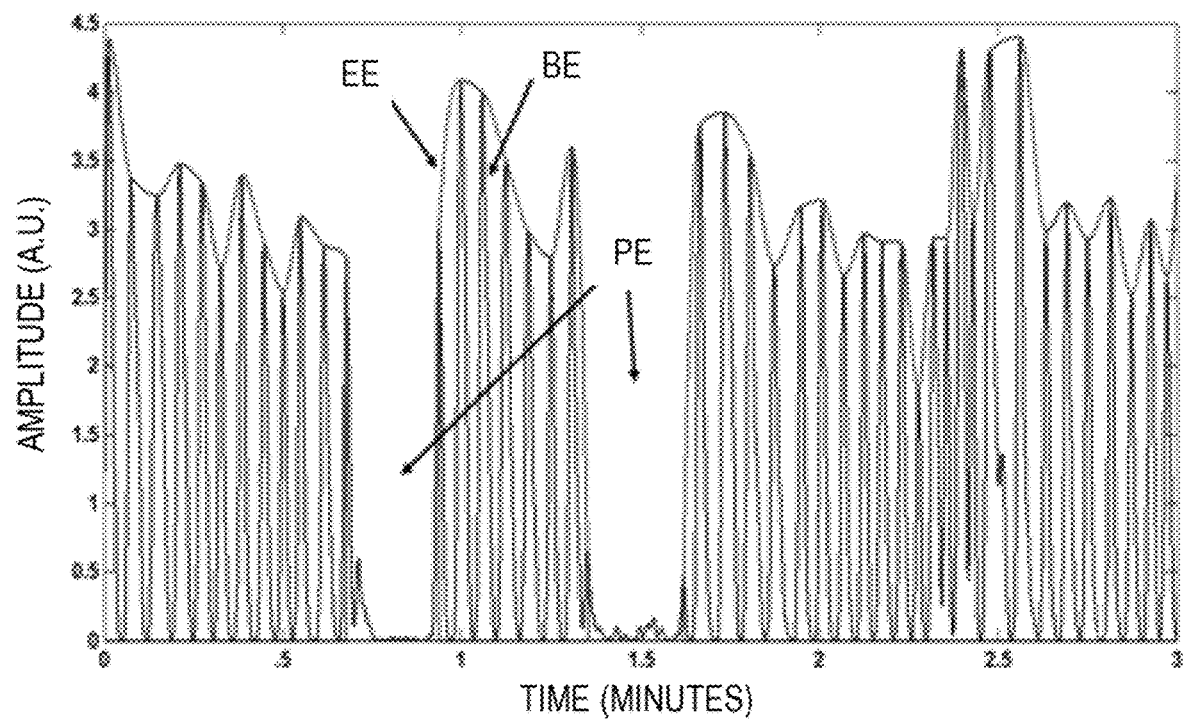

To further illustrate the above-introduced notions, and in accordance with a specific example, FIG. 14A provides an example of a three-minute segment of a raw acoustic signal waveform, acquired as described above, whereas FIG. 14B provides a plot of the breathing envelope (BE) and effort envelope (EE) for this segment emphasizing two PEs automatically identifiable from the extracted EE. As illustrated in these Figures, the raw acoustic signal acquired is efficiently converted into waveforms or profiles representative of the general breath sound amplitude. As noted above, adaptive segmentation and normalization techniques were used to preprocess the data, whereby transient outliers (e.g. coughs and snorting) and non-breathing components from the acoustic signal were excluded prior to generating the signal envelopes depicted in FIG. 14B. Namely, FIG. 14B depicts the envelope of individual breaths (BE), which is formed in this example by the summation of absolute values of signal points within 500 ms long moving windows. It consists of a train of peaks each representing a breathing cycle proportional to its amplitude. FIG. 14B also depicts the breathing effort envelope (EE) extracted therefrom, which effectively traces the overall changes or profile in the acoustic waveform from which respective apneas and/or hypopneas can be automatically identified. Namely, BE maxima are interpolated, and with outliers removed, the EE is normalized to establish a uniform baseline from which individual apneas and/or hypopneas can be automatically identified.

Figure 12:
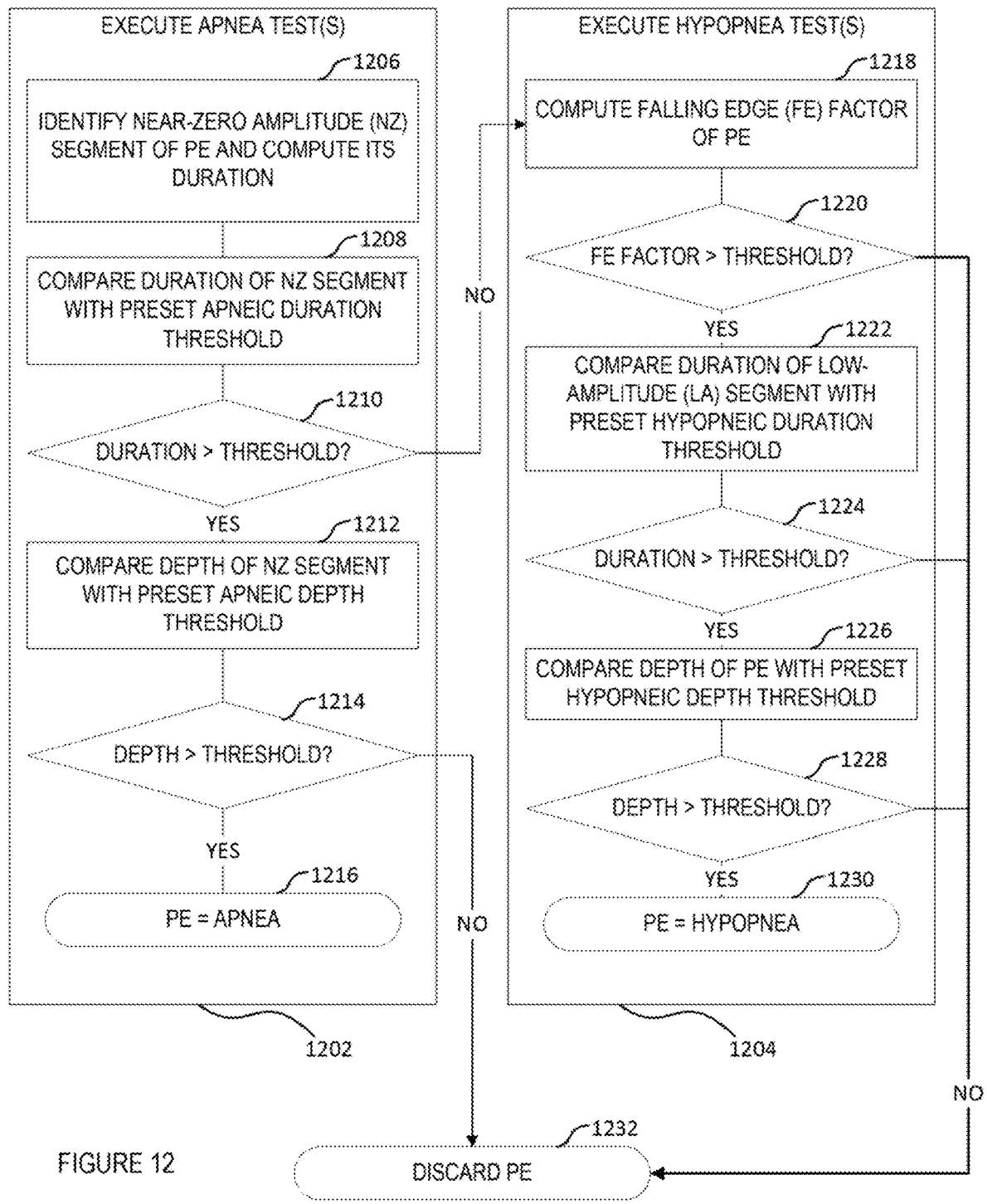
FIG. 12 is a flowchart of illustrative apnea and hypopnea tests executed within the context of the method of FIG. 8, in accordance with one embodiment of the invention.
Figure 15A:
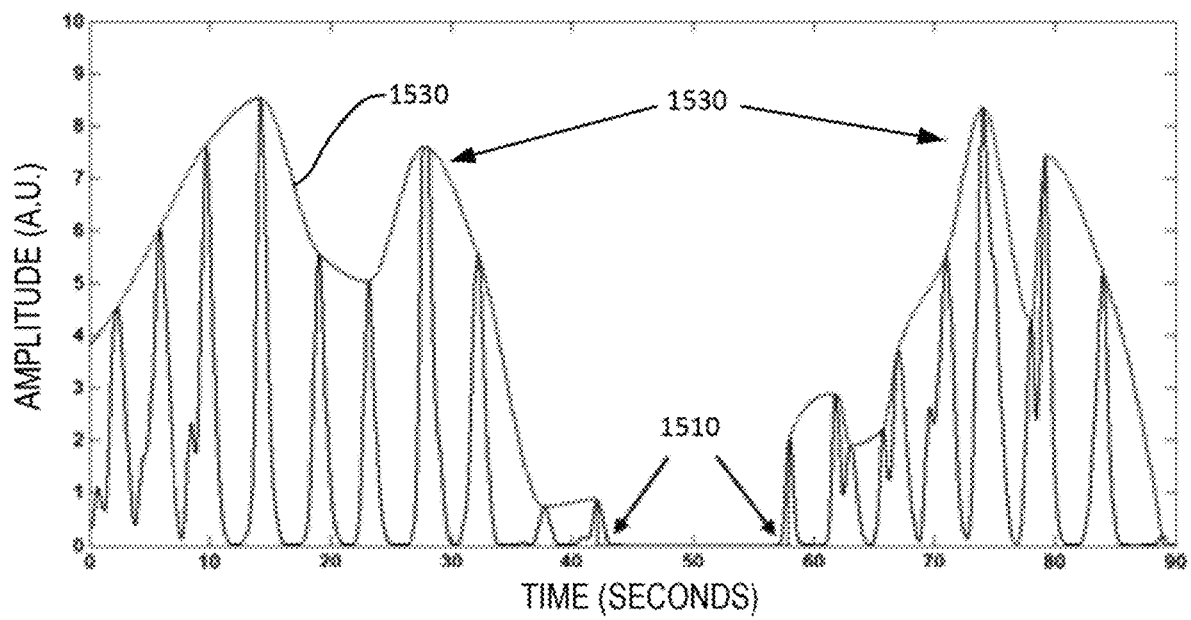
FIGS. 15A and 15B are plots of illustrative envelope profile data for an apneic and a hypopneic event, respectively.

FIG. 12 provides, in accordance with one illustrative embodiment, an example of particular automated apnea-specific 1202 and hypopnea-specific 1204 data evaluation methods, to be considered in the context of the method shown in FIG. 8. In this example, the apnea-specific tests are first executed, consisting of the following evaluations. First, the PE is evaluated at step 1206 to identify a near-zero amplitude segment, consistent with apnea. The duration of this non-zero segment is then computed and compared at step 1208 with a preset apneic event duration threshold. If the computed duration is greater than this threshold, determined at step 1210, the process proceeds to the next step 1212 of evaluating the depth of the near-zero segment relative to surrounding data, and comparing this depth with a preset apneic event depth threshold (e.g. an apnea specific minimum depth threshold). Upon the depth being identified at step 1214 as greater than the preset threshold therefor, the PE is classified as a true apnea at step 1216. FIG. 15A provides an example of a PE satisfying both apnea-specific criteria, whereby the duration of the substantially flat segment 1510 identified from the EE 1520, and the depth thereof in comparison with surrounding data (i.e. peaks 1530 delineating PE), satisfy preset thresholds therefor.

Figure 15B:
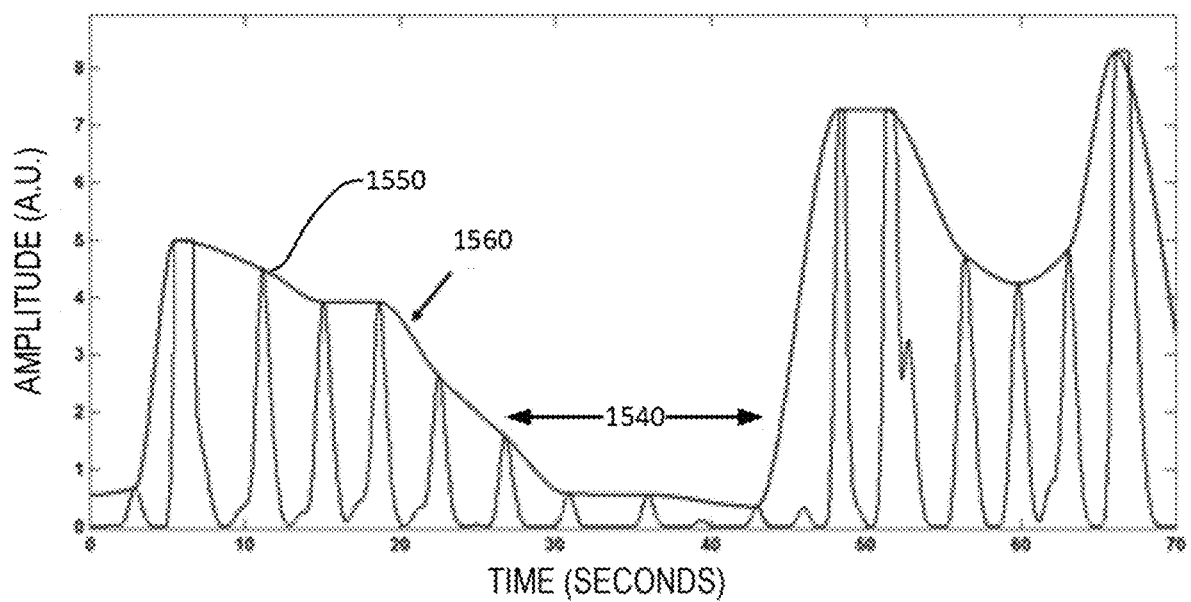
Figure 16:
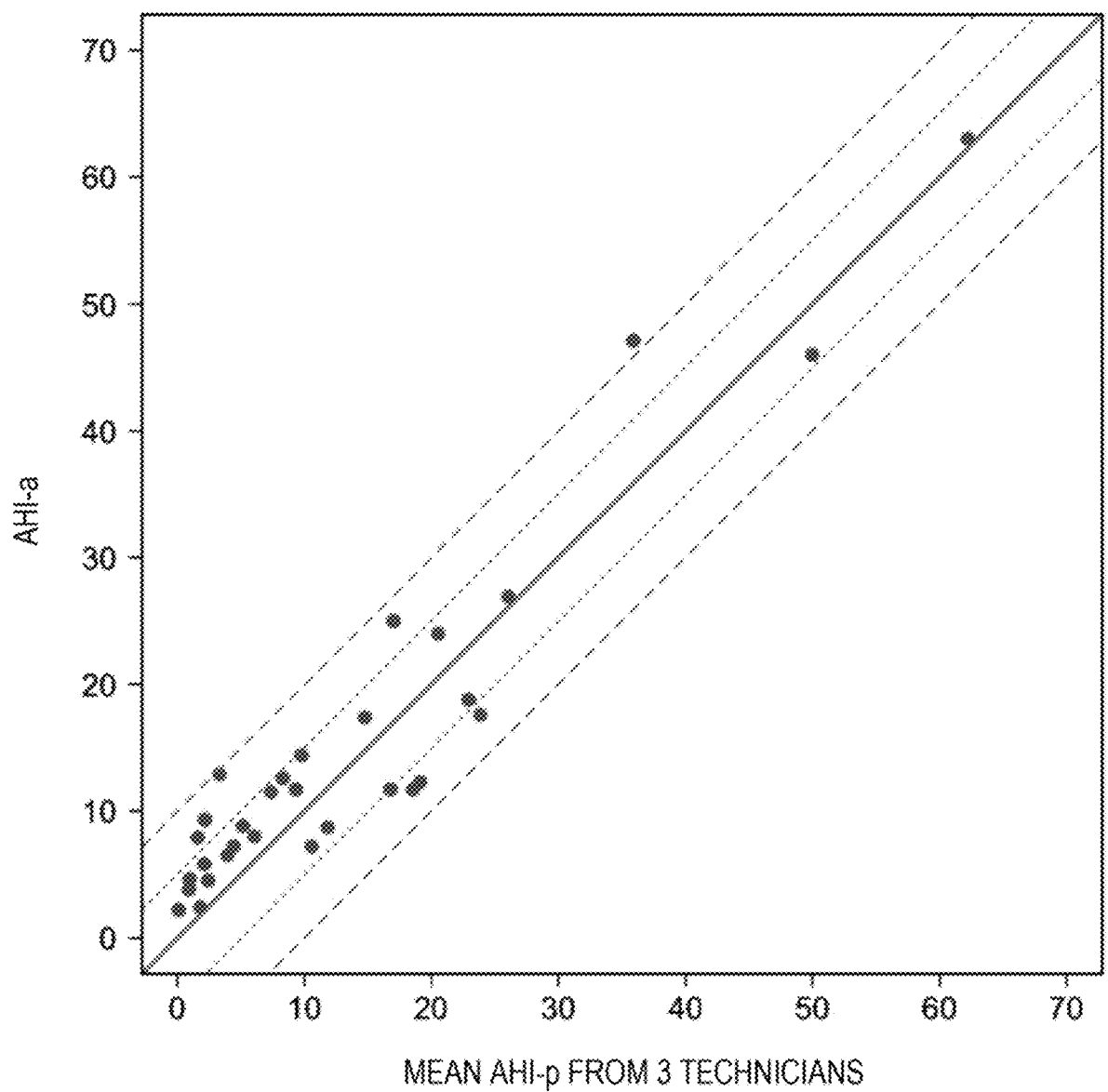
FIG. 16 is a plot depicting high level of agreement between Apnea-Hypopnea Index (AHI) as achieved using a method according to one embodiment of the invention (AHI-a), and AHI as measured by practitioners using a conventional PSG method (AHI-p)

On the other hand, upon the PE data failing at least one of the apnea-specific tests (steps 1210/1214), the process may be redirected to execution of distinct hypopnea-specific tests to rather qualify if the PE is indicative of a hypopnea event. In this example, however, where the PE passes the apnea duration test 1212 but fails the apnea depth test 1214, the PE is automatically discarded (1232) without proceeding to the hypopnea detection subroutine 1204. Where the PE first fails the apnea duration test 1212, the PE is evaluated at step 1218 to compute a falling edge factor thereof, which is generally indicative of a rate of amplitude decrease over time (e.g. decreasing gradient) for the selected PE (see FIG. 11). Upon the falling edge factor exceeding a preset threshold therefor, as determined at step 1220 (e.g. differentiating the dip from what may otherwise be representative of a comparatively healthy breathing cycle variation), a duration of a low-amplitude segment of the PE is computed (e.g. effective duration of the EE dip) and compared at step 1222 to a preset threshold therefor. Upon the computed duration exceeding the prescribed threshold, as determined at step 1224, a depth of the low-amplitude segment is then calculated and again compared at step 1226 with a preset requirement for consistency with a hypopneic event (e.g. a minimum hypopnea-specific depth threshold set shallower than the above noted minimum apnea-specific depth threshold). Upon satisfying each of these requirements, as determined at step 1228, the PE is classified as a true hypopnea at step 1230, otherwise, upon the PE failing any of these requirements, the PE is discarded at step 1232. FIG. 15B provides an example of a PE satisfying all hypopnea-specific criteria, whereby the characteristics of the low-amplitude segment 1540 identified from the EE 1550, and that of the falling edge 1560, satisfy preset thresholds therefor.

Figure 13:
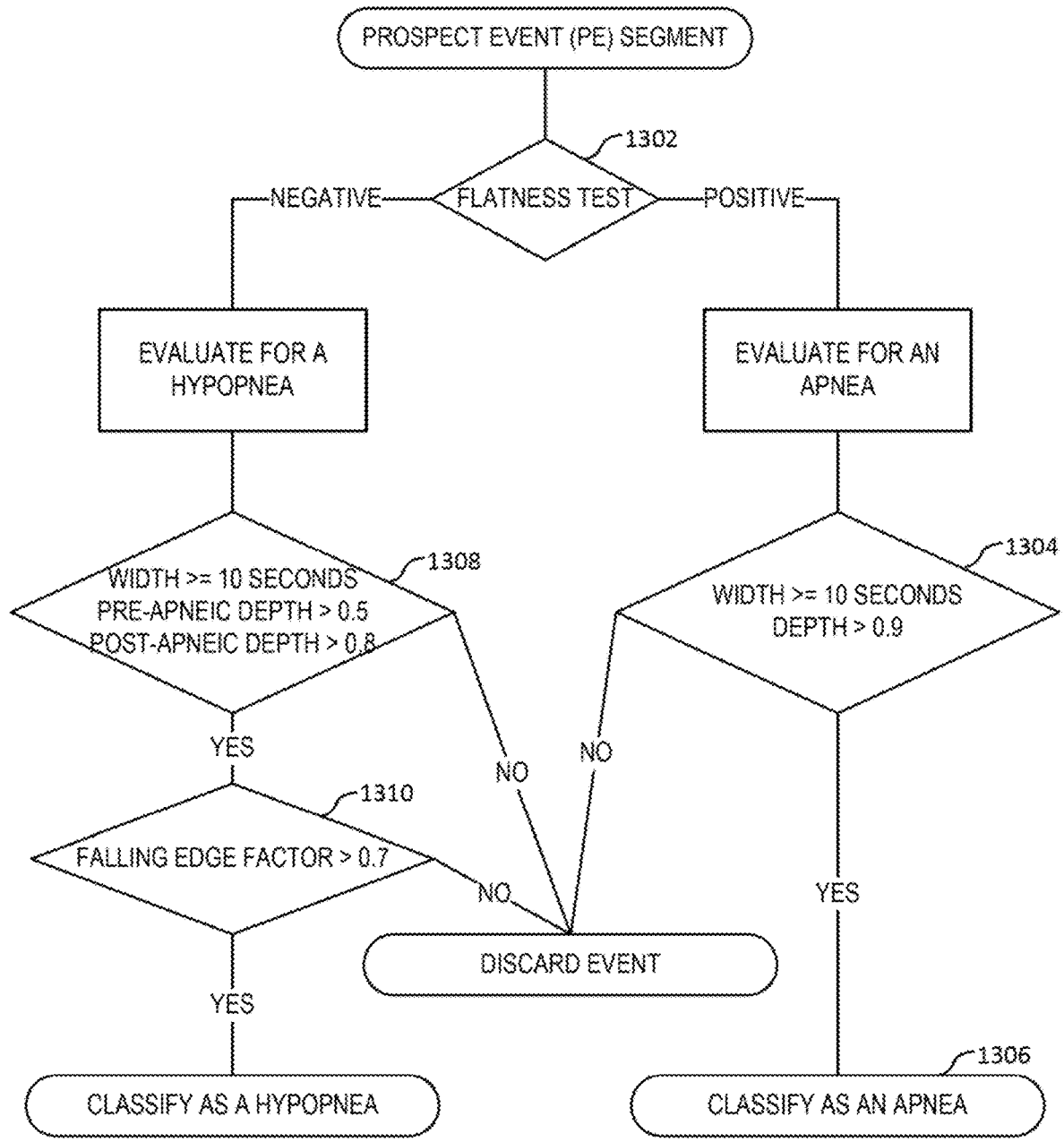
FIG. 13 is a flowchart of an exemplary method for classifying apneas and hypopneas from identified prospect events, in accordance with one embodiment of the invention.

FIG. 13 provides a specific example of a method for detecting apneas and hypopneas, in accordance with an embodiment of the invention, which method was used in validating the efficiency and accuracy of this method, as discussed hereinbelow.

To develop and validate the above-described and below-detailed methods, and in accordance with one embodiment of the invention, a series of patients suspected of sleep apnea were tested, and their results analyzed in accordance with the below-described method. Namely, for the results discussed below, 50 consecutive patients of at least 18 years of age that were referred to a sleep laboratory due to snoring or suspected sleep apnea, were tested both using the below-described method and by standard measures so as to validate the results discussed below. No exclusion criteria were imposed and subjects refrained from alcohol, sedative medications and caffeine for 12 hours before sleep studies.

In this particular example, subjects underwent overnight sleep studies using standard techniques and scoring criteria for sleep stages and arousals from sleep. All subjects slept with one pillow and with the bed flat. Thoracoabdominal movements and tidal volume were measured by respiratory inductance plethysmography, and airflow by nasal pressure cannulas. Arterial oxyhemoglobin saturation was monitored by oximetry. Obstructive apneas and hypopneas were defined as per standard methods as a cessation of tidal volume and at least a 50% reduction in tidal volume from baseline but above zero, respectively, lasting at least 10 seconds with out-of-phase thoracoabdominal motion or flow limitation on the nasal pressure tracing.

Apneas and hypopneas were scored according to 2 different criteria. The first was the American Academy of Sleep Medicine (AASM) criteria which defines an apnea as a drop in the respiratory signal, in this study thoracoabdominal movement, by ≥90% lasting ≥10 seconds, and a hypopnea as an event that satisfies either of the following 2 conditions: a drop of respiratory signal (from RIP in this case) by ≥30% lasting ≥10 seconds and accompanied by either a ≥4% desaturation, or a drop of respiratory signal by ≥50% lasting ≥10 seconds and accompanied by either a ≥3% desaturation or terminated by an arousal. These are not mutually exclusive. For the second criteria, apneas were similarly defined, but hypopneas were defined as a 50% to 90% reduction in tidal volume from baseline from the sum channel of the RIP tracing lasting ≥10 seconds, regardless of any desaturation or arousal, which criteria are referred to hereinafter as TV50. The AHI was quantified as the number of apneas and hypopneas per hour of sleep time.

For the purpose of comparative breath sound analysis, in accordance with one embodiment of the invention, breath sound data was also recorded for these subjects by a cardioid condenser microphone (Audi-Technica condenser microphone). The microphone's cardioid polar pattern reduces pickup of sounds from the sides and rear, improving isolation of the sound source. The microphone was embedded in the centre of a loose fitting full-face mask frame, for example as shown in FIGS. 1 to 4. As shown in these figures, the mask provided a structural frame to keep the microphone in a fixed location approximately 3 cm in front of the subject's face. Digitized sound data were transferred to a computer using a USB preamplifier and audio interface (M-Audio, Model MobilePre USB) with a sampling rate (Fs) of 22050 Hz and resolution of 16 bits. For the purpose of this study, the external audio interface was preferred over the regular built-in audio adapters because of its better Signal to Noise (S/N) ratio, which is 91 dB (typical, A-weighted), though it will be appreciated that either of these adapters, or others like them, may be used in different embodiments to produce similar results.

To ultimately detect reductions and/or interruptions in breathing (i.e. hypopneas and apneas), and in accordance with one embodiment, breath sound recordings were first analyzed to evaluate the temporal evolution of breath sound amplitude in these recordings. For this purpose, signal envelopes were created to detect overall changes in the amplitude of the acquired signal, (e.g. in the steps described below).

For example, in this embodiment, the breath sound signal amplitude envelope was extracted to preserve sharp transitions in the signal, which is a specificity of the signal in hand that could have sudden transitions from silence during an apnea to hyperventilation up on resumption of breathing. To do so, the following steps were followed.

Extracting Envelop of Individual Breaths (BE)

In this step, the recording is divided into non-overlapping segments, for example of 500 ms duration. Data points in each given segment are then summed to produce a single bin that represents the 500 ms segment. The length of the interval is chosen in order to balance between preserving short term details such as onset of inspiratory and expiratory phases, and longer term events such as apneas and hypopneas. Since the shortest breathing phase is generally 1.5 seconds in rapid normal breathing (i.e. 20 breaths/minute), a bin size/segment duration of about 500 ms, as in the present example, generally provides sufficient resolution to capture such breathing details. As will be appreciated by the skilled artisan, different bin/segment sizes may be considered herein without departing from the general scope and nature of the present disclosure. This person will however appreciate that overly extended segment intervals may have adverse results, for example in the merging of apnea borders and thus resulting in a false representation of the apnea's duration, or again in the merging of transient high amplitude outliers produced by coughing and snorting (transient load snoring) with surrounding signals thus making them more difficult to remove in subsequent steps.

The resulting signal is a train of peaks, each representing a breathing phase, which are interrupted by apneas as illustrated, for example, in the 3 minutes recording in FIG. 9.

Outlier Removal

While successive breaths do not tend to vary dramatically in amplitude, these may be interrupted by transients such as cough, or snorting (transient loud snoring). Such transients thus occasionally appear as outliner spikes in the envelope of individual breaths, as extracted in the previous step. Since such outliers can affect subsequent steps, it is generally preferable that they be removed.

In one embodiment, an outlier is defined for this purpose as high amplitude data points that exceed 4 standard deviations ($4\sigma$) of the surrounding 180-second data segment, which segment length was selected in this particular embodiment in consideration of a general apnea cycle length. Namely, in patients with severe sleep apnea, breathing is present only roughly 50% of the time and is interrupted by apneas that are approximately 30 seconds in duration. Thus, approximately every 60 seconds, an alternating pattern of apnea and ventilation occurs repeatedly during sleep and this constitutes the basic unit of segmentation. In order to incorporate multiple patterns, a segmentation window of 180 seconds (=3×60) was chosen. As will be appreciated by the skilled artisan, this interval should be minimized as much as possible in order to avoid incorporation of meaningful long term change of breathing type, such as moving from quiet breathing to snoring, or the like.

In order to remove outliers, BE is segmented into short segments each of 180 s that overlap by 50%. All data points greater than $4\sigma$ are truncated to $4\sigma$. It should be noted that, in the case of consecutive points that indicate the presence of outliers, the duration of these consecutive points should not exceed 5% of the length of the segment. Otherwise, the detected strong amplitude deviations are not considered outliers, as they could still contain physiologically relevant information.

Extracting Envelop of Breathing Effort

The next step is to trace the overall changes in waveform level. These changes are the result of apneas and hypopneas and also the change in breathing pattern. This is achieved by interpolating the waveform's maxima to extract the effort envelop (EE), as illustrated in FIGS. 11, 14 and 15. This particular envelop can then be used, as noted above and in accordance with different embodiments, to detect individual apneas and hypopneas.

Amplitude Normalization of EE

Figure 10:
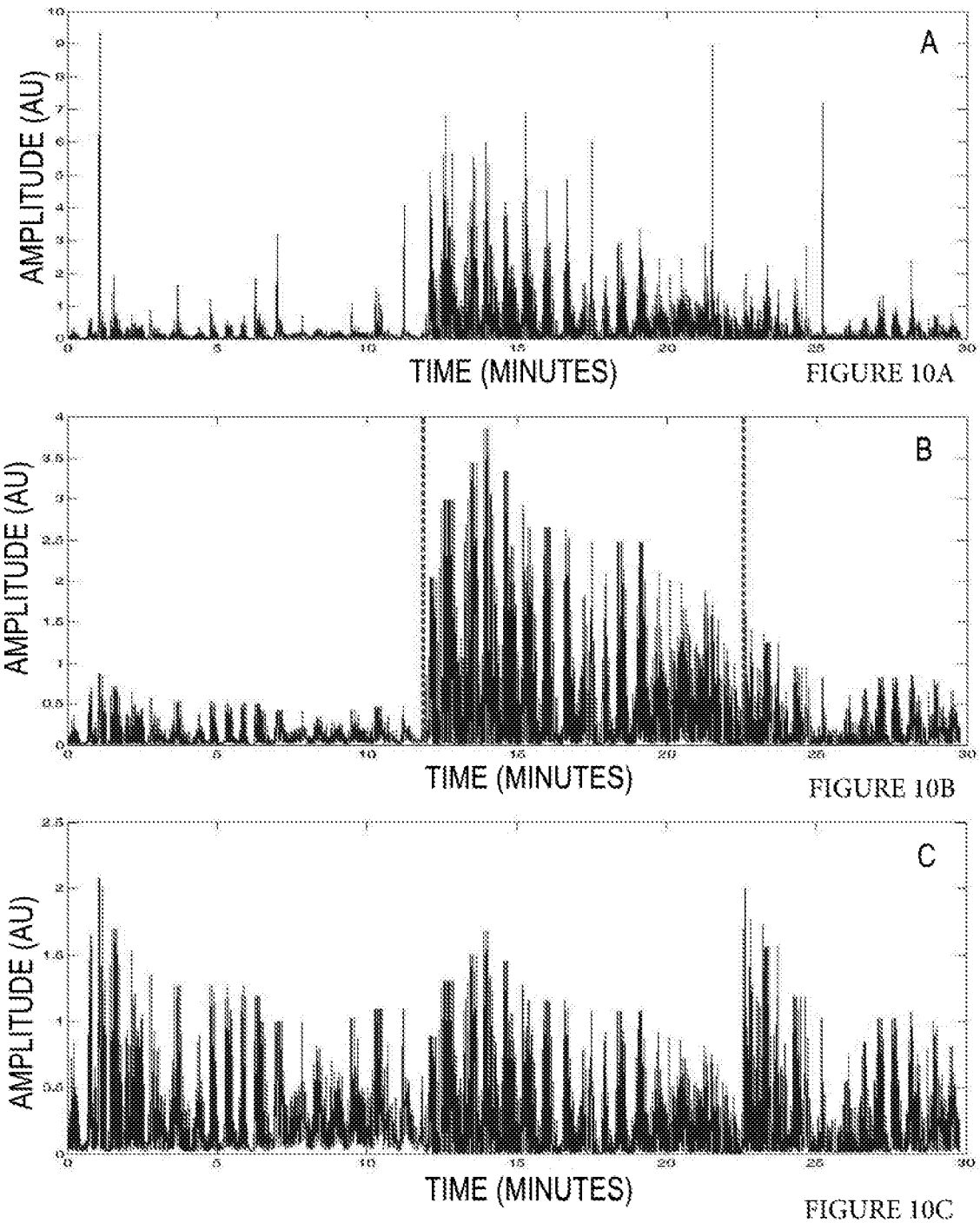

In order to improve the accuracy of apnea, and particularly hypopnea detection, which are represented by relative reductions of breathing effort, in one embodiment, the method uses a baseline level of breathing sounds as reference. Breath sounds, however, generally produce particularly dynamic and variable signals due to the occurrence of snoring and variations in breath types. This can thus result in long term variations in the overall amplitude of the EE that can obscure accurate detection of hypopneas for lack of a suitable reference baseline. Accordingly, and in accordance with one embodiment, an overall normalization of the signal's amplitude is provided in order to enhance hypopneic event detection. In one example, an adaptive segmentation method is used to provide such normalization, wherein borders between long-term varying levels are found so to then respectively normalize each of these levels to unity. This results in a substantially uniform amplitude of the breath sound signals over extended periods, yet preserving short term variation due to apneas and hypopneas. An example of this process is shown in FIG. 10, where the breathing envelope (BE) of the digitized breathing sound (BS) train in (A) is first cleaned of outliners to produce the BE in (B), which is then itself submitted to segment-based normalization as noted above to obtain the preprocessed BE (otherwise referred to as the BE of the rectified BS) in (C), from which preprocessed BE a more accurate breathing effort envelope (EE) may be extracted, as in FIG. 11.

Scanning for Prospect Apneic and Hypopneic Events

Using the preprocessed (i.e. normalized and outlier-free) EE, as produced in one embodiment following the above-described steps, apneic and hypopneic event detection may then be implemented. Namely, this preprocessed EE generally represents a trace of the overall breath sounds amplitude, from which characteristic patterns of apneas and hypopneas can be automatically identified.

In one embodiment, the signal is scanned to first identify prospect apnea/hypopnea events. For example, in one embodiment, valleys in the EE signal that are below a predefined threshold are first identified. For example, an empirical threshold of 0.4 of a standard deviation below the mean of EE has been shown to provide adequate results. Accordingly, this step allows for the detection of troughs in the signal that have sufficient depth to possibly correspond to an event of interest, while excluding negligible signal troughs that could more likely be attributed to breath-to-breath variation.

In a following step, each identified valley is extracted from the main EE. This is achieved, in one embodiment, by extracting a 60 seconds long segment whose centre is the deepest point of the trough or the middle of the trough if it is a flat region. Hereafter, this segment is named prospect event apnea (PE). Each PE will generally contain a central trough in addition to proceeding and subsequent activities given that an apneic/hypopneic event generally lasts between 10-50 seconds. The activities that proceed or follow an event will thus also be used as criteria to detect true events of apnea and hypopnea.

Since the 60 seconds interval of a given PE may contain redundant data when the event's length is relatively short, an additional step can be used to delineate the borders of the event that correspond to normal breathing level. For example, in one embodiment, this step is achieved by selecting the closest peak to the centre on both sides that exceeds 50% of the maximum point of the PE. Using this two-step approach to PE border identification, the process both mimics human intuition in finding drops in breathing by comparing the levels of a given trough to immediately adjacent data, and accounts for subtle changes in breath sounds level that remain present despite the normalization and which would otherwise make border identification via comparisons with a universal level for the entire recording likely inaccurate.

In this embodiment, each PE is then normalized to unity by dividing it by its maximum and subtracting any offset so that the minimum point is zero. This step casts all PE's into a similar level range (0-1), as depicted in FIG. 11, thus facilitating subsequent processing steps.

Detection of True Apneas and Hypopneas

In order to detect true events, and in accordance with one embodiment, each PE is evaluated based on preset conditions. Since apneas and hypopneas differ in their nature, their manifestations in breath sounds are also generally different. For example, there is generally a complete collapse of the upper airway and the absence of breathing and breath sounds during an apnea. Also, pre and post apneic breaths are often relatively irregular, especially in OSA. On the other hand, hypopneas are often characterized by a partial collapse of the upper airway and a reduction of airflow by more than 50% but still remaining above zero. Thus, breath sounds may continue to occur during a hypopnea. Accordingly, in one embodiment, in order to identify and differentiate apneas and hypopneas, different preset conditions are applied to identify each type of event, and thus provide for enhanced diagnosis and improved treatment.

Tests for Apneas

In one embodiment, a set of criteria are applied to each PE to identify whether it qualifies as a full apnea. In general, such criteria seek to evaluate the presence of any substantially flat segment (step 1302), wherein, upon such flat segment satisfying both duration and depth criteria (step 1304), the PE is positively identified as an apneic event (step 1306). For example, flatness in the acoustic data generally corresponds to a lack of breath sounds, and can be evaluated by counting the number of zero or near-zero points in a given PE. If the number of those points corresponds to a preset time interval, or above, then an apneic event may be positively identified. In one embodiment, the preset time interval is set at 10 seconds, and the length of the flat segment is calculated as $LApnea = Ts \cdot \|PE<0.01\|$, where $\|PE<0.01\|$ denotes the length of a vector for which PE amplitude is below 0.01, and Ts is the sampling period (1/sampling frequency (Fs)).

To evaluate the depth of an identified flat segment, the amplitude of this segment is compared with the amplitude of the higher of the two apneic borders obtained in the previous step where prospect events are first identified. For example, in one embodiment, if the depth of a substantially flat segment as identified above is greater than 0.9, then the segment is deemed to identify a true apneic event. Accordingly, upon qualifying a given PE as comprising a sufficiently flat segment of sufficient depth, that particular PE is classified as an apnea and automatically counted as such.

Tests for Hypopneas

In the event that the above-described predefined apnea requirements are not met for a given PE, a distinct set of predefined hypopnea requirements may still be applied to account for any potential hypopneas. For example, in one embodiment, if the flatness test (step 1302) set out above comes back negative, e.g. where the computed length of an identified substantially flat segment is below the prescribed threshold, then this PE is passed on to next stage where hypopneic criteria may be applied to evaluate whether this PE rather represents a true hypopnea. In the current example, this set of criteria consists of a falling edge test, a width test, and a depth test (step 1308).

The falling edge test in this embodiment is based on the assumption that a hypopnea evolves as a gradual reduction in net airflow as a result of gradual collapse of the throat in the obstructive type, or gradual decrease in respiratory drive in the central type. This reduction, however, does not always manifest in an ideal smooth negative slope because of the variable nature of breath sounds on a breath-to-breath basis. Therefore, the falling edge test can be configured to take into consideration the non-linearity of the drop in breath sounds amplitude prior to the hypopnea, which may be achieved in accordance with the following steps:

1. The falling edge (FE) of the PE is extracted from the first point of the PE to its minimum point.
2. The derivative of FE is calculated as the difference between each point and the preceding point. The results are stored in an array. If FE is decreasing at all points, then the derivative will consist of negative values only. Positive elements of the array represent transient peaks during the overall drop of the breath sound level. The absolute value of the sum of all these points will thus give the difference between the first and last values of FE.
3. All the points in the FE derivative are summed up to get a single value and the sum of all positive numbers in the derivative is extracted from that value.
4. The result of step 3 is divided by the difference between the maximum and minimum point in FE. The absolute value of this result is called the falling edge factor. Since the minimum value is always zero because of the offset subtraction described earlier (PE normalization), it is sufficient to divide by the maximum point.

Based on the above, the falling edge factor can be obtained from the following equation:

$$\text{FE factor} = \|\Sigma\Delta(\text{FE}) - \Sigma(\Delta(\text{FE}) > 0)\| / \max(\text{FE})$$

where $\Sigma$ denotes summation, $\Delta$ denotes discrete derivative, '>0' denotes positive elements of a vector, and $\|\blacksquare\|$ denotes the absolute value.

If the FE is decreasing at all points, then the sum of the derivative array elements is equal to the maximum of the FE, which is the starting point; thus the falling edge factor will be equal to 1. In this case, it will be interpreted that the breath sounds level decreased from the full loudness in normal breathing to the faintest level in the hypopnea in a completely gradual trend. On the other hand, if FE contains transient peaks, the FE derivative will contain positive values that will decrease the numerator of the above equation for the FE factor. Accordingly, the result will be less than 1 depending on the number of rises and their height, which are not consistent with a net gradual decrease in breathing effort. In order to differentiate, at step 1310, FE factors indicative of hypopnea from those more likely indicative of regular breathing, a predefined FE factor threshold is applied, whereby a FE factor computed above this threshold is maintained as indicative of a PE representative of a possible hypopnea, whereas a FE factor below this threshold automatically excludes this PE from a total hypopneic count. In this particular example, the preset FE factor was set at 0.7, which translates into a 70% decreasing trend or greater.

As noted above, however, the present example contemplates a three part test for accurately identifying a hypopneic event, whereby failure of any one of these tests results in the exclusion of a related PE from hypopneic counts. As a second criteria in this example, the PE is processed for compliance with a hypopneic width requirement (step 1308), which effectively provides for a measure of an effective PE duration as compared with a preset duration threshold, whereby an effective PE duration computed as being greater than the prescribed threshold may be indicative of a true hypopnea. In this example, the width test is performed by measuring the time interval (duration) between the FE and rising edge (RE) when at the lower quarter of the PE given by the equation:

$$\text{PE duration} = T_S \cdot \|PE_{Iq}\|$$

where PEIq denotes elements in the lower quarter of PE. In this embodiment, a measured PE duration greater or equal to 10 seconds is retained as a possible hypopnea, whereas shorter durations are rejected from hypopneic counts.

Again in accordance with this exemplary embodiment, a third test is applied consisting of a hypopneic depth test, which is similar to the one used to evaluate an apnea and calculated similarly as the difference between the maximum and minimum values of the PE, the latter being zero of course in a normalized PE. To compute this result, the maxima are taken at the start and end points of PE, wherein the starting peak represents the level of the pre-apneic breathing and the end peak represents post-apneic hyperventilation. In this example, a possible hypopneic event is identified where the starting peak measures at least 0.5, which is based on the 50% fall in breathing effort by definition of an apneic event. The end peak, on the other hand, corresponds to the post-apneic hyperventilation, which is higher in amplitude. Therefore, it stands to reason to expect that the end peak is higher than the start peak. Accordingly, in this example, a higher threshold of 0.8 is set for the post-apneic peak. As will be noted, the hypopneic thresholds are lower than that set for the apneic depth test, in which total cessation of breathing takes place, but high enough to substantially exclude false positive results. In this example, the combination of these three tests (falling edge, width, and depth criteria) were shown to encompass the specific physiological characteristics of hypopneas yet, remain sufficiently flexible to detect different forms that result from the dynamic nature of breath sounds.

Results of Comparative Study

As introduced above, in order to validate the performance of the above-described process, the results thereof were compared against results obtained by PSG, which currently represents the most accurate standards in the art. In making this comparison, the total number of the detected apneas and hypopneas from breath sounds was divided by the recording time to get the acoustic apnea-hypopnea index (AHI-a). This was compared with the polysomnographic apnea-hypopnea index (AHI-p), which is the frequency of apneas and hypopneas obtained from polysomnographic recordings divided by recording time. The AHI-p was evaluated according to the recording time rather than sleep time in order to simulate home recording of breath sounds where EEG will not be available.

As can be seen from the plots presented in FIGS. 16 to 19, results obtained in accordance with the above-described method are consistent with those independently obtained via PSG, thus validating the efficiency and accuracy of the herein-disclosed embodiments relying on breathing sound analysis.

For instance, in the above-described example, the acoustic (i.e. breathing sound-based) apnea-hypopnea index (AHI-a) was calculated automatically from acquired data and compared to the average of three AHI-p values. As can be seen from FIG. 16, acoustic AHI showed 95% agreement with the mean PSG AHI of 3 scorers ($R^2$=0.90). In this Figure, a solid reference line is drawn to represent equality of the acoustic and standard AHI measures and dashed reference lines are drawn at differences of 5 and 10 points. It can be seen that the acoustic AHI lies within 10 points of the average AHI for all but one subject. It can also be seen that for small AHI values (<15), most acoustic AHI values lie within 5 points of the mean for the standard AHI.

To further evaluate the performance of the above-proposed methods, the AHI obtained from acoustic recordings (AHI-a) was further compared with that obtained from PSG (AHI-p) while accounting for the fact that the AHI-p is obtained by a technician visually scoring the PSG recordings, raising the possibility of scoring variability between technicians for the same PSG. To determine the degree of inter-rater variability in the scoring of the AHI, 3 experienced sleep technologists scored the AHI of each of the 50 patients, blinded to the score of the other technicians and to the AHI-a. Similarly, the AHI-a was determined automatically without knowledge of the AHI-p.

Since the AHI-p scores of the 3 technicians represent the reference standard, the degree of agreement was assessed amongst the 3 technicians prior to comparison with the AHI-a. The inter-rater reliability among the 3 technicians and its 95% confidence interval were calculated using the know Analysis of Variance (ANOVA) method.

The degree of agreement between the 2 methods was assessed by Pearson correlation and Bland-Altman tests. For those tests, the AHI was evaluated according to the time-in-bed period rather than sleep time to simulate home recordings of breath sounds where sleep stages are not recorded. Correlation coefficients with all 3 scorers were calculated using pairwise differences in Pearson correlation and using bootstrap (n=2000) to obtain the 95% confidence interval (CI).

To test the ability of acoustic analysis to distinguish between the presence or absence of SA, the accuracy, sensitivity, specificity, positive and negative predictive values, and positive and negative likelihood ratios were calculated. These were first calculated according to time-in-bed for both AHI-a and AHI-p, and then, according to time-in-bed for AHI-a and sleep time for AHI-p.

Figure 17A:
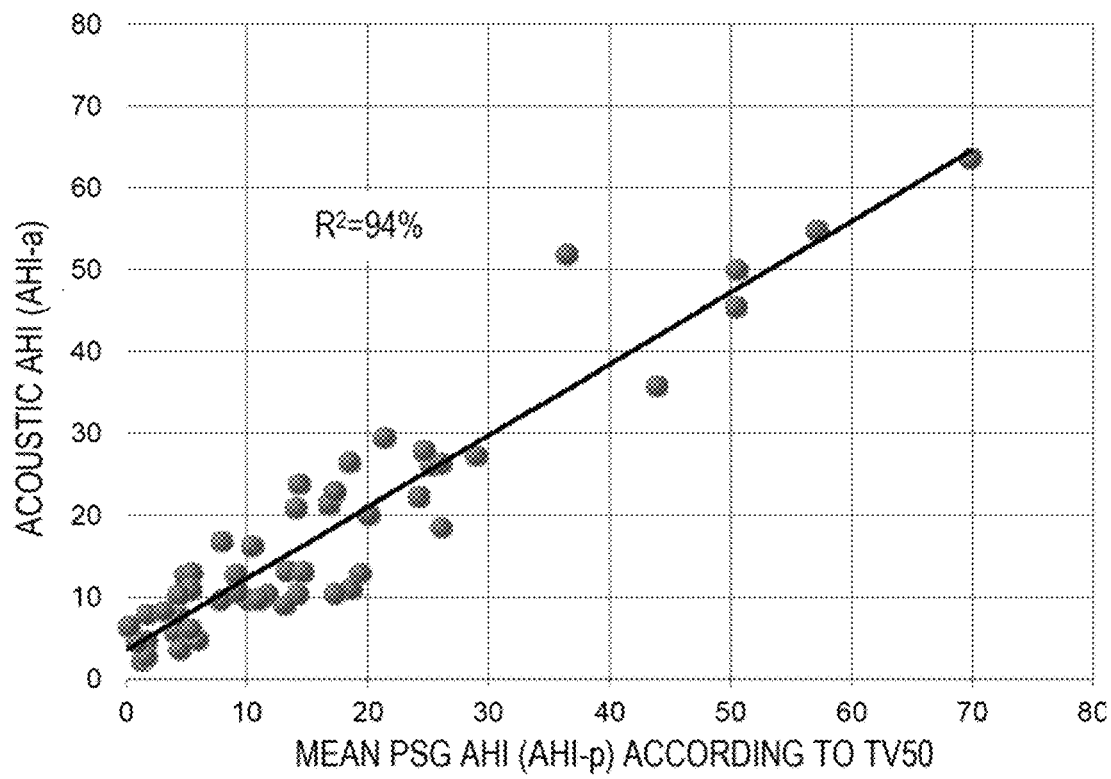
FIGS. 17A and 17B are plots showing a distribution of AHI-a and 3 AHI-p scores as a function of the mean AHI-p score, obtained according TV50 and AASM standards, respectively.
Figure 17B:
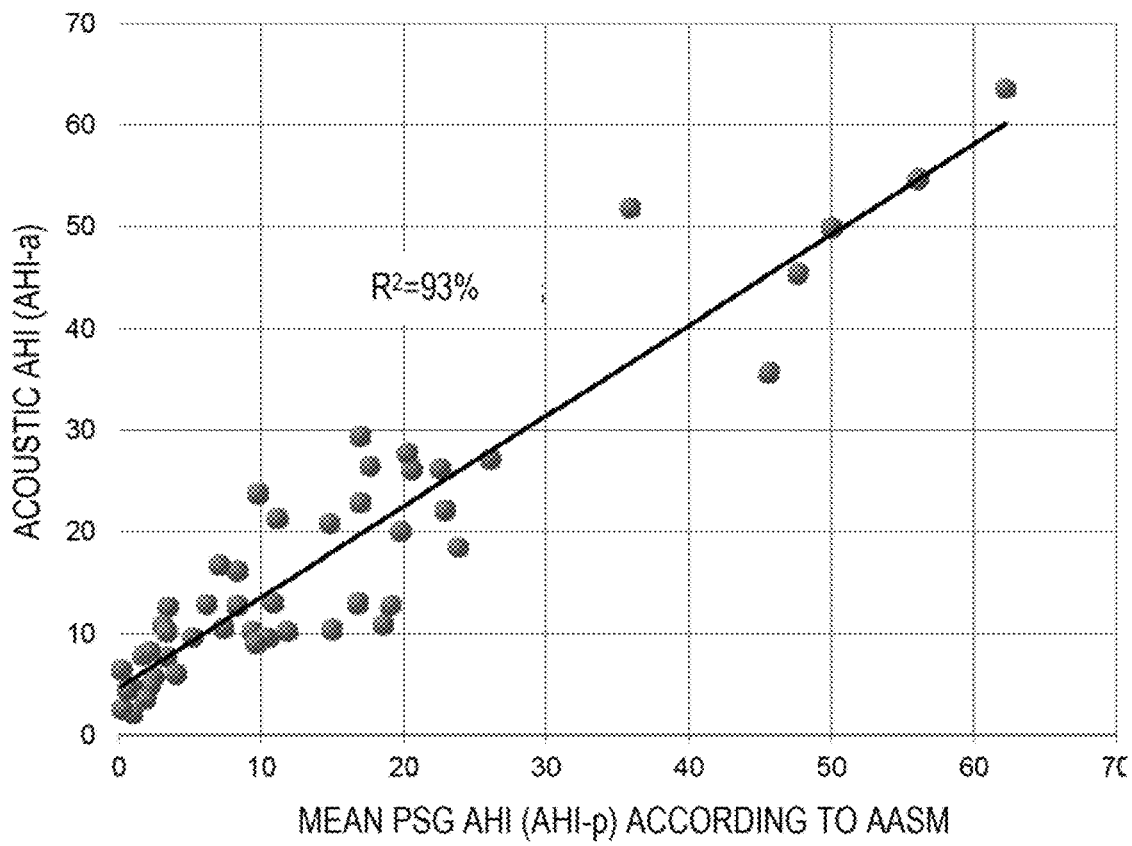

In comparing AHI-a and AHI-p, a strong correlation was identified with a mean R=0.94 and a 95% CI of 0.87-0.97 according to TV50 criteria, and a mean R=0.93 and 95% CI of 0.85-0.96 according to AASM criteria. FIG. 17 displays the distribution of the AHI-p scored by each of the 3 technicians and the relationship between the AHI-a and the mean AHI-p for TV50 (A) and AASM (B).

Figure 18:
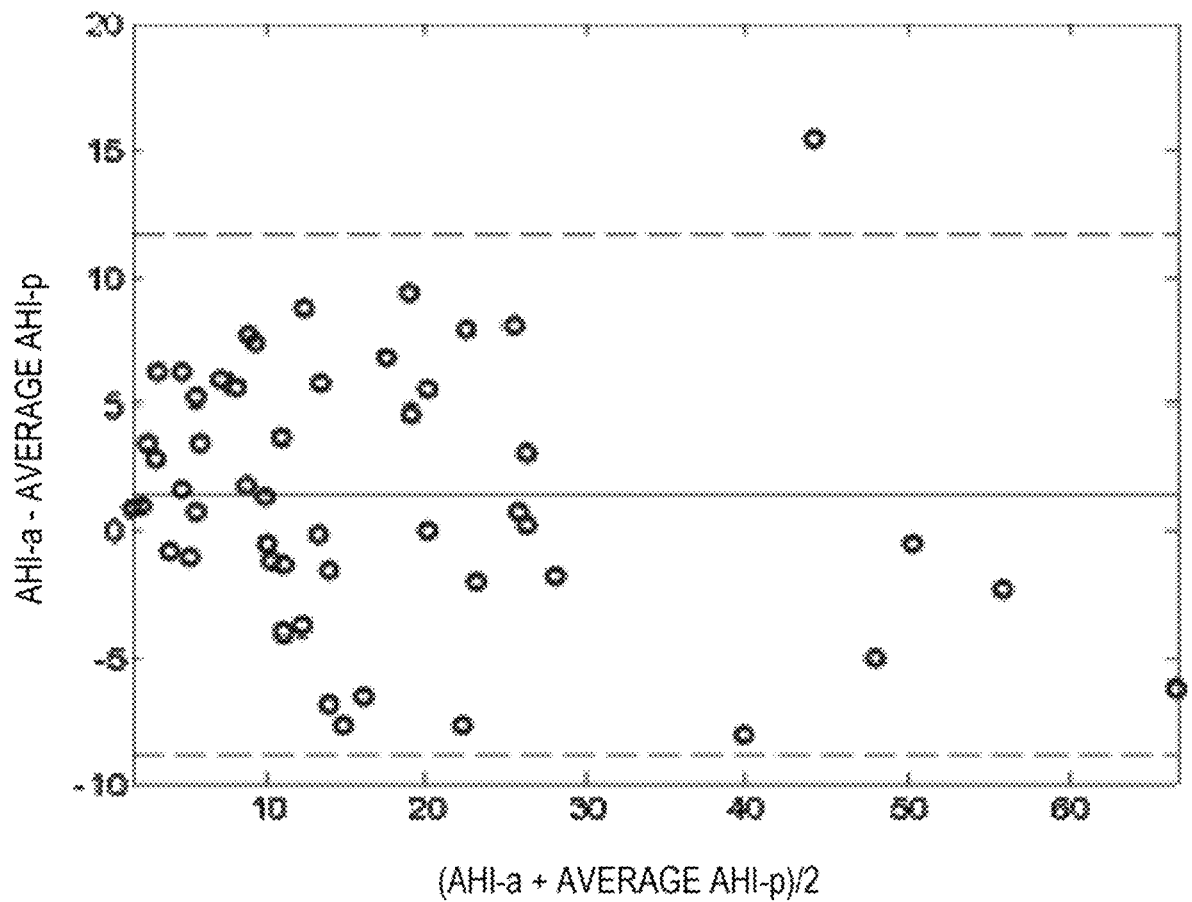
FIG. 18 is a Bland Altman plot showing AHI-a scores falling within Limits of Agreement with respect to AHI-p scores.
Figure 19A:
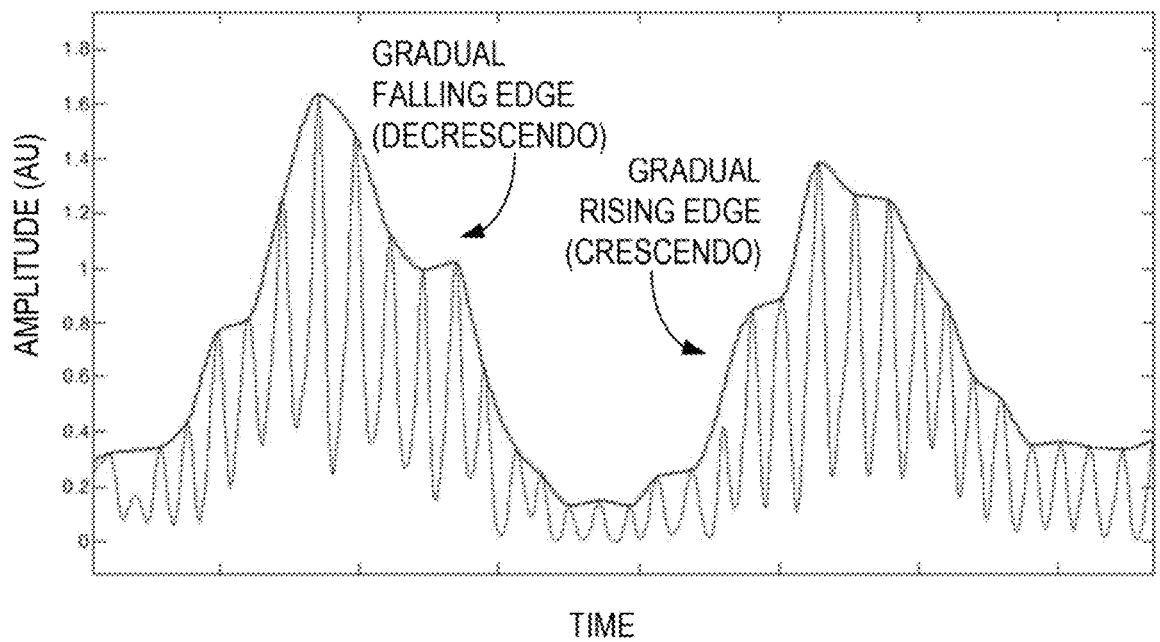
Figure 19B:
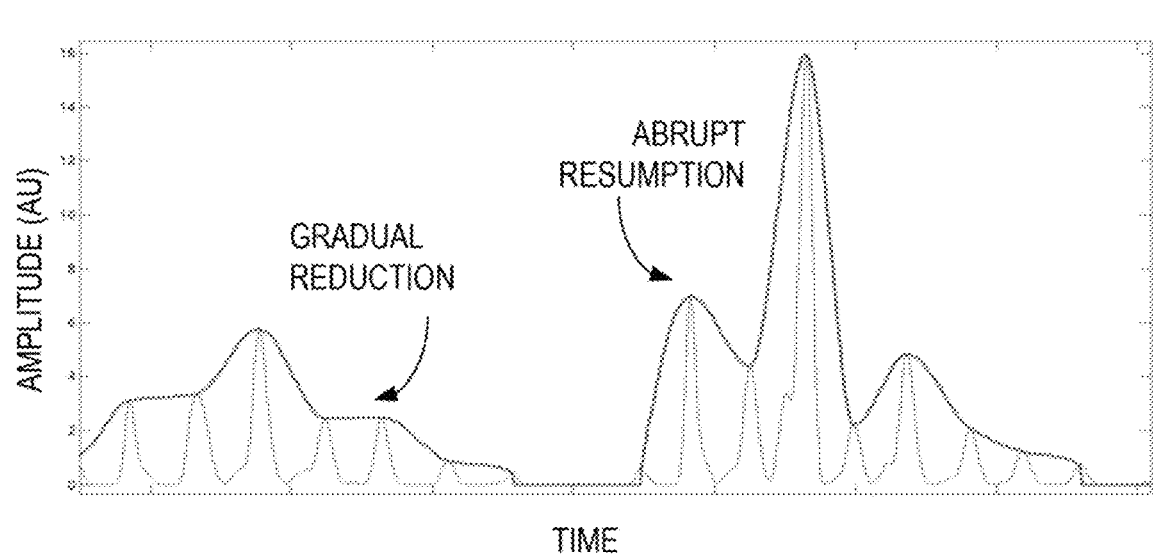

The Bland-Altman limits of agreement were calculated to assess agreement between the AHI-a and the AHI-p of each of the three technicians and the mean of all three. Forty nine of the 50 AHI-a (98%) fell within the limits of agreement of the AHI-p for TV50 as shown in FIG. 18. Similarly, 96%, 96%, and 98% of AHI-a scores fell within the limits of agreement of AHI-p scored by technicians 1, 2, and 3, respectively. The proportion of AHI-a scores that fell within the limits of agreement of PSG-p according to AASM was 92%, 94%, 92%, and 92% in comparison with technicians 1, 2, 3, and their mean scores, respectively.

According to the criterion set in the present example, a diagnosis of SA is made if the AHI≥10, whereas SA is ruled out if the AHI<10. In comparing the diagnosis of SA based on AHI-a to that based on the three AHI-p, a decision rule for combining the diagnoses from the 3 technicians was obtained. Two approaches were considered in doing so. First, a diagnosis was considered based on the average of the three technicians, such that SA was positively identified if the mean score was ≥10. Second, a diagnosis was considered based on the agreement of AHI-a with at least one technician. In this case, if AHI-a≥10 and at least one of the three AHI-p≥10, then the AHI-a diagnosis of SA is considered to be a true positive, whereas a false positive ensues if AHI-a≥10 and all three AHI-p<10. The same concept was applied to true negative and false negative values. The rationale behind investigating this approach was that the agreement of the acoustic analysis with one technician indicates that the first lies within the range of inherent variability among different human scorers, which could indeed result in fluctuations of scores around the nominal cut-off of AHI≥10 among the technicians themselves.

The comparisons of diagnostic accuracy of the AHI-a compared to either the mean of the three AHI-p values, or compared to the AHI-p scored by one or more technicians using TV50 or AASM criteria are presented in Table 1 and Table 2, below. Considering that the agreement with at least one technician incorporates the range of the three scores for the same subject, it factors in the inter-rater variability around the nominal cut-off point. When comparing agreement with at least one of the three technicians, validity measures were 100%, 73%, and 88% for sensitivity, specificity, and accuracy, respectively, according to TV50. When comparing against the mean AHI-p those dropped to 95%, 69%, and 84% (Table 1). These values were comparable but slightly lower when comparing AHI-a against AHI-p according to AASM criteria (Table 2).

TABLE 1

Diagnostic agreement according to TV50 scoring criteria.

| According to 1 or more technicians | | According to mean AHI-p | |
|---|---|---|---|
| Sensitivity | 100% | Sensitivity | 95% |
| Specificity | 73% | Specificity | 69% |
| Accuracy | 88% | Accuracy | 84% |
| LR+ | 3.7 | LR+ | 3.0 |
| LR− | 0 | LR− | 0.07 |
| PPV | 0.82 | PPV | 0.81 |
| NPV | 1 | NPV | 0.90 |

TABLE 2

Diagnostic agreement according to AASM scoring criteria.

| According to 1 or more technicians | | According to mean AHI-p | |
|---|---|---|---|
| Sensitivity | 100% | Sensitivity | 96% |
| Specificity | 70% | Specificity | 64% |
| Accuracy | 86% | Accuracy | 81% |
| LR+ | 3.3 | LR+ | 2.7 |
| LR− | 0 | LR− | 0.06 |

TABLE 2-continued

Diagnostic agreement according to AASM scoring criteria.

| According to 1 or more technicians | | According to mean AHI-p | |
|---|---|---|---|
| PPV | 0.79 | PPV | 0.75 |
| NPV | 1 | NPV | 0.94 |

When employing PSG for diagnosis of SA, the AHI is calculated by dividing the number of apneas and hypopneas by the total sleep time. However, since the above-described system is, at least in some embodiments, contemplated for use in a home setting where sleep onset is not as readily identifiable as in a sleep laboratory setting, further investigation compared the AHI-a values calculated with time-in-bed as the denominator, to AHI-p values with total sleep time as the denominator, using TV50 criteria. Validity measures revealed improvement over AHI-p based on recording time, with an overall accuracy up to 90%, as shown in Table 3, below.

TABLE 3

Diagnostic agreement between AHI-a based on time-in-bed and AHI-p based on total sleep time using TV50.

| According to 1 or more technicians | | According to mean AHI-p | |
|---|---|---|---|
| Sensitivity | 97% | Sensitivity | 93% |
| Specificity | 79% | Specificity | 72% |
| Accuracy | 90% | Accuracy | 85% |
| LR+ | 4.6 | LR+ | 3.3 |
| LR− | 0.04 | LR− | 0.09 |
| PPV | 0.88 | PPV | 0.84 |
| NPV | 0.94 | NPV | 0.88 |

As can be seen from FIG. 18, the high sensitivity of the proposed method can be attributed to the slight but systematic over scoring of cases in the lower range (AHI<15). As will be appreciated by the skilled artisan, it is generally clinically safer to over-score than to under-score border line cases in order to avoid missing diagnosis of patients who may need treatment. Of interest, the false positive cases were close to the cut-off AHI point of 10. In one embodiment, this consideration can be addressed by defining a zone of uncertainly between the AHI-a of 10 to 18 where false positives lie. Treatment of SA is ordinarily prescribed for the presence of an SA syndrome based on an AHI and the symptoms of SA determined by a clinical evaluation. Therefore, as would be the case for a borderline AHI-p, the clinical significance of an AHI-a in this zone of uncertainty for a given patient would require a clinical evaluation to assess for symptoms of a sleep disordered breath syndrome. In the presence of such symptoms, a trial of SA therapy would be justified, but in the absence of such symptoms, treatment of the borderline AHI-a would not be mandated. The tendency to over score the AHI from breath sound analysis compared to AHI-p in the lower range would thus not compromise the ability to discard negative cases as revealed by the negative predictive value (NPV) of 100% and negative likelihood ratio (LR−) of zero (i.e. when compared to one or more technicians). These data indicate that an AHI-a<10 reliably rules out the presence of SA. Such reliability in ruling out SA is an important feature of a portable sleep apnea monitoring device since it would obviate the need to perform costly PSG and prescribe unnecessary interventions to subjects with a low AHI who do not need them.

As demonstrated by the above results, significant agreement was observed between the AHI assessed by acoustic analysis of breath sounds using the above-described methods and devices, and that determined simultaneously during full in-laboratory PSG. As noted above, overall accuracy for diagnosis of SA reached 90% with 94% correlation across the spectrum of AHIs, with 98% of AHI-a falling within Bland Altman limits of agreement with AHI-p.

The above-described methods and devices thus provide a reliable and accurate approach to SA identification, characterization and/or diagnostics, while providing for a readily accessible solution for home use via the provision of a less invasive and more user friendly apparatus. Namely, unlike PSG, which generally requires specialized installation, care and operation of the 12 or more acquisition channels, the above-described system and methods can provide comparable results, in some embodiments, using as little as a single channel acquired by way of a breath-sensitive transducer positioned in a nose and mouth area of the subject.

Furthermore, while PSG generally seeks to calculate the AHI by dividing the number of apneas and hypopneas by total sleep time, which generally requires the presence of a trained technician to apply multiple electrodes to record electroencephalographic, electo-oculographic and electromyographic signals to determine the presence, and quantify the amount and type of sleep, the above-described devices and methods dispense of such requirements while still allowing for accurate determination of the AHI based on total recording time. This again facilitates home use and increases portability of the herein-described embodiments. Regardless, the herein-described methods and devices may further incorporate a calibration factor whereby a total sleep time could be estimated as a function of a total recording time to further increase AHI accuracy. These and other such considerations will be apparent to the person of ordinary skill in the art and are thus considered to fall within the scope of the present disclosure.

As will be appreciated by the skilled artisan, these results confirm the validity of the above proposed approach, which can not only be used for diagnosing sleep apnea, but also its severity in automatically outputting an AHI (step 640) from recorded breath sounds only.

Furthermore, the above-described example may accommodate natural variations in breath sounds, which may include, but are not limited to snoring, regular breathing and variations in acoustic amplitude levels. Not only does this flexibility allow for greater versatility in achieving usable results, it may also allow candidates suffering from different types of disorders to be diagnosed. For example, as discussed above, methods relying solely on snoring sounds do not accommodate candidates whose conditions are not necessarily manifested through snoring, such as candidates suffering from CSA for whom snoring does not necessarily occur. Comparatively, embodiments described herein may allow for a detection of sleep apnea in candidates suffering from CSA or OSA alike.

Within the context of the overall process of FIG. 6B, the detection of apneic and/or hypopneic events allows both for a local result to be produced in characterizing a subject's condition (e.g. identification of sleep apnea and severity thereof), and for the use of such data in the further classification of the identified condition as CSA or OSA, as will be described further below.

Sound Amplitude Profile Analysis

With reference again to FIG. 6B, further processing of the expiratory data considered above can be implemented, for example at step 614, to contribute in the classification of the subject's condition as OSA or CSA. For example, in this example, the amplitude pattern of breathing and it's envelop, as described above and shown illustratively in FIG. 11, can be used as a criteria for this distinction. For example, a CSA event is generally characterized by a typical decrescendo-crescendo pattern of breathing (e.g. see FIG. 19A), whereas an OSA event is generally preceded by a gradual decrease in breathing depth (i.e. due to gradual collapse of the upper airway, discussed below) and followed by an abrupt resumption of breathing (e.g. see FIG. 19B).

Given this observation, the system can be configured to automatically evaluate the features of the extracted envelopes around an identified apneic/hypopneic event to at least contribute in classifying such event as indicative of CSA or OSA, e.g. by distinguishing crescendo-decrescendo patterns 616 from gradual fall-abrupt rise patterns 618, respectively.

In one particular example, the following approach is implemented. As noted above, CSA is characterized by a crescendo-decrescendo pattern of ventilation and thus both edges preceding and following a CSA are generally similar mirror images of each other. On the other hand, OSA is caused by a gradual drop in ventilation due to upper airway collapse, but is terminated by an arousal that triggers a sudden opening in the upper airway and an abrupt rise in the breath sounds. Accordingly, an OSA event generally has two dissimilar edges. Therefore, in this particular example, OSA can be distinguished from CSA by testing the similarity between the falling and rising edges of a given event.

Figure 22:
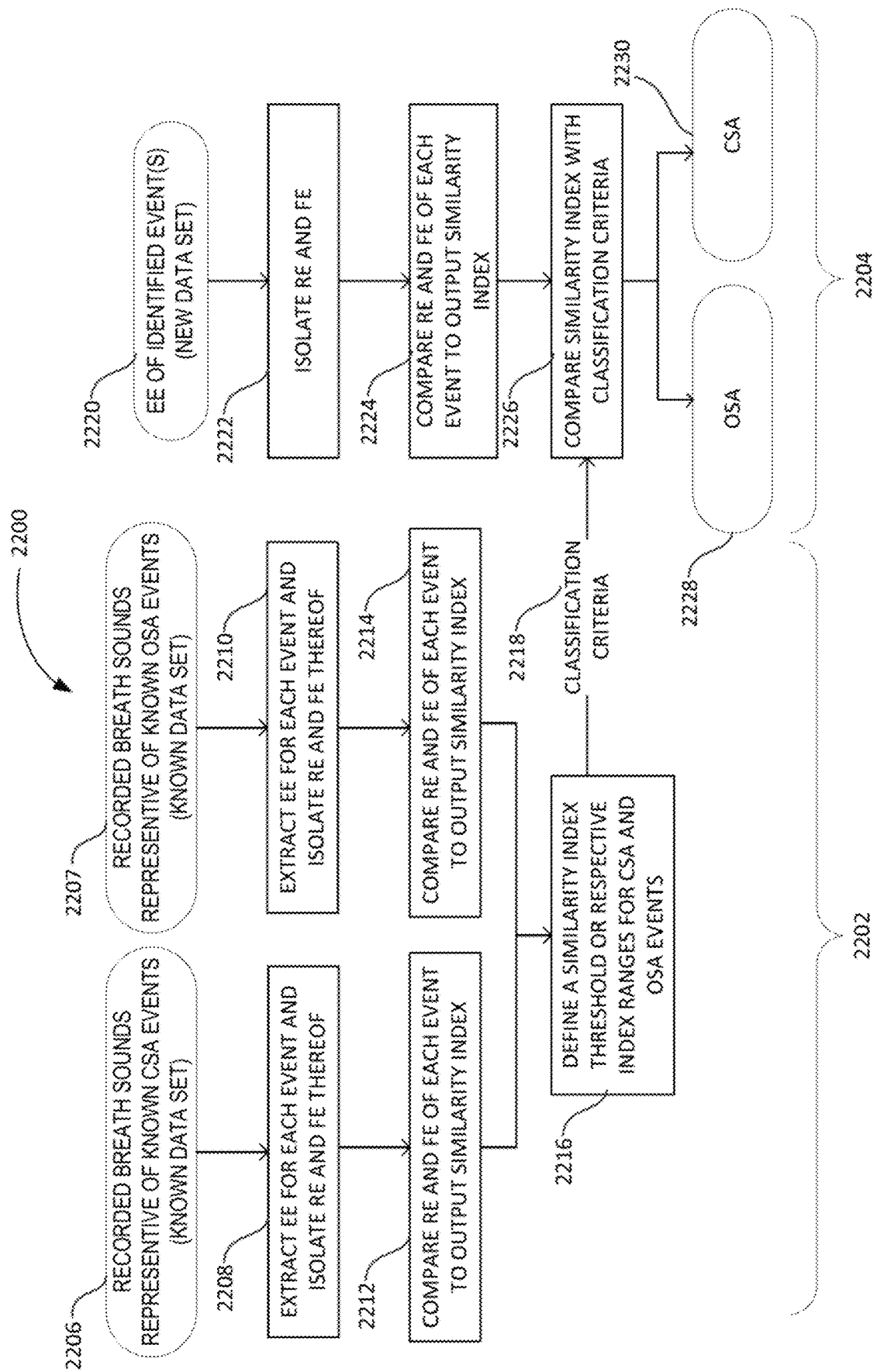
FIG. 22 is a flow chart of a method for automatically evaluating and classifying the fall/rise patterns, as illustrated in FIGS. 21A and 21B, as representative of CSA or OSA.

An example of a classification model based on this approach is provided in FIG. 22, in accordance with one illustrative embodiment of the invention. In particular, process 2200 can be subdivided into two main branches: a training phase 2202 and an implementation phase 2204. During the training phase 2202, a known data set consisting of known OSA (2206) and CSA (2207) events (e.g. breath sounds recorded during known apnea/hypopnea events independently associated with CSA and OSA, respectively) are processed, as described above, so to first extract an effort envelope (EE) around each event and isolate the rising edge (RE) and falling edge (FE) thereof (steps 2208 and 2210). The RE and FE of each event are compared (e.g. via Dynamic Time Warping (DTW), discussed below) for CSA and OSA events respectively (steps 2212 and 2214), to output respective similarity indexes representative of each condition. Based on the outputs of steps 2212 and 2214, similarity index ranges and/or thresholds are defined at step 2216 for each condition and set as classification criteria 2218 for the implementation phase 2204. In the below example, a similarity index threshold (DTW threshold) of between about 50 to 100 was identified to differentiate between CSA (below threshold) and OSA (above threshold) candidates.

With added reference to FIG. 6B, the implementation phase 2204 of process 2200 may be applied to newly acquired breath sound data, which in the context of process 600, has already been processed to extract the EE of respective events of interest 2220. At step 2222, the RE and FE of each event is isolated and compared at step 2224 (e.g. via DTW) to output a similarity index to be associated with each event. The output similarity index(es) may then be compared at step 2226 with the classification criteria 2218 set therefor (e.g. either individually or as a group by way of a computed similarity index mean or distribution), the result of which comparison leading to an indication of possible OSA 2228 or CSA 2230 (e.g. output 618 and 616 of FIG. 6B, respectively). As discussed further below, the recorded data may be processed by segments or event-by-event to produce a series or distribution of local outputs, or in its entirety to produce a singular local output for downstream consideration. Where an overall local output of the process 2200 leads to conflicting results or results deemed to fall within an invalid or indefinite range, the process 2200 may be configured to automatically output an error code or value instructing downstream globalization processes to disregard this branch of the characterization process 600.

Figure 20A:
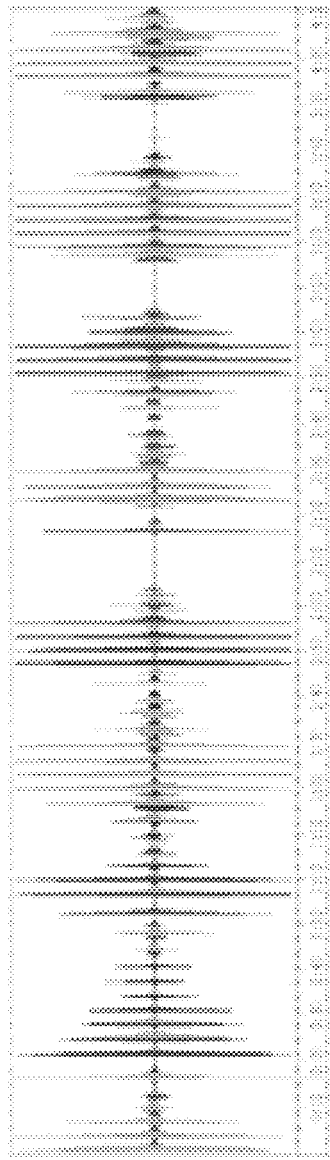
Figure 20B:
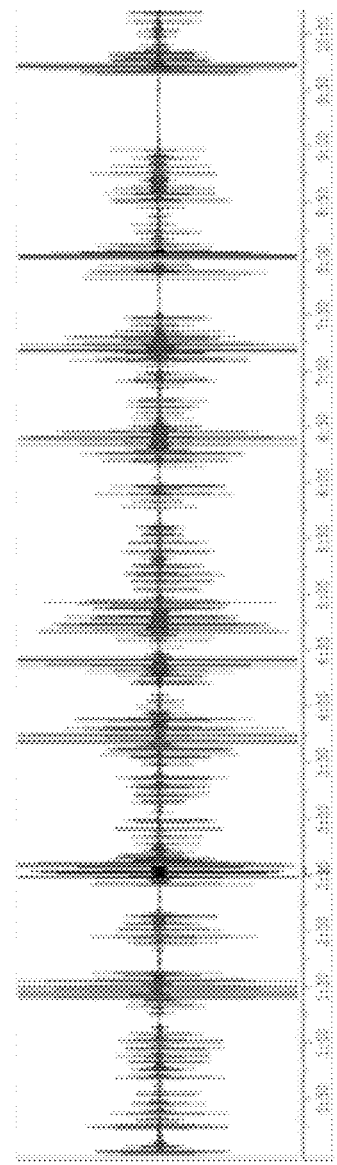
FIG. 20B illustrates a gradual reduction and abrupt resumption pattern generally associated with OSA, in accordance with one embodiment of the invention.
Figure 21A:
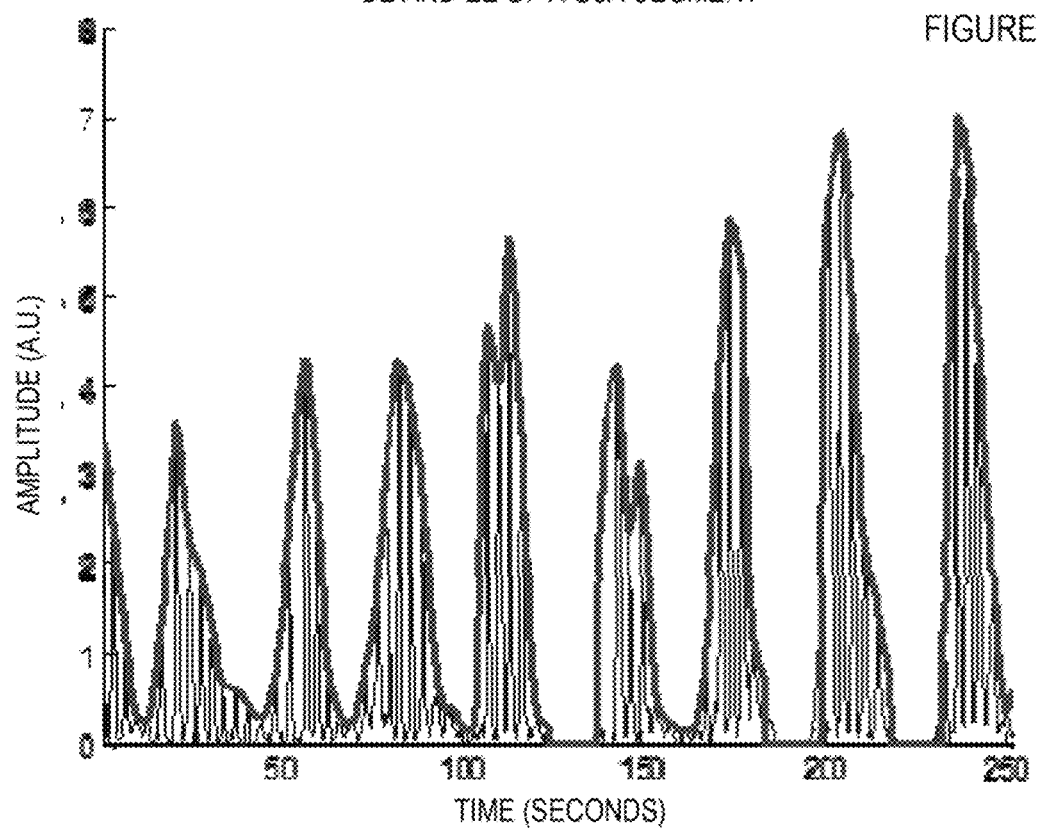
FIGS. 21A and 21B are plots of breathing and effort envelopes extracted for each of the raw waveforms of FIGS. 20A and 20B, showing envelope fall/rise patterns characteristic of CSA and OSA, respectively.
Figure 21B:
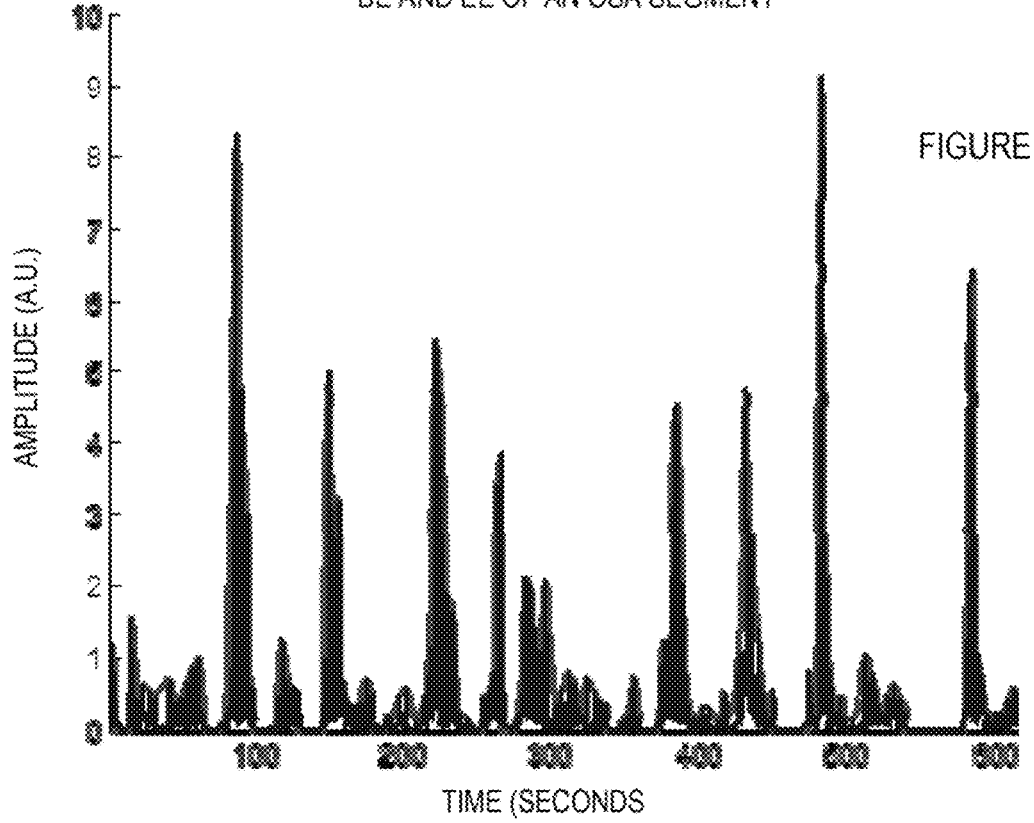

In one example of the above-described process, breath sounds were recorded simultaneously with PSG (as described earlier) so to generate a known data set in training a classifier to automatically differentiate between events likely associated with OSA or CSA. PSG traces were processed manually by trained technicians and all apneas/hypopneas and their types were identified and labeled. Subsequently, 2 random candidates were selected, a patient having generated CSA events and another patient having generated OSA events. The time stamp of a sequence of apneas/hypopneas was identified from the PSG for each candidate. Using the time stamps, corresponding breath sound segments were extracted from both samples (FIGS. 20A and 20B, respectively). BS and EE for both segments were computed, from which the fall and rise pattern distinctions manifested for the CSA and OSA patients could be observed, as shown for example in FIGS. 21A and 21B, respectively. Four events from each segment were identified, and the falling and rising edge from each one was isolated. In this example, the similarity between the falling and rising edge isolated for each event was measured using Dynamic Time Warping (DTW). The mathematical basis for DTW is explained below, for completeness. In general, where the two edges are similar, the DTW procedure will output a lower value, whereas for dissimilar edges, a much higher value will be outputted. In the illustrated example, the mean DTW output for CSA events was 7.5, whereas the mean DTW output for OSA events was 420.8.

From these results, a DTW output threshold selected between 50 and 100 can be used in subsequent implementation phases to accurately distinguish events as potentially representative of OSA or CSA. Namely, in one such embodiment, a fall/rise pattern evaluation module, such as module 614 of FIG. 6B, may be set to compare, such as in step 2226 of FIG. 22, DTW outputs automatically calculated in respect of identified events with a preset DTW threshold to classify the candidate's isolated events as representative of OSA (DTW output>DTW threshold) or CSA (DTW output<threshold). Again, where a local DTW output falls too close to a selected threshold, or again where a statistically significant number of events lead to conflicting results, the process 2226 may be configured to output an error code or indication as to the conflict, for further consideration.

For completeness, a brief overview of the DTW process is provided below, in accordance with one embodiment of the invention.

DTW assumes that two sequences, p and q, are similar but are out of phase and are of length n and m, respectively, where $p=\{p_1, \ldots, p_n\}$ and $q=\{q_1, \ldots, q_m\}$. The objective is to compute the matching cost: DTW(p, q). To align the two sequences using DTW, an n×m matrix is constructed where the (i, j)-th entry of the matrix indicates the distance $d(p_i, q_j)$ between the two points $p_i$ and $q_j$, where $d(p_i, q_j)=(p_i, q_j)^2$. The cost of similarity between the two sequences is based on a warping path W that defines a mapping between p and q. The k-th element of W is defined as $w_k$ which is a pointer to the k-th element on the path, usually represented by the indices of the corresponding element. So, W is defined as $W=<w_1, w_2, \ldots, w_k, \ldots, w_L>$ such that, max(m, n)≤L<n+m−1.

The warping path is subject to two main constraints:
i) Boundary conditions: $w_1=(1, 1)$ and $w_L=(n, m)$, which entails that the warping path starts and ends in diagonally opposite corners of the matrix.
ii) Continuity and Monotonocity: Given $w_k=(a, b)$, and $w_{k-1}=(a', b')$, then $a' \leq a \leq a'+1$ and $b' \leq b \leq b'+1$. This casts a restriction on the allowable steps in the path to adjacent cells including diagonally adjacent cells, and forces the path's indices to be monotonically increasing. There are exponentially many warping paths that satisfy the above constraints. However, only the path that minimizes the warping cost is being sought, such that:

$$DTW(p,q) = \{\sqrt{\Sigma_{k=1}^{L} w_k}\}$$

The monotonically increasing warping path that minimizes the similarity cost between p and q is found by applying the dynamic programming formulation below, which defines the cumulative cost $D_{i,j}$ as the cost $d(p_i, q_j)$ in the current cell plus the minimum of the cumulative cost of the adjacent elements, $$D_{i,j} = d(p_i, q_j) + \min\{D_{i,j-1}, D_{i-1,j}, D_{i-1,j-1}\}$$

and consequently, $$DTW(p,q) = D_{n,m}$$

As will be appreciated by the skilled artisan, while the above proposes the use of DTW for automatically classifying identified events as representative of OSA or CSA as a function of extracted breathing effort envelope profile symmetries/asymmetries, other evaluation techniques may also be considered herein without departing from the general scope and nature of the present disclosure.

Periodic/Aperiodic Sound Analysis

With reference to FIG. 6B, periodic and/or aperiodic breathing sounds may also or independently be analyzed to contribute to the further identification, characterization and/or diagnosis of a subject's condition, for instance in this example, leading to a classification of a subject's sleep apnea as CSA or OSA. In this particular example, breathing sound data acquired via step 602 is analyzed to identify periodic (e.g. snoring) and aperiodic sounds (step 620), which identification can be used downstream in subsequent processes. For the sake of computational efficiency, periodicity identification can be implemented in parallel with breathing phase 608 and amplitude modulation steps 610, but may equally be implemented independently or sequentially without departing from the general scope and nature of the present disclosure.

In general, periodic sounds are those resulting from tissue vibration such as snoring. Aperiodic sounds are more generally attributed to turbulence that results from the passage of air through the upper airway. Accordingly, upon distinguishing periodic (622) from aperiodic (624) sounds, characterization of the subject's breathing condition can be further assessed. For instance, in one embodiment, the pitch stability of periodic sounds associated with each apneic/hypopneic event (e.g. sounds recorded during and around a given event, as identified at step 612) can be analyzed at step 626, wherein a relatively stable pitch is classified as being associated with a relatively stable airway (628) and thus most likely associated with CSA (606), as compared with a relatively unstable pitch that can be generally classified as being associated with a collapsible airway (630) and thus more likely associated with OSA (604). In general, snoring will take place during inspiration, though expiratory snoring may also occur.

Figure 23:
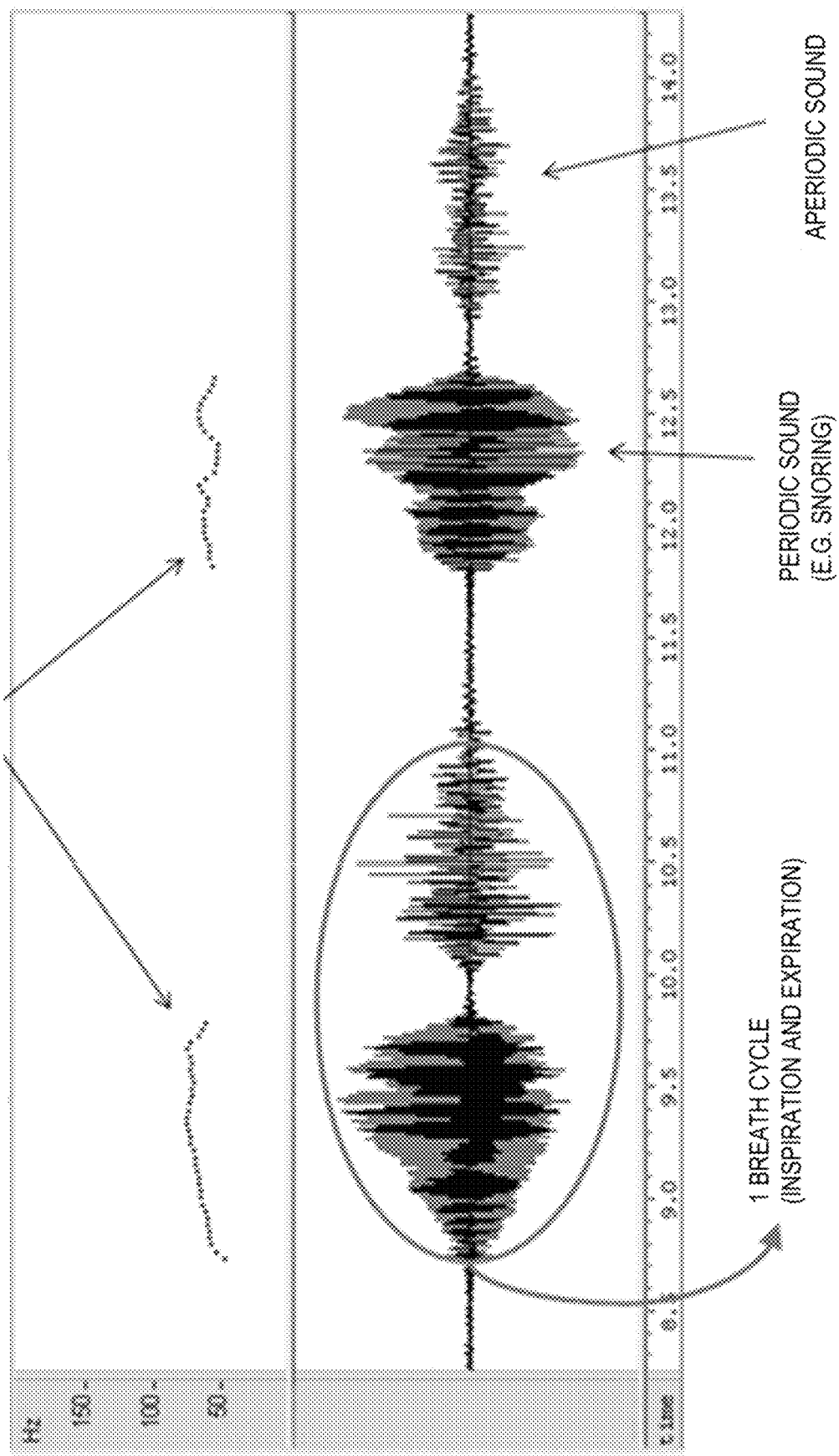
FIG. 23 is a plot of an exemplary fundamental frequency calculated for periodic breathing sounds identified during successive breathing cycles, in accordance with one embodiment of the invention.

In one exemplary embodiment, periodicity of the recorded sound is identified via a Robust Algorithm for Pitch Tracking (RAPT), which can be used not only to distinguish periodic from aperiodic sounds, but also calculate the pitch of periodic sounds, which calculated pitch can then be used for pitch stability analysis. As will be appreciated by the skilled artisan, RAPT has traditionally been used for detecting the fundamental frequency or pitch in speech analysis. By adjusting RAPT process parameters in this example, this process can be adapted, as shown in FIG. 23, for the purpose of analyzing breath sounds. For example, whereas RAPT is generally implemented for speech analysis in pitch frequency ranges of 100-200 Hz, this process is rather focused on more appropriate frequencies for periodic breathing sounds, such as 20-300 Hz, for example. Furthermore, a longer window length as compared to speech analysis applications is set to accommodate these lower frequencies and general snoring patterns. As will be appreciated by the skilled artisan, the RAPT process is generally configured to output for each processed window a periodicity identifier (e.g. 1 for periodic and 0 for aperiodic), and where periodicity is identified, a pitch frequency and probability or accuracy measure (e.g. based on signal autocorrelation), as well as other outputs not currently being used in current implementations. Based on this output, the method 600 may be configured with a preset lower accuracy threshold whereby any event (e.g. time period encompassing an identified apneic/hypopneic event) characterized by the RAPT process as periodic and exceeding this threshold may be retained as a periodic event, thus providing an automated means for identifying snoring during an event of interest. Results have shown a high degree of accuracy between manual snoring identification and the RAPT-based snoring identification process described herein, which thus facilitates breath sound analysis automation. While RAPT is discussed herein as an exemplary technique for identifying periodicity, other pitch tracking techniques can be used instead to achieve similar results, as will be appreciated by the skilled artisan.

As can be seen in the exemplary results of FIG. 23, periodic sounds are automatically identified from the inspiratory phase of successive breathing cycles (snoring generally absent during expiration). While breathing phase data as identified at step 608 can be used to isolate inspirations for this process, given the general absence of periodic sounds during expiration, such timing data is generally not required and can thus be omitted in calculating pitch stability (e.g. the process will automatically isolate periodic phases and process pitch stability therefrom).

Collapsible Airway Detection Via Periodic Breath Sound Analysis

Figure 24A:
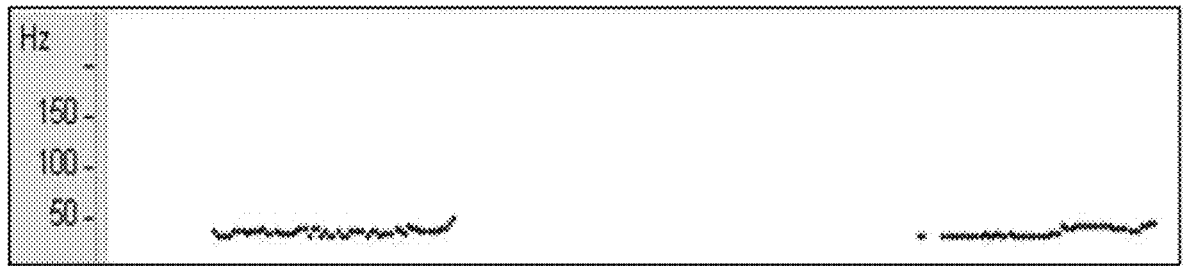
Figure 24B:
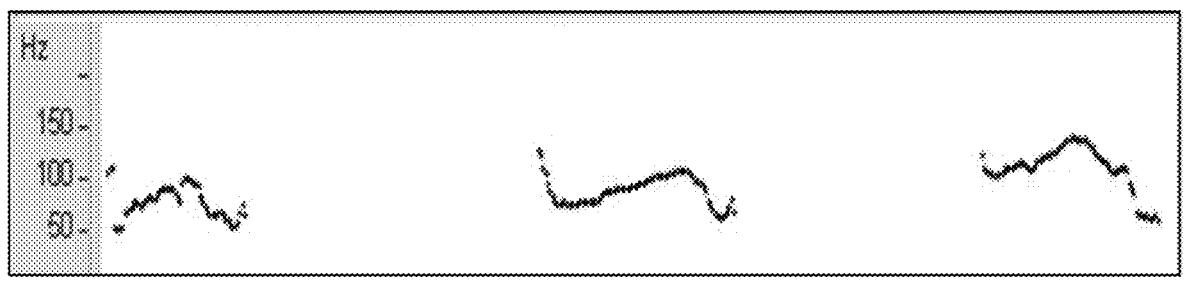

As noted above, periodic sounds such as snoring can be examined for signs of narrowing versus patency. In the upper airway, snoring is generated by the collision of tissue flaps. Accordingly, the pitch of snoring is generally determined by the number of tissue collisions (e.g. vibrations), which is calculated using RAPT in this example. Due to this mechanism of snore production, a characteristic pitch nature can be found in OSA due to tissue collapse. Namely, with OSA, the distance between tissue flaps of the pharynx can vary due to its narrowing and collapsibility. This results in pitch fluctuations intra-snore and inter-snore. FIGS. 24A and 24B illustrate typical pitch contours for the two types of snoring. FIG. 24A shows the pitch contour of snoring from a subject without sleep apnea; the contour is relatively flat, which denotes stability of the pharyngeal tissue. Comparatively, FIG. 24B shows the pitch contour of snoring taking place during an obstructive hypopnea (OSA), clearly showing a rather curvy contour resulting from the instability of the pharyngeal tissue.

Accordingly, where the pitch contour identified from periodic breathing sounds is identified as remaining relatively stable, step 626 will identify this event as exhibiting a relatively stable airway and thus, where sleep apnea is suspected from other steps in process 600, likely indicative of CSA. It will be appreciated that habitual snorers who do not suffer from sleep apnea will not be distinguished by this step alone, nor will all candidates suffering from CSA exhibit snoring. Nonetheless, identification of a stable airway during snoring will nonetheless allow for the differentiation between habitual snorers and CSA sufferers, from those potentially suffering from OSA. Namely, where the pitch during these cycles is identified as variable or fluctuating, step 626 will identify this event as exhibiting a collapsing airway and thus likely indicative of OSA. Different techniques can be used to automatically evaluate the stability of the periodic pitch data in making this distinction, namely in classifying identified periodic sounds as relatively stable versus relatively variable. For instance, the herein-contemplated embodiments can be configured to identify and analyze not only sudden changes or jumps in pitch, but also evaluate a curviness of the pitch even in the absence of jumps, for example.

Figure 26:
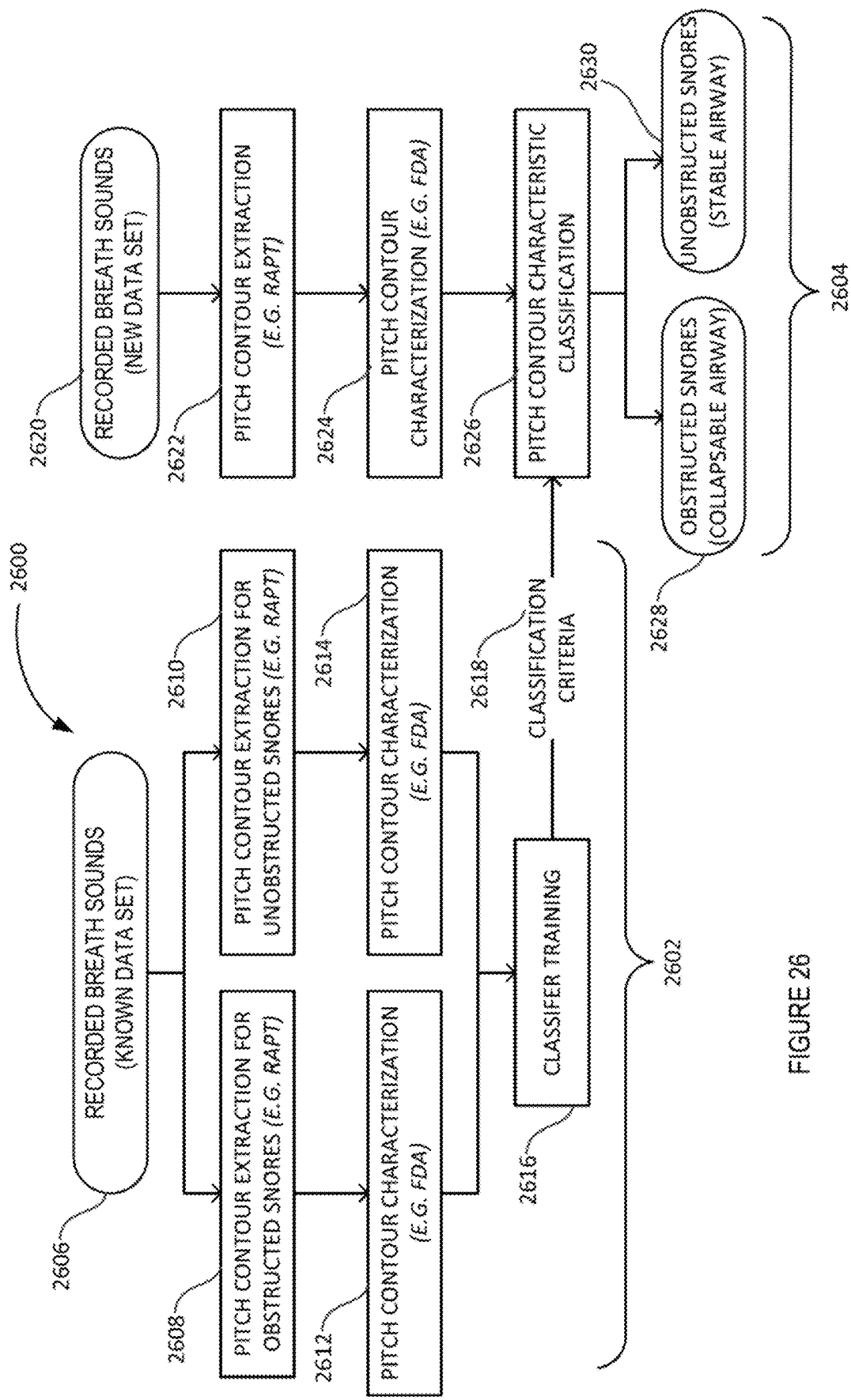
FIG. 26 is a flow diagram of a process for automatically classifying extracted pitch contours as representative of obstructed and unobstructed snoring events, in accordance with one embodiment of the invention.

An example of a classification model based on this approach is provided in FIG. 26, in accordance with one illustrative embodiment of the invention. In particular, process 2600 can be subdivided into two main branches: a training phase 2602 and an implementation phase 2604. During the training phase 2602, a known data set 2606 (e.g. breath sounds recorded during known apnea/hypopnea events independently associated with OSA) are processed (e.g. via RAPT) so to first isolate periodic breath sound segments and extract therefrom respective pitch contours for known obstructive and non-obstructive snoring segments (steps 2608 and 2610, respectively). Extracted contours are then characterized (e.g. via FDA, as in the below example) at steps 2612 and 2614, and the distinguishable characteristics thereof retained in training a classifier 2616 selected so to produce classification criteria 2618 usable in subsequent classifications. Various pitch contour characteristics in the time, frequency and time/frequency domain may be selected in optimizing classification criteria based on a given training data set, as will be readily appreciated by the skilled artisan.

With added reference to FIG. 6B, the implementation phase 2604 of process 2600 may be applied to newly acquired breath sound data 2620. At step 2622, the recorded breath sounds are first processed (e.g. via RAPT) so to isolate periodic breath sound segments therein and extract therefrom respective pitch contours. As noted above, the recorded data may be processed in its entirety, or again automatically pre-segmented into regions of interest using previously extracted apnea/hypopnea timing data (e.g. extracted at step 612 of FIG. 6B). In either case, the isolated periodic breath sound pitch contours are further processed at step 2624 (e.g. via FDA) to extract therefrom classifiable characteristics preselected during the training phase 2602. Upon comparing at step 2626 the contour characteristics identified at step 2624 with the classification criteria 2616 set during the training phase 2602, processed segments representative of obstructive snoring events can be classified as such at output 2628 (collapsible airway output 630 of FIG. 6B), and classified as non-obstructive snoring events otherwise at output 2630 (stable airway output 628 of FIG. 6B).

In the below example, and in accordance with one embodiment, Functional Data Analysis (FDA) can be used to provide automatic distinction between regular snores and those associated with obstruction. FDA is generally known in the art as a collection of statistical techniques for analyzing data arranged in the form of curves, surfaces and the like when varying over a continuum. In this particular example, FDA can be used in relation to the intra-snore contours over a time continuum. For example, FDA can be used in this context based on the identified rates of change or derivatives of the output curves, or again use the slopes, curvatures and/or other characteristics relying on the generally smooth nature of the output curves. Namely, since the general pitch contour patterns manifested by of the two types of snoring events differ in terms of complexity and variation over time, different measures of waveform complexity can also be used such as mean, standard deviation, variance, zero crossing of demeaned waveform, turns count, mobility, or a combination thereof, to name a few. Furthermore, FDA being applied on functions rather than scalars, it may allow one to make quantitative inferences from sets of whole continuous functions (e.g. signals) without the need for an intermediate step in which functions are converted into scalars, an intermediate process that can lead to information loss and thus reduce the efficiency and/or accuracy of such methods in making inferences from dynamic traits of processed signals. By characterizing the curves typical to each type of snoring using FDA, distinguishing features may be preset within the system for automatic identification of each type of snoring.

Figure 25:
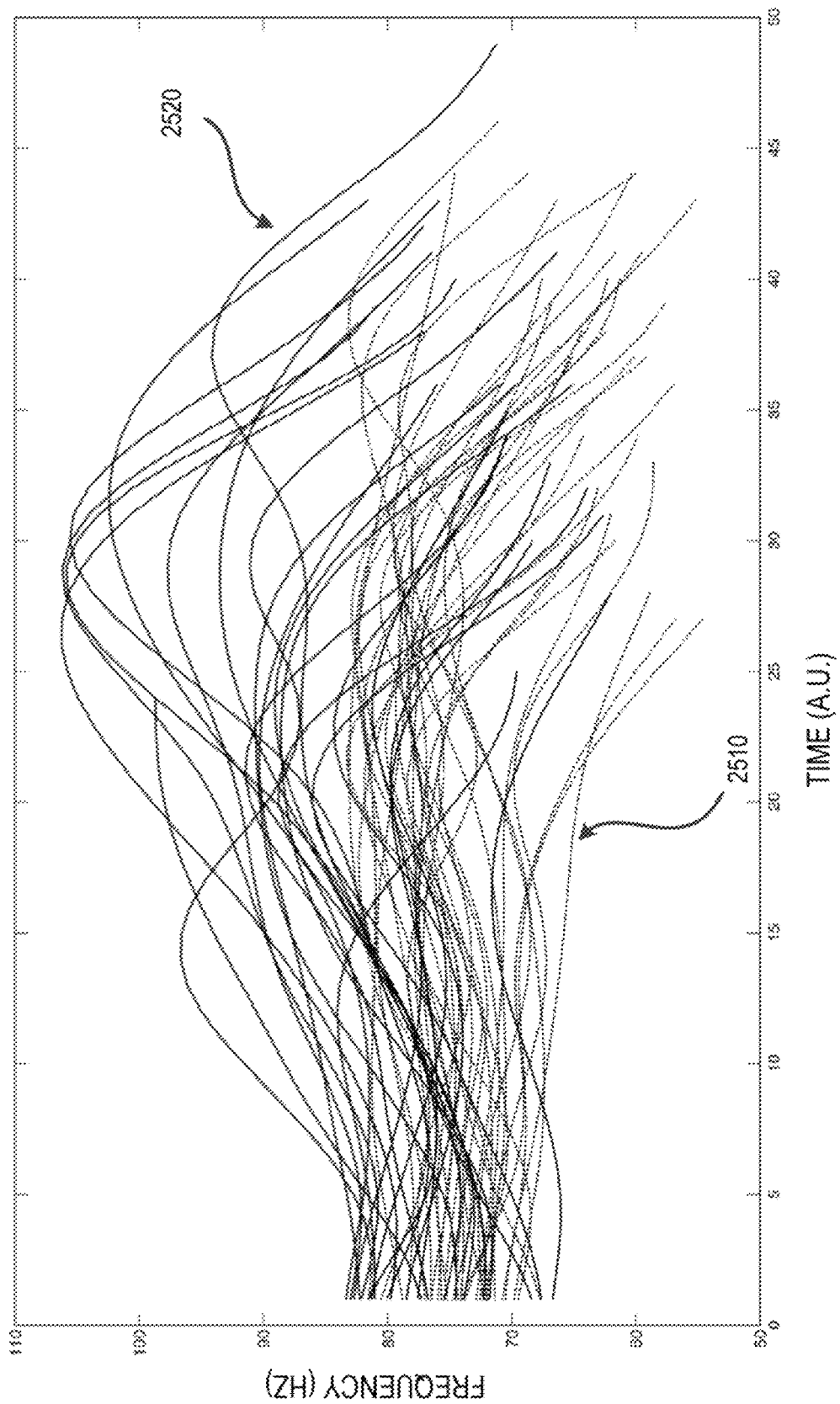
FIG. 25 is a plot of multiple pitch contours extracted from breath sounds recorded during non-obstructive/normal (dashed lines) and obstructive/hypopneic (solid lines) snoring events, respectively, for a candidate undergoing simultaneous PGS and breath sound analysis.

In one embodiment, FDA is therefore used as an example to build a classification model that can take into consideration the characteristic shape and time dynamics of the 2 sets of functions, i.e. obstructive and non-obstructive snoring event pitch contours (e.g. as plotted in FIG. 25 in dashed and solid lines, respectively). The classification model can then be used to classify future samples of snoring sounds exhibiting similar characteristics.

Figure 27A:
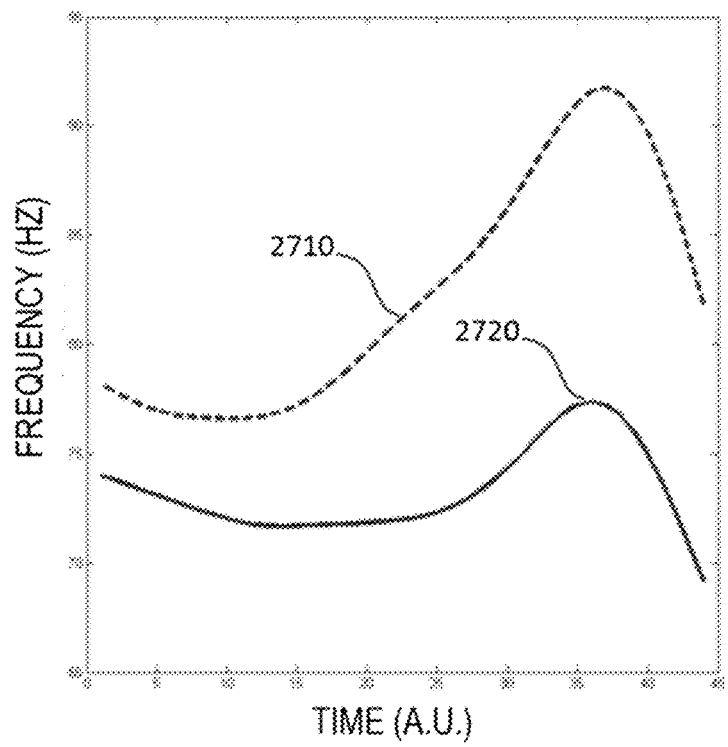
FIG. 27A is a plot of illustrative mean curves for the respective families of obstructive/hypopnea snoring pitch contours (dashed curve) and non-obstructive/normal snoring pitch contours (solid curve) of FIG. 25, defining exemplary classification criteria for distinguishing obstructive and non-obstructive snoring events identified from breath sound recordings, in accordance with an embodiment of the invention.
Figure 27B:
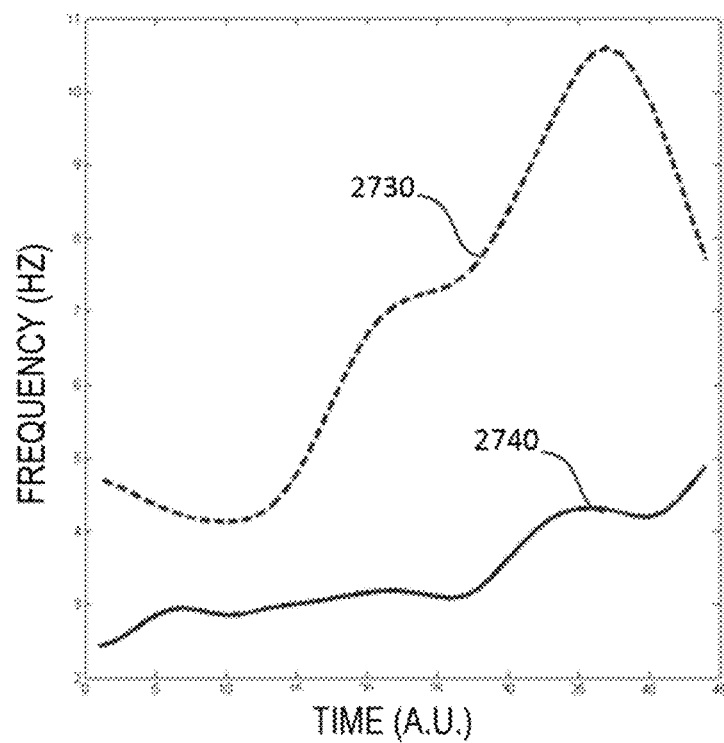
FIG. 27B is a plot of illustrative mean curves for the respective families of obstructive/hypopnea snoring pitch contours (dashed curve) and non-obstructive/normal snoring pitch contours (solid curve) of FIG. 25, defining another exemplary classification criteria for distinguishing obstructive and non-obstructive snoring events identified from breath sound recordings, in accordance with an embodiment of the invention.

For the purpose of illustrating the above-described approach to obstructed snore identification, the following illustrative example is provided with reference to FIGS. 25 to 27. A candidate undergoing parallel PSG and acoustic breath sound analysis (described above) was identified using the PSG results to have OSA. A two minute segment of the breath sound data was isolated from a data window devoid of apneas and/or hypopneas but during which the candidate was snoring, and another two minute segment was isolated from a window in which obstructive hypopneas were identified, again in the presence of snoring. Overall, the non-obstructed breath sounds window included 31 snoring episodes whereas the obstructed breath sounds window included 29 snoring episodes. Using RAPT in this example, the fundamental frequency (F0) of each snore episode was calculated and plotted, as shown in FIG. 25 for obstructed breath sounds 2520 (solid lines) and unobstructed breath sounds 2510 (dashed lines), respectively.

As exemplified by the sequential pitch contours of FIG. 24A, and again by the overlapped pitch contours 2510 shown as dashed lines in FIG. 25 of this example, a non-collapsing upper airway will generally result in a more stable snoring vibration. On the other hand, snoring that takes place during obstructive respiratory events generally results in a fluctuating pitch contour, as exemplified by the sequential pitch contours of FIG. 24B, and again by the overlapped pitch contours 2520 shown as solid lines in FIG. 25B. In one embodiment, a comparative process may thus be implemented to automatically classify a pitch contour derived (e.g. via RAPT) from recorded breath sounds as indicative of a stable (normal) or collapsible (obstructive) airway, and thus usable in classifying a candidate's condition as CSA (or normal) vs. OSA.

The identification of snoring pitch contour classification criteria (e.g. criteria 2618 of FIG. 26) was demonstrated in accordance with the following process.

Each pitch contour was first smoothed using wavelet de-noising in order to endow each record with a 'functional representation'. Other smoothing techniques can be used such as B-spline curve fitting, Fourier smoothing, or polynomial smoothing, to name a few.

The smoothed dataset of curves was then cleaned by discarding a small subset of short curves that were shorter than half the length of the longest curve, so to facilitate the below assessment and establishment of exemplary classification criteria.

The curves from each family (obstructive and non-obstructive) were temporally aligned, or 'registered', using dynamic time warping (DTW—discussed above) in order to eliminate unchecked phase variations that can lead to inflated amplitude variability estimates.

The sample mean curve and the sample variance curve for each family were then computed and temporally aligned/registered, as shown in FIG. 27A (mean curve for obstructive 2710 (dashed) and non-obstructive 2720 (solid) pitch contour families) and 27B (variance curves for obstructive 2730 (dashed) and non-obstructive 2740 (solid) pitch contour families).

In order to determine whether the sets of mean and variance curves had arisen from the same statistical distribution, the average difference between the two sample mean curves was statistically tested to assess whether it was approximately zero. In other words, the families of curves were compared as coherent entities rather than as unconnected, independent points.

Statistical comparison was performed based on the null hypothesis that the difference between the means of the two families of curves is zero. In other words:

$$H_0: f_1(t) - f_2(t) = 0$$

The first step in this statistical analysis was to compute the standardized difference between the registered means, and then to compute the discrete Fourier decomposition of the standardized difference. Next, a vector of the Fourier coefficients was constructed and used to estimate an adaptive Neyman statistic. Consequently, the p-value of the test statistic value was estimated by Monte Carlo simulation of a large number of vectors whose elements were drawn from a standard normal distribution. In general, when two sets of curves arise from the same random function, the standardized differences of their Fourier coefficients are normally distributed around 0. A p-value of 0.04<0.05 was obtained, and therefore, the null hypothesis was rejected indicating that the two sets of curves didn't arise from the same random function.

Accordingly, a characteristic mean and standard deviation can be generated for each condition (obstructive vs. non-obstructive), against which a test curve or group of curves representative of a new data set (e.g. extracted pitch contour(s) from unclassified periodic breath sound recording(s)) can be compared to yield a statistical result indicating the proximity of the test curve to either of the 2 families, thus providing an indication as to a most probable condition of the tested candidate (i.e. normal or CSA snoring vs. OSA snoring).

As will be appreciated by the skilled artisan, different parameters and/or thresholds may be applied in computing an overall local output where multiple snoring segments are processed for a given event, or again, for multiple events. For example, a minimum number of identified obstructive snoring events during a preset period and/or a minimum confidence value (e.g. a minimum distance from a preset criteria or curve) automatically output by the selected classifier may be required in one embodiment to output a collapsible airway classification, for instance, in reducing production of false positives which may ultimately bias outputs computed from parallel or downstream processes. Where an overall local output of the process 2600 leads to conflicting results or results deemed to fall within an invalid or indefinite range (e.g. unclassifiable data and/or a classification confidence value below a preset confidence threshold), the process 2600 may be configured to automatically output an error code or value instructing downstream globalization processes to disregard this branch of the characterization process 600.

It will be appreciated that while the process 600 of FIG. 6B contemplates the introduction of event specific-timing data at step 626 for the classification of periodic events as indicative of a stable or collapsing airway, such data may rather be introduced earlier in the processing stream to isolate events of interest prior to evaluating periodicity. This and other such permutations will be readily understood by the skilled artisan to fall within the general scope of the present disclosure.

Upper Airway Narrowing Detection Via Aperiodic Breath Sound Analysis

In the absence of snoring (e.g. where recorded sounds are generally classified as aperiodic at step 620), further processing may be implemented to identify the potential narrowing of the upper airway (step 632), wherein identified narrowing 634 may be indicative of OSA 604, as compared to an open airway 636, which is more likely indicative of CSA 606.

As introduced above, obstructive sleep apnea (OSA) is a breathing disorder characterized by repetitive cessations of breathing from 5 to 100 times/hour during sleep, each lasting 10-60 seconds, due to narrowing and collapse of the upper airway (UA). As noted above, one approach to identifying OSA is via the characterization of snoring sounds. Although snoring is a hallmark of OSA, it does not necessarily take place for each apnea and hypopnea. Accordingly, the disease severity might be underestimated if some apneas are missed due to the absence of snoring, for example. Therefore, and in accordance with the embodiment of FIG. 6B, the proposed breath sound analysis process takes into consideration both snoring and non-snoring components to further characterize the candidate's breathing during sleep. For example, non-snoring components of the recorded breathing sounds may result from turbulence created during the passage of air into and out of the lung through the upper airway (UA). The degree and character of air turbulence, considered in this embodiment during inspiration, is generally considered to be influenced by changes in UA caliber and airflow rate.

In one embodiment, the device and method as disclosed herein allows for the detection of upper airway narrowing, for example in the diagnosis of sleep apnea and other such breathing disorders. For example, as introduced above, step 632 may allow for the categorization of aperiodic (e.g. inspiratory) breath sounds as indicative of UA narrowing when such narrowing occurs. For instance, by previously identifying aperiodic breath sound signatures and correlating such signatures with occurrences of UA narrowing, the system can be configured to compare aperiodic signatures identified in respect of a subject's breathing sound recording with preset signatures so to classify the newly acquired signatures as indicative of UA narrowing, as the case may be, thus contributing to the characterization of the subject's condition as more readily indicative of OSA vs. CSA. In this particular example, a correlation between upper airway (UA) narrowing and aperiodic sound signatures was identified using Linear Prediction Coding (LPC), which relies on similarities identified between aperiodic breathing sounds and the generation of unvoiced fricative sounds in speech production, whereby in each case, the quality or signature of sounds generated are recognized to vary according to the degree of narrowing. Using this analogy, the methods and devices herein described allow, based on breath sound analysis, for the objective detection of UA narrowing occurrences, which detected occurrences may then be used, in accordance with some embodiments, in sleep apnea diagnosis. For example, in one embodiment, variations are detected in pure turbulent breath sound qualities in correlation with a change of a quantitative index of UA narrowing, thus leading to an objective detection of UA narrowing occurrences.

In this particular example, aperiodic breath sound signatures were developed and correlated with an UA narrowing index to classify recorded breath sounds based on a level of UA narrowing. For the purpose of process 600, it will be appreciated that different levels of UA narrowing identification may lead to different degrees of diagnostic accuracy; however, a binary system whereby candidates with significant UA narrowing (e.g. above a certain classification threshold) are distinguished from those with little to no UA narrowing, may be sufficient in contributing to the overall classification process.

To first define and classify aperiodic breath sound signatures in accordance with UA narrowing, and further to validate the accuracy of this approach, the following test was implemented. In 18 awake subjects, UA resistance ($R_{AU}$), an index of UA narrowing, was measured simultaneously with breath sounds recording. Linear Prediction Coding (LPC) was applied on turbulent inspiratory sounds drawn from low and high $R_{AU}$ conditions and k-mean was used to cluster the resulting coefficients. The resulting 2 clusters were tested for agreement with the underlying $R_{AU}$ status. Distinct clusters were formed when $R_{UA}$ increased relatively high but not in cases with lower rise in $R_{UA}$ (P<0.01 for all indicators.).

Figure 28:
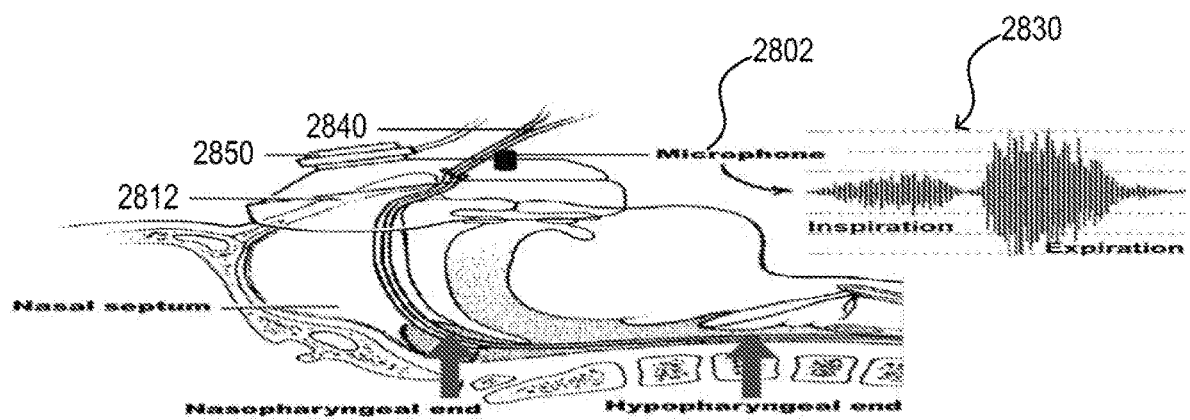
FIG. 28 is a schematic diagram of a system for validating upper airway (UA) narrowing detection achieved via breath sound analysis in accordance with one embodiment of the invention.

With reference to FIG. 28, a system 2800, similar to that depicted in FIG. 1, is shown as used to develop and validate a method for UA narrowing detection via breath sound analysis, implemented in accordance with one embodiment of the invention. The system 2800 generally comprises a face mask 2812 having a microphone 2802 embedded therein for disposal at a distance from a nose and mouth area of the subject's face, from which breath sounds may be recorded, for example as shown illustratively by sample waveform 2830. Face masks as shown in the embodiments of FIGS. 2 to 4, and others like them, may also be used in this context, as will be understood by the skilled artisan. Pharyngeal catheters 2840 and a pneumotachometer 2850, as used in the below-described example, are also shown for purpose of validating breath sound analysis, and in generating a training data set from which classification criteria may be identified and set for the subsequent automated classification of unknown data sets. A recording/processing module (not shown), such as recording/processing module 120, 220 and 330 of FIGS. 1, 2, and 3, respectively, is again included to record breath sounds captured by the microphone 2802, and process same in implementing, at least in part, the steps described below.

In the following example, data were collected from 18 subjects (4 women, 14 men, age=55.6±10.2, body mass index (BMI)=32.2±8.7, AHI=36.73±20.80).

In this particular example, breath sounds were recorded using a cardioid condenser microphone (MX185, Shure®) in front of the subject's nose and embedded in a full face mask 2812 that was strapped to the head as shown in FIG. 28. Digitized sound data were transferred to a computer using a USB preamplifier and audio interface (M-Audio, Model Fast Track Pro USB) again with a sampling rate (Fs) of 22050 Hz and resolution of 16 bits. Acquired sound was bandpass-filtered at 20-10,000 Hz.

As it has been shown that UA narrowing in OSA is at least partially a consequence of fluid shift from the lower body into the neck, a fluid displacement from the legs was induced to simulate UA narrowing via application of lower body positive pressure (LBPP) using inflatable trousers. Namely, this approach has been shown to narrow the UA and increase UA resistance ($R_{UA}$), presumably due to accumulation of fluid around the UA. In particular, a pair of deflated medical anti-shock trousers (MAST III-AT; David Clark, Inc.) was wrapped around both legs from the ankles to the upper thighs of supine awake subjects. For the control arm of the test, trousers were left deflated, and for the LBPP (simulated UA narrowing) arm, trousers were inflated to 40 mmHg to force fluid out of the legs. The subjects were then crossed over to the opposite arm. The duration of each arm lasted 20 minutes. The first five minutes of each arm was a baseline (BL) period, which was used as a reference for the subsequent changes in $R_{UA}$ and breath sounds. Breath sounds and $R_{UA}$ values from the same arm were compared to each other to avoid any possible effect of the change of microphone position during the cross-over.

Run was then measured as an index of UA narrowing. $R_{UA}$ was measured by dividing transpharyngeal pressure (difference between nasopharyngeal and hypopharyngeal pressure measured by two catheters 2840 as shown in FIG. 28) by simultaneous airflow rate measured by a pneumotachometer 2850 attached to the outlet of the facemask given by $R_{UA}=\Delta P/F$. and is expressed in cm·H$_2$O/Liter/second. $R_{UA}$ was calculated at the lowest value of airflow every 30 seconds. Breath sound recordings were synchronized with the pressure and airflow signals in order to correlate sound characteristics with $R_{UA}$.

In one embodiment, breath sounds are limited to turbulent inspiratory sounds, whereby expiratory sounds may be excluded to avoid the effect of expired airflow on the microphone 2802, for example.

In one embodiment, snoring and/or wheezing sounds were also excluded, (e.g. as identified at step 620 of FIG. 6B, discussed above.

In this example, two sets of sounds were collected from each experimental arm: one set from the BL and another set at the point at which peak $R_{UA}$ occurred in each of the control and LBPP arms. Each subset of inspiratory sounds was annotated according to the $R_{UA}$ value that accompanied that subset of sounds. Depending on the length of the breathing cycles, 2 to 5 inspirations were selected within each epoch for each $R_{UA}$ value for further processing.

In one embodiment, and as noted above, Linear Predictive Coding (LPC) can be used to identify UA narrowing from recorded breath sound data. For example, LPC can be used as a modeling technique for speech signals, in particular unvoiced speech sounds, in order to capture the shape of the vocal tract. Namely, LPC generally assumes that the upper airway is a tube that has certain resonant frequencies and can thus capture the resonant characteristics of the upper airway.

In the present context, upper airway narrowing is expected to result in morphological changes that will modulate resonant characteristics of the upper airway, which modulated characteristics can be observed via LPC to provide useful information regarding the subject's airway, and thus the potential breathing disorders this information may suggest.

Figure 29:
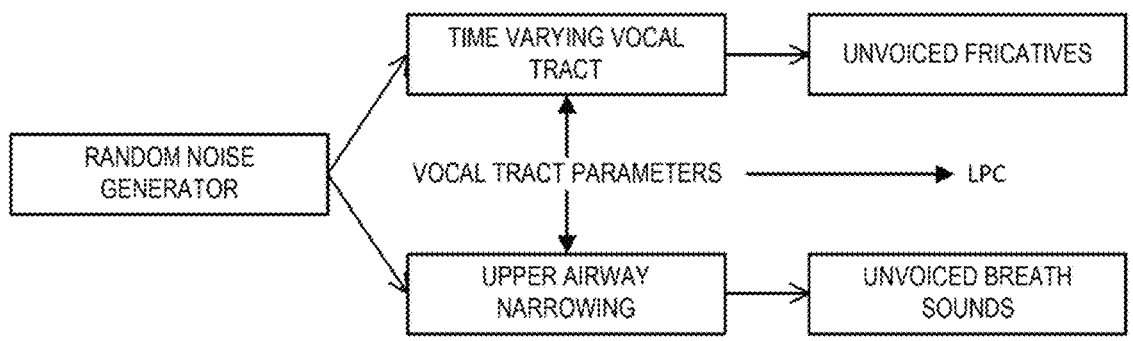
FIG. 29 is a diagram of an analogy relied upon for UA narrowing detection, in accordance with one embodiment of the invention, between a Linear Prediction Coding (LPC) modeling of unvoiced speech sounds and that of turbulent breath sounds.

The LPC model of unvoiced speech sounds assumes a random noise generator as an excitation source. Turbulent breath sounds share this feature with unvoiced speech sounds because both are generated as a result of the passage of air through the UA, whether fully patent or narrowed, but without the occurrence of tissue vibration such as snoring. LPC models the vocal tract, or the upper airway in this context, as an all-pole filter given by:

$$H(z) = \frac{1}{1 - \sum_{i=1}^{p} a_i z^{-i}}$$

with an LPC order p=6. FIG. 29 demonstrates the similarity between LPC implementation in speech and breath sounds, as considered in this embodiment.

Figure 30:
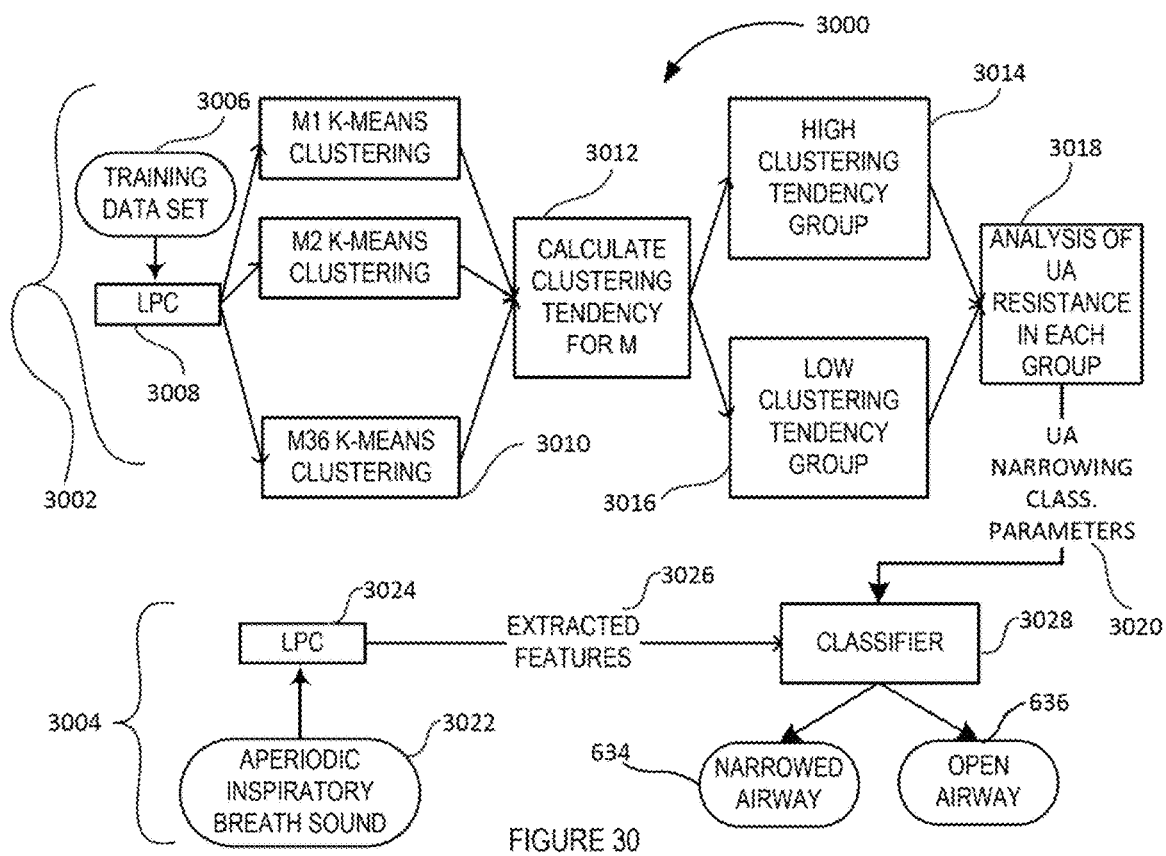
FIG. 30 is a flow chart of a data clustering and analysis method for identifying UA narrowing from acquired breath sounds, in accordance with one embodiment of the invention.
Figure 31:
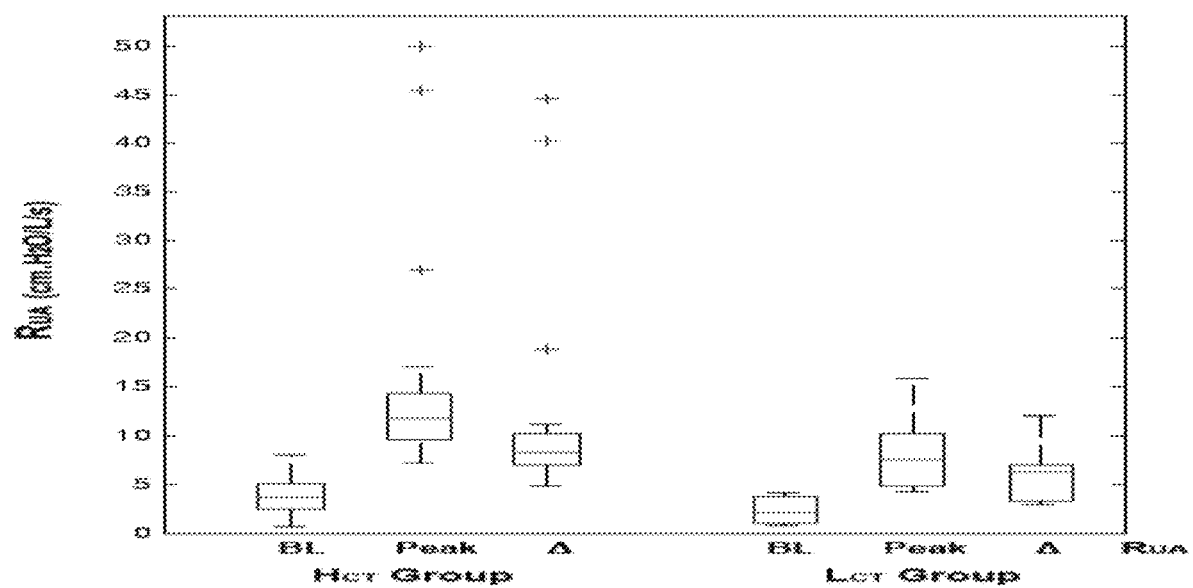
FIG. 31 is a box plot of a calculated UA narrowing index ($R_{UA}$) in a high clustering tendency group ($H_{CT}$) and a low clustering tendency group ($L_{CT}$), in accordance with one embodiment of the invention.

Reference will now be made to FIG. 30, in which an exemplary process 3000 is shown for training and implementing an LPC-based classifier for the classification of aperiodic inspiratory breath sounds as most likely resulting from an open or narrowed airway, in accordance with one embodiment of the invention.

As in process 2200 and 2600 described above, process 3000 may also be subdivided into two main branches: a training phase 3002 and an implementation phase 3004. During the training phase 3002, a known data set 3006 consisting of breath sounds known to be recorded in the presence and absence of upper airway narrowing is first generated. This data set is then processed, via LPC in this example (step 3008), so to extract characteristic features or coefficients of the recorded sounds. In the below example, LPC was applied in accordance with the following.

Because breath sounds vary in amplitude due to their cyclic nature, they were normalized in amplitude to remove the effect of gain in the LPC model. The signal's envelop was found by calculating a moving average of the signal's variance using a 1,100 point (50 ms) window and then normalizing to that envelop.

Pre-emphasis was applied to compensate for the inherent spectral tilt similar to the application of LPC in speech.

In order to apply LPC on equal length segments, normalized breath sounds were segmented with a Hamming window of length ~250 ms with a frame rate of 200 ms.

Using this approach, an average of 272±82 vectors of LPC coefficients were obtained from the 36 experimental arms.

Following from the above, and in accordance with one embodiment, the training data was classified into a number of clusters, for instance to detect the presence of distinct clusters in each of M=36, each derived from an experimental arm, in accordance with the following.

The 6th order LPC coefficients were selected as a feature of the classifier, and a clustering algorithm (k-mean in this example), was implemented on M=1 to 36 with a total of 272±82 LPC vectors in each M (steps 3010). The number of clusters was forced into 2 based on the knowledge of the 2 underlying conditions, i.e. BL and peak $R_{UA}$.

To measure the ability of k-mean to separate LPC vectors in M based on the underlying $R_{UA}$ status, BL and peak $R_{UA}$, the sum of LPC vectors in each of the 2 resulting clusters for each status was calculated at step 3012 as:

$$T = \sum_{i=0}^{n} \left(\frac{x_i}{s_i^{(l)}}\right) \in C_j$$

which is the sum of the LPC vectors $x_i$ in each inspiratory sound segment $s_l$, where n is the total number of vectors in M, l is the number of inspiratory segments in the data set, and $C_j$ is each of the resulting clusters (j=1,2). Where this sum showed that 75% or more of sound segments originating from BL aggregated in a distinct and different cluster from those originating from Peak $R_{UA}$, each of the 2 clusters was said to be the correct cluster ($C_{cor}$) for that $R_{UA}$ state and that arm was said to have high clustering tendency (3014). On the other hand, if this result is below 75% or if BL and Peak $R_{UA}$ sounds do not aggregate in distinct clusters, then this case was said to have low clustering tendency (3016).

The overall classification accuracy in differentiating between supposedly different sounds was calculated by calculating the weighted sum of the percentages of LPC vectors $x_i$ in each segment $s_l$ that were classified in $C_{cor}$:

$$A = \sum_{l=0}^{m} w_l \cdot \sum_{i=0}^{n} \left(\frac{x_i}{s_i^{(l)}}\right) \in C_{cor}$$

where weight $w_l$ is equal to the number of frames in each inspiration divided by the total number of frames in a single arm.

All acoustic processing techniques in this example were implemented in MATLAB™ (version 7.9.0 R2009b), though other processing platforms may be considered herein without departing from the general scope and nature of the present disclosure.

From the aforementioned calculations, inferences were made at step 3018 on the relation between $R_{UA}$ values of BL and Peak $R_{UA}$ on one hand and clustering tendency on the other, thus identifying a relationship between detected sound properties and $R_{UA}$. The relations were statistically tested using the Wilcoxon rank sum test or t-test depending on the data distribution type, and used to define UA narrowing classification criteria 3020 for subsequent use in the implementation phase 3004.

Out of 36 experimental arms, 27 showed high clustering tendency ($H_{CT}$ group) and 9 showed low clustering tendency ($L_{CT}$ group). The characteristics of those groups are shown in Table 4 and FIG. 31. In the $H_{CT}$ group, the peak $R_{UA}$ was 14.9±10.2 units, which was significantly higher than that in $L_{CT}$, 8±3.8 (p=0.0041). Similarly, the difference between BL and peak $R_{UA}$ ($\Delta R_{UA}$) in $H_{CT}$ group was 11±9.4, which is significantly higher than $\Delta R_{UA}$ in $L_{CT}$ group, 5.7±3 (p=0.0089). These results show that the increase in $R_{UA}$ results in change in voice qualities that can be detected with LPC. The overall accuracy of breath sound classification was 84.7±7.9% vs. 58.6±5.7% in $H_{CT}$ and $L_{CT}$ respectively (P<0.0001). All of those parameters show clearly that LPC coefficients of turbulent breath sounds vary when a rise of $R_{UA}$ takes place above a certain level, but do not when the rise is to a lower degree or absent. Since $R_{UA}$ is an indicator of UA narrowing, the above-described process can be used in the present context to further identify and/or characterize a subject's condition, which may lead to a more accurate diagnosis thereof, for example, when combined with the local outputs of the other processing branches described above.

TABLE 4

Summary of $R_{UA}$ values according to the clustering tendency.

| $R_{UA}$ Status | $H_{CT}$ | $L_{CT}$ |
|---|---|---|
| BL $R_{UA}$ | Average = 3.9 ± 1.9<br>Median = 3.6 | Average = 2.2 ± 1.3<br>Median = 2.1 |
| Peak $R_{UA}$ | Average = 14.9 ± 10.2<br>Median = 11.7 | Average = 8 ± 3.8<br>Median = 7.6 |
| Δ $R_{UA}$ | Average = 11 ± 9.4<br>Median = 8.3 | Average = 5.7 ± 3<br>Median = 6.3 |
| A | Average = 84.7 ± 7.9<br>Median = 84.5 | Average = 58.6 ± 5.7<br>Median = 58.8 |

A, overall accuracy (%) given by equation 3.

With added reference to FIG. 6B, the implementation phase 3004 of process 3000 may be applied to newly acquired breath sound data 3022, namely aperiodic inspiratory breath sound segments during or around previously identified events in this example (e.g. identified via steps 608, 612 and 620 of FIG. 6B). At step 3024, the recorded breath sounds are first processed (e.g. via LPC) so to generate extractable features 3026 (e.g. one or more LPC coefficients) to be compared by classifier 3028 with the preset UA narrowing classification criteria 3020, in classifying the processed event as indicative of an open or narrowed airway. For example, the classifier 3028 may be configured to output a narrowed airway indication where extracted features fall within a preset range or above or below a preset threshold and otherwise default to an open airway indication. Where extracted features 3026 provide conflicting results or fall outside classifiable ranges prescribed by the classification criteria 3020, the classifier 3028 may be configured to output an error code or value indicative of such conflicting results so to not adversely affect a global output of process 600, for example.

Figure 32:
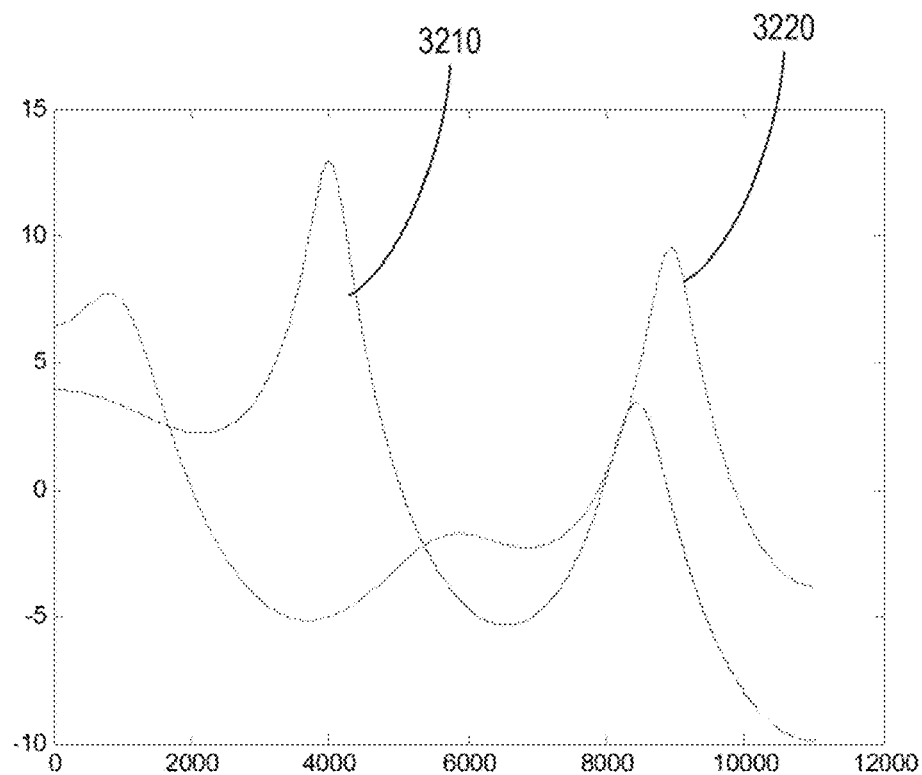
FIG. 32 is a plot of exemplary low resistance and high resistance (UA narrowing) patterns exhibited in LPC spectra computed for a given candidate from recorded breath sounds, in accordance with an embodiment of the invention.

As will be appreciated, the various processing parameters described in the above example may be modified to provide similar results, and that, without departing from the general scope and nature of the present disclosure. For example, alternative LPC features to be used by k-mean to distinguish the different types of breath sounds may be considered, as can classification techniques other than k-mean. For instance, FIG. 32 provides an example of LPC spectra generated using LPC coefficients, wherein curve 3210 is the LPC spectrum generated during a low resistance status and curve 3220 is an LPC spectrum generated during a high resistance status in the same person. As can be seen by this example, the locations of spectral peaks (also called formants) have shifted in time, as did amplitudes and frequencies. Accordingly, similar to the above implementation of a classification technique using k-mean on the original LPC coefficients, LPC spectra, spectral peak locations, spectral peak amplitudes, peak separation, and the like can also or alternatively be used as discriminating features between high and low resistance status, and thus to contribute in the classification of recorded breath sounds as indicative of OSA vs. CSA.

Likewise, other supervised or unsupervised pattern recognition algorithms such as fuzzy c-means, artificial neural networks, support vector machines, and Hidden Markov Models, may be used instead of k-mean to provide similar results.

Since LPC is a frequency spectrum based technique that represents the frequency spectrum in smooth curves with emphasis on peaks, techniques other than LPC may also be considered to provide a like effect, such as by leveraging characteristics of FFT and mel-frequency cepstrum coefficients (MFCC), for example.

As shown above, LPC and its equivalents can be used, in accordance with some embodiments of the invention, to characterize turbulent (aperiodic) breath sounds as indicative of an open or narrowed airway. As will be appreciated by the skilled artisan, the ability to distinguish normal breath sounds (represented herein by the BL conditions), from those resulting from partial narrowing (represented herein by peak $R_{UA}$) provides a useful alternative or compliment to periodic breath sound analysis, as contemplated above with reference to FIG. 23 to 26.

Global Output

Figure 33:
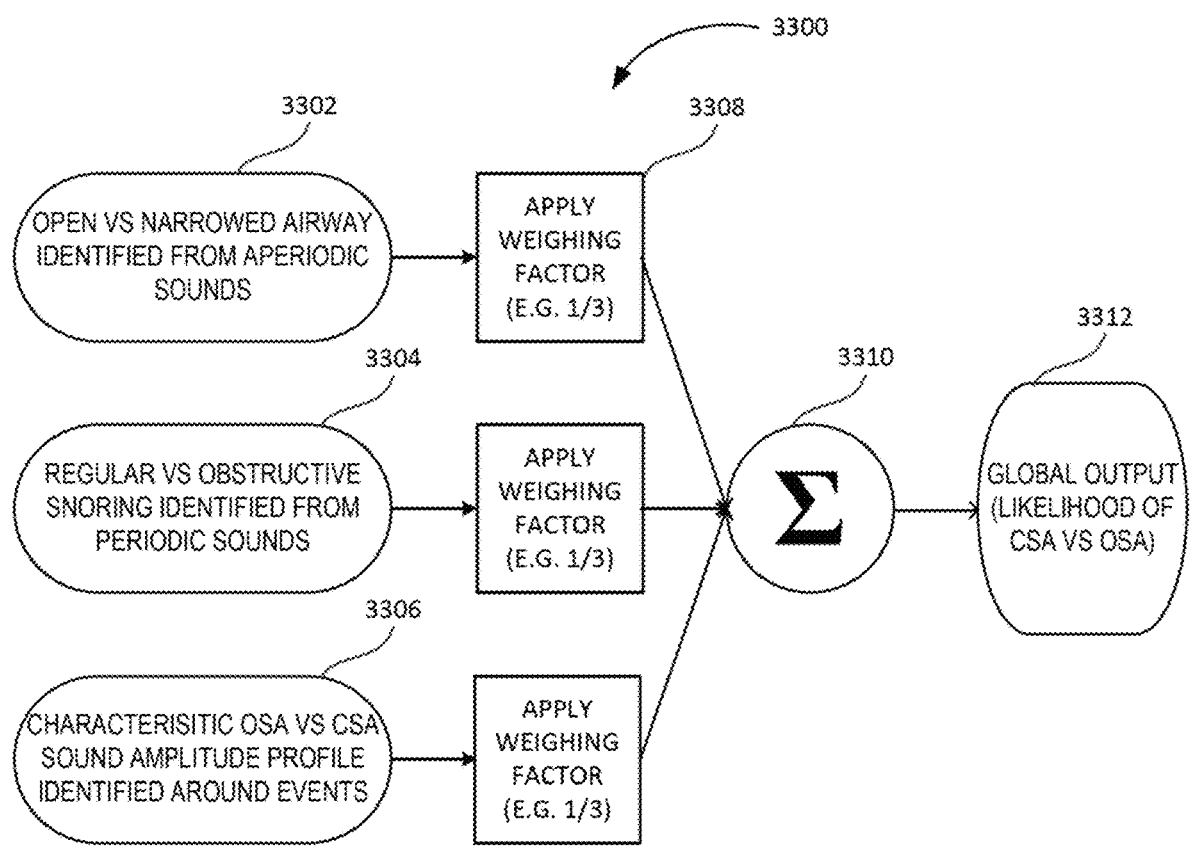
FIG. 33 is a flow chart of an automated decision process for outputting, responsive to multiple local outputs received from respective upstream breath disorder characterization processes, a global characterization of the subject's condition, in accordance with one embodiment of the invention.

With reference to FIG. 33, and in accordance with one embodiment of the invention, the local outputs form the various processes described above generally with reference to FIGS. 6A and 6B, can be combined to produce a global output determination indicative of the most likely characterization of the subject's condition. In this example, the global classifier 3300 receives a local output indication from each of the aperiodic sound evaluation module 3302 (e.g. output from step 662 of FIG. 6A; narrowed airway output 634 or open airway output 636 from step 632 of FIG. 6B); periodic sound evaluation module 3304 (e.g. output from step 660 of FIG. 6A; collapsible airway output 630 or stable airway output 628 from step 626 of FIG. 6B); and sound amplitude profile evaluation module 3306 (e.g. output from step 658 of FIG. 6A; gradual fall/abrupt rise output 618 or crescendo/decrescendo output 616 from step 614 of FIG. 6B). A pre-selected weighing factor is then applied to each local output at step 3308 so to adjust an effect each one of these outputs is to have on the global output. For example, where a given processing branch is deemed to provide statistically more significant results, the local output of this processing branch may have a higher weighing associated therewith to counterbalance potentially less accurate results received from other branches. In other embodiments, a local output may be provided along with a confidence value automatically calculated thereon as a function of a classification accuracy estimated by each processing branch. For example, where a local output was classified based on a comparison of the output value with a threshold value or range, a distance of this output value from the threshold, for example, may be used to associate a confidence level to the output, whereby a local output value that is well within range or below/above a preset threshold may have a high confidence level associated therewith, as compared to an output value relatively close to such threshold or barely within a preset range and with which a low confidence level may be associated. In this example, an equal weighing of ⅓ is associated with each local output by default. At step 3310, the respective local outputs are combined to produce a global output indication 3312, for example by way of a simple majority voting process whereby one of CSA and OSA is deemed to be the most likely classification, or again by way of a weighed sum of respective local outputs to produce an output probability for each possible output, to name a few. Where conflicting local outputs are entered, the system may be configured to output an error or "unclassifiable" code, or again output details as to the various conflicts identified between respective local outputs. In another example, the system may rather be configured to output a default value (e.g. OSA) unless a combination of local outputs exceeds a preset probability threshold (e.g. 75%) for an alternative classification (e.g. CSA). Likewise, the global output indicator 3312 may also be configured to output a severity index or value (e.g. AHI), as shown by output 640 of FIG. 6B

It will be appreciated that other global output combination and/or classification techniques may be considered herein without departing from the general scope and nature of the present disclosure. It will further be appreciated that different outputs may be considered depending on the complexity and overall purpose of the device. For example, where the device is used for screening purposes in referring a subject to further tests and/or diagnostics, the device may be configured for home use and to provide a singular output indicative as to whether the candidate should seek consultation with a professional. In such embodiments, the data may be extractable by such professional for further processing, or again to "unlock" further diagnostics, which may include, each local output, a global output as noted above, or a combination thereof, for example. In other embodiments, the device may rather be configured to acquire data only, and leave processing thereof to be implemented at a remote diagnostic location, where again, various levels of data outputs may be provided or rendered available depending on the intended purpose of the device and the sophistication of the attendant tasked with interpreting the output. Accordingly, different output levels, configurations, and complexities may be considered herein without departing form the general scope and nature of the present disclosure.

It will also be appreciated that, while different process streams are presented above with reference to a combined embodiment leveraging multiple local outputs in outputting a global or combined output, different embodiments may only implement one or two of the above-described process streams (i.e. periodic sound analysis, aperiodic sound analysis, sound amplitude profile analysis, or different combinations thereof) to achieve similar results, and that, without departing from the general scope and nature of the present disclosure. Accordingly, it will be appreciated that the scope of this application is not to be limited to a three-pronged process, but rather should be considered to include different combinations and permutations of the above-described examples.

While the present disclosure describes various exemplary embodiments, the disclosure is not so limited. To the contrary, the disclosure is intended to cover various modifications and equivalent arrangements included within the spirit and scope of the appended claims. The scope of the following claims is to be accorded the broadest interpretation so as to encompass all such modifications and equivalent structures and functions.

The invention claimed is:

1. A computer-implemented method, automatically implemented by one or more processors of a computing device, for automatically characterizing recorded digital breath sounds acquired from a candidate while sleeping, as potentially indicative of an obstructive breathing disorder, the method comprising:

receiving, at the at least one processor, the recorded digital breath sounds of an upper airway of the candidate;

automatically identifying inspiration and expiration phases of said recorded digital breath sounds;

automatically identifying, by the at least one processor, periodic breath sound segments and aperiodic breath sound segments from the recorded digital breath sounds;

automatically identifying at least one apnea or hypopnea from the expiration phases of the recorded digital breath sounds;

based on the identified apnea or hypopnea, automatically selecting one or more of said aperiodic breath sound segments so to encompass corresponding ones of said at least one apnea or hypopnea, and to classify the said at least one apnea or hypopnea as being associated with a central sleep apnea versus an obstructive sleep apnea;

extracting from the identified periodic breath sound segments, by the at least one processor, one or more periodic breath sound characteristics;

evaluating, by the at least one processor, the extracted periodic breath sound characteristics against one or more corresponding periodic breath sound classification criteria predetermined to distinguish obstructive periodic breathing events from non-obstructive periodic breathing events;

extracting from inspiration phase of the selected aperiodic breath sound segments, by the at least one processor, one or more aperiodic breath sound characteristics comprising one or more upper airway narrowing characteristics;

evaluating, by the at least one processor, the extracted aperiodic breath sound characteristics against one or more corresponding aperiodic breath sound classification criteria predetermined to distinguish obstructive aperiodic breathing events from non-obstructive aperiodic breathing events;

identifying, by the at least one processor, a time-domain breath sound amplitude profile segment of the recorded digital breath sounds encompassing said at least one of an apnea and a hypopnea;

evaluating, by the at least one processor, the time-domain breath sound amplitude profile segment against one or more preset time-domain sound amplitude profile criteria set to recognize a profile pattern indicative of said obstructive apnea;

combining, by the at least one processor, results of the three evaluating steps to provide an indication as to whether the candidate likely suffers from the obstructive breathing disorder, the indication generated based upon a classifier, the classifier receiving results of the three evaluating steps as inputs, and outputting the indication using a display device in communication with the at least one processor.

2. The method of claim 1, further comprising automatically selecting one or more of said periodic breath sound segments so to encompass corresponding ones of said at least one apnea or hypopnea.

3. The method of claim 1, at least one of said periodic breath sound characteristic and said aperiodic breath sound characteristic comprising a frequency-domain characteristic.

4. The method of claim 1, said one or more aperiodic sound characteristic comprising a least one of a linear predictive coding (LPC) coefficient and a characteristic of an LPC spectrum.

5. The method of claim 1, said periodic breath sound characteristic comprising an extracted pitch contour characteristic.

6. The method of claim 5, said one or more periodic breath sound classification criteria comprising respective preset pitch contour characteristics predetermined from a pre-classified set of obstructive breathing events and a pre-classified set of non-obstructive breathing events.

7. The method of claim 6, each of said preset pitch contour characteristics comprising a mean pitch contour and a standard deviation thereof.

8. The method of claim 1, said identifying periodic breath sound segments and aperiodic breath sound segments step comprising implementing a pitch tracking subroutine on the recorded digital breath sounds to thereby simultaneously output identification of said periodic breath sound segments and a pitch variation manifested therein from which a pitch contour characteristic may be extracted.

9. The method of claim 1 wherein,
said identifying periodic breath sound segments and aperiodic breath sound segments step comprising excluding expiration phase sounds from said aperiodic sound segments, said periodic sound segments, or both said period sound segments and said aperiodic sound segments.

10. The method of claim 1, said one or more preset sound amplitude profile criteria further set to recognize a profile pattern indicative of central apnea and thereby not indicative of an obstructive disorder.

11. The method of claim 10, said profile pattern indicative of the central apnea comprising a substantially symmetrical fall/rise pattern characterized by similar falling and rising edges.

12. The method of claim 1, said profile pattern comprising an obstructive fall/rise pattern characterized by dissimilar falling and rising edges delineating the apnea or hypopnea.

13. A non-transitory computer-readable medium comprising instructions stored thereon for implementation by one or more processors of a computing system to automatically characterize recorded digital breath sounds acquired from a candidate while sleeping as potentially indicative of an obstructive breathing disorder, by:
receiving the recorded digital breath sounds of an upper airway of the candidate;
automatically identifying inspiration and expiration phases of said recorded digital breath sounds;
automatically identifying periodic breath sound segments and aperiodic breath sound segments from said recorded digital breath sounds;
automatically identifying at least one apnea or hypopnea from the expiration phases of the recorded digital breath sounds;
based on the identified apnea or hypopnea, automatically selecting one or more of said aperiodic breath sound segments so to encompass corresponding ones of said at least one apnea or hypopnea, and to classify the said at least one apnea or hypopnea as being associated with a central sleep apnea versus an obstructive sleep apnea;
extracting from said identified periodic breath sound segments one or more periodic breath sound characteristics;
evaluating said extracted periodic breath sound characteristics against one or more corresponding periodic breath sound classification criteria predetermined to distinguish obstructive periodic breathing events from non-obstructive periodic breathing events;
extracting from inspiration phase of said selected aperiodic breath sound segments one or more aperiodic breath sound characteristics comprising one or more upper airway narrowing characteristics;
evaluating said extracted aperiodic breath sound characteristics against one or more corresponding aperiodic breath sound classification criteria predetermined to distinguish obstructive aperiodic breathing events from non-obstructive aperiodic breathing events;
identifying a time-domain breath sound amplitude profile segment of the recorded digital breath sounds encompassing said at least one of an apnea and a hypopnea;
evaluating said time-domain breath sound amplitude profile segment against one or more preset time-domain sound amplitude profile criteria set to recognize a profile pattern indicative of said obstructive apnea;
combining results of the three of said evaluating steps to provide an indication as to whether the candidate likely suffers from the obstructive breathing disorder, the indication generated based upon a classifier, the classifier receiving results of the three evaluating steps as inputs, and
outputting said indication using a display device in communication with the at least one processor.

14. The computer-readable medium of claim 13, wherein said one or more aperiodic sound characteristic comprise at least one of a linear predictive coding (LPC) coefficient and a characteristic of an LPC spectrum.

15. The computer-readable medium of claim 13, wherein said periodic breath sound characteristic comprises an extracted pitch contour characteristic.

16. The computer-readable medium of claim 15, wherein said identifying periodic breath sound segments and aperiodic breath sound segments comprises implementing a pitch tracking subroutine on the recorded digital breath sounds to thereby simultaneously output identification of said periodic breath sound segments and a pitch variation manifested therein from which said pitch contour characteristic may be extracted.

17. The computer-readable medium of claim 13, wherein said one or more periodic breath sound classification criteria comprise respective preset pitch contour characteristics predetermined from a pre-classified set of obstructive breathing events and a pre-classified set of non-obstructive breathing events, wherein each of said preset pitch contour characteristics comprise a mean pitch contour and a standard deviation thereof.

18. A system for automatically characterizing recorded digital breath sounds acquired from a candidate while sleeping as potentially indicative of an obstructive breathing disorder, the system comprising:
one or more processors; and
instructions accessible by said one or more processors and executable to operate on said recorded digital breath sounds to:
receive the recorded digital breath sounds of an upper airway of the candidate;
automatically identify inspiration and expiration phases of said recorded digital breath sounds;
automatically identify periodic breath sound segments and aperiodic breath sound segments from said recorded digital breath sounds;
automatically identify at least one apnea or hypopnea from the expiration phases of the recorded digital breath sounds;
based on the identified apnea or hypopnea, automatically select one or more of said aperiodic breath sound segments so to encompass corresponding ones of said at least one apnea or hypopnea, and to classify the said at least one apnea or hypopnea as being associated with a central sleep apnea versus an obstructive sleep apnea;
extract from said identified periodic breath sound segments one or more periodic breath sound characteristics;

evaluate said extracted periodic breath sound characteristics against one or more corresponding periodic breath sound classification criteria predetermined to distinguish obstructive periodic breathing events from non-obstructive periodic breathing events;

extract from inspiration phase of said selected aperiodic breath sound segments one or more aperiodic breath sound characteristics comprising one or more upper airway narrowing characteristics;

evaluate said extracted aperiodic breath sound characteristics against one or more corresponding aperiodic breath sound classification criteria predetermined to distinguish obstructive aperiodic breathing events from non-obstructive aperiodic breathing events;

identifying a time-domain breath sound amplitude profile segment of the recorded digital breath sounds encompassing said at least one of an apnea and a hypopnea;

evaluating said time-domain breath sound amplitude profile segment against one or more preset time-domain sound amplitude profile criteria set to recognize a profile pattern indicative of said obstructive apnea;

combine results of the three of said evaluating steps to provide an indication as to whether the candidate likely suffers from the obstructive breathing disorder, the indication generated based upon a classifier, the classifier receiving results of the three evaluating steps as inputs, and output said indication using a display device in communication with the at least one processor.

19. The system of claim 18, further comprising a face mask having a microphone mounted thereon and reproducibly disposable, upon the candidate wearing the mask during sleep, at a distance above a nose and mouth area of the candidate.

\* \* \* \* \*